(12) United States Patent
Sekiguchi et al.

(10) Patent No.: US 8,148,571 B2
(45) Date of Patent: Apr. 3, 2012

(54) COMPOUND, COMPOSITION COMPRISING THE SAME, AND PROCESS FOR PRODUCTION OF POLYMERIZABLE AMIDE

(75) Inventors: Takahiro Sekiguchi, Kurashiki (JP); Ai Hinamoto, Kurashiki (JP)

(73) Assignee: Kuraray Medical Inc., Kurashiki-shi (JP)

( * ) Notice: Subject to any disclaimer, the term of this patent is extended or adjusted under 35 U.S.C. 154(b) by 362 days.

(21) Appl. No.: 12/443,620

(22) PCT Filed: Sep. 27, 2007

(86) PCT No.: PCT/JP2007/068781
§ 371 (c)(1), (2), (4) Date: Mar. 30, 2009

(87) PCT Pub. No.: WO2008/047547
PCT Pub. Date: Apr. 24, 2008

(65) Prior Publication Data
US 2010/0076157 A1    Mar. 25, 2010

(30) Foreign Application Priority Data

Sep. 29, 2006 (JP) .................. 2006-266500
Sep. 29, 2006 (JP) .................. 2006-266501

(51) Int. Cl.
C07F 9/09 (2006.01)
C07F 9/38 (2006.01)
A61K 6/00 (2006.01)
C07C 231/02 (2006.01)
C07C 233/47 (2006.01)

(52) U.S. Cl. ................. 562/8; 562/11; 562/23; 560/222

(58) Field of Classification Search .................. None
See application file for complete search history.

(56) References Cited

U.S. PATENT DOCUMENTS

| 4,310,517 | A | 1/1982 | Etschenberg et al. |
| 4,612,384 | A | 9/1986 | Omura et al. |
| 2004/0077754 | A1 | 4/2004 | Moszner et al. |
| 2007/0135632 | A1 | 6/2007 | Kunishima |

FOREIGN PATENT DOCUMENTS

| JP | 2004 131468 | 4/2004 |
| JP | 2006 76973 | 3/2006 |
| WO | 2005 075442 | 8/2005 |

OTHER PUBLICATIONS

Kuder et al Bioorganic and medicinal chemistry, 2000, 8(10), 2433-2439.*
Leventis, R. et al., "pH-Dependent Stability and Fusion of Liposomes Combining Protonatable Double-Chain Amphiphiles With Phosphatidylethanolamine", Biochemistry, vol. 26, No. 12, pp. 3267-3276 (1987).
Kuder, N. et al., "Synthesis of a Triply Phosphorylated Pentapeptide From Human τProtein", Bioorganic and Medicinal Chemistry, vol. 8, No. 10, pp. 2433-2439 (2000).
Sebastian, D. et al., "Selective Enzymatic Removal of Protecting Groups From Phosphopeptides: Chemoenzymatic Synthesis of a Characteristic Phosphopeptide Fragment of the Raf-1 Kinase", Synthesis, vol. 9, pp. 1098-1108 (1997).
Sebastian, D. et al., "Chemoenzymatic Synthesis of a Characteristic Phosphopeptide Fragment of the Raf-1 Kinase", Tetrahedron Letters, vol. 38, No. 17, pp. 2927-2930 (1997).
Kunishima, M. et al., "Formation of Carboxamides by Direct Condensation of Carboxylic Acids and Amines in *alcohols* Using a New Alcohol—and Water—Soluble Condensing Agent: DMT-MM", Tetrahedron, vol. 57, No. 8, pp. 1551-1558 (2001).
Nishiyama, N. et al., "Adhesiveness of N-Methacryloyl-ω-Amino Acid Primer to Dentin", Shikazairyo-Kikai, vol. 17, No. 2, pp. 120-125 (1998).

* cited by examiner

*Primary Examiner* — Yevegeny Valenrod
(74) *Attorney, Agent, or Firm* — Oblon, Spivak, McClelland, Maier & Neustadt, L.L.P.

(57) ABSTRACT

A novel compound (I) represented by the following formula (1) is provided which is suitable for a dental composition and has a polymerizable group, a carboxyl group and a phosphoric acid group. A method for producing a polymerizable amide is provided, which method can make a condensation reaction of a carboxylic acid with an amine to proceed easily and is excellent in safety: wherein $R^1$, $R^2$ and $R^3$ each independently are a hydrogen atom or a hydrocarbon group having 1 to 20 carbon atoms which may have a substituent; (A) and (B) are each any constituent unit; m is an integer of from 1 to 3; n is an integer of from 1 to 3; $R^4$ is an organic group having 1 to 40 carbon atoms which may have a substituent; $R^5$ is a hydrocarbon group having 1 to 20 carbon atoms which may have a substituent, $R^6$ and $R^7$ each independently are a hydrogen atom, a hydrocarbon group having 1 to 20 carbon atoms which may have a substituent, or a metal atom.

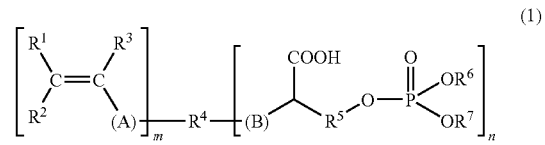

(1)

26 Claims, No Drawings

COMPOUND, COMPOSITION COMPRISING THE SAME, AND PROCESS FOR PRODUCTION OF POLYMERIZABLE AMIDE

This application is a 371 of PCT/JP07/68781, filed Sep. 27, 2007.

TECHNICAL FIELD

The present invention relates to a compound having a polymerizable group, a carboxyl group and a phosphoric acid group and to a composition containing the compound. It also relates to a method for producing a polymerizable amide by causing a carboxylic acid to undergo condensation reaction with an amine by using a triazine-based condensing agent.

BACKGROUND ART

For filling a repair material into a defective part of a tooth or covering a defective part of a tooth with a repair material, a dental adhesive is usually used. Known dental adhesives include one containing a compound having a polymerizable group and a phosphoric acid group.

For example, Japanese Laid-Open Patent Publication No. 2006-76973 (patent document 1) reports that a photopolymerization type adhesive for tooth structure adhesion which contains an acidic group-containing radically polymerizable monomer having a methacryloyl group and a phosphoric acid group, like 2-methacryloyloxyethylphosphoric acid, has a high tooth structure adhering performance to enamel and dentin. However, the bond strength was not necessarily high enough.

The Journal of Japanese Society for Dental Materials and Devices Vol. 17, No. 2 120-125 (1998) (non-patent document 1) discloses an N-methacryloyl-ω-amino acid which has a methacryloyl group in the molecule and is an amino acid derivative differing in the length of methylene chains (hereinafter, this may be abbreviated as "NMωA"). It is reported that when this NMωA is caused to apply as a primer on dentin collagen, the interaction between the NMωA and the dentin collagen increases and the bond strength between the dentin and a composite resin is improved as the methylene chain length of the NMωA increases. However, the improvement of materials with respect to bond strength has been desired.

When such a dental adhesive has been applied to the dentin, it is important for the adhesive to have a decalcifying function of dissolving the dentin surface with an acidic component, a permeating function that a monomer component permeates the collagen layer of the dentin, and a curing function that the permeating monomer component hardens to form a hybrid layer (hereinafter, this may be called "resin impregnated layer") with collagen.

Heretofore, there has been studied the simplification of the usage mode of dental adhesives from the three-bottle, three-step type in which the decalcifying function, the permeating function and the curing function are applied successively to the two-bottle, two-step type in which the decalcifying function and the permeating function are united, and further to the one-bottle, one-step type in which all the decalcifying function, the permeating function and the curing function are united. Compounds which can be used as dental adhesives which exert excellent adhesive properties in any usage mode have been desired.

Compounds having an amide bond or an ester bond, including the above-mentioned compound which can be used as a dental adhesive, are often important in view of their functions. As the method for synthesizing such a compound, there have been reported, for example, a method by which a compound having an amide bond is produced from a carboxylic acid and an amine by using a carbodiimide-based condensing agent represented by dicyclohexylcarbodiimide (hereinafter, this may be abbreviated as "DCC"), and a method by which a compound having an ester bond is produced from a carboxylic acid and an alcohol.

For example, Japanese Laid-Open Patent Publication No. 2004-131468 (patent document 2) discloses a method by which a carboxylic acid and an alcohol are caused to undergo dehydration condensation by using DCC to produce an acrylic acid ester phosphonic acid.

However, there are the following problems with methods using carbodiimide-based condensing agent represented by the DCC: (1) when there is a large amount of water in a reaction system, the proceeding of the reaction is inhibited. (2) When an alcohol is used as a reaction solvent, a side reaction, namely, condensation of the alcohol and a carboxylic acid, occurs. (3) When a carboxylic acid or an amine has a free hydroxyl group, a side reaction, namely, condensation of the free hydroxyl group and the carboxylic acid, occurs. (4) DCC tends to react with both a carboxylic acid and an amine. Therefore, DCC and the carboxylic acid are usually caused to react first, followed by addition of the amine. However, the yield of a compound having an amide bond may decrease depending upon the timing of the addition. (5) A care should be exercised in handling a carbodiimide-based condensing agent because it is prone to cause skin irritation.

Patent document 1: Japanese Laid-Open Patent Publication No. 2006-76973
Patent document 2: Japanese Laid-Open Patent Publication No. 2004-131468
Non-patent document 1: the Journal of Japanese Society for Dental Materials and Devices Vol. 17, No. 2 120-125 (1998)

DISCLOSURE OF THE INVENTION

Problems to be Solved by the Invention

The present invention has been accomplished in order to solve the above-described problems, and an object thereof is to provide a new compound (I) which is suitable for dental compositions and has a polymerizable group, a carboxyl group and a phosphoric acid group. Another object is to provide a method for producing a polymerizable amide, which method can make a condensation reaction of a carboxylic acid with an amine to proceed easily and is excellent in safety.

Means for Solving the Problems

The above-mentioned problems are solved by providing a compound (I) represented by the following formula (1):

[Chem. 1]

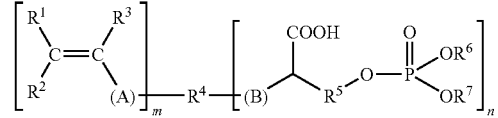

wherein $R^1$, $R^2$ and $R^3$ each independently are a hydrogen atom, a cyano group or a hydrocarbon group having 1 to 20 carbon atoms which may have a substituent; (A) and (B) are each any constituent unit; A is one selected from the group consisting of —CONH—, —COO—, —OCO—, —O—, —S—, —CH$_2$O—, —CH$_2$S—, —C$_6$H$_4$O—, —C$_6$H$_4$CONH—, —C$_6$H$_4$NHCO—, —C$_6$H$_4$COO—, —C$_6$H$_4$OCO— and —CONHCO—; B is one selected from the group consisting of —CONH—, —NHCO—, —COO— and —OCO—; m is an integer of from 1 to 3; n is an integer of from 1 to 3; R$^4$ is an organic group having 1 to 40 carbon atoms which may have a substituent; R$^5$ is a hydrocarbon group having 1 to 20 carbon atoms which may have a substituent; R$^6$ and R$^7$ each independently are a hydrogen atom, a hydrocarbon group having 1 to 20 carbon atoms which may have a substituent, or a metal atom.

In this embodiment, it is preferable that R$^1$ and R$^2$ each is a hydrogen atom and R$^3$ is a hydrogen atom or a methyl group. It is preferable that A is —CONH— or —COO—. It is preferable that B is —CONH—. It is preferable that R$^5$ is one selected from the group consisting of —CH$_2$-Ph-, —CH(CH$_3$)— and —CH$_2$—. Moreover, a composition containing the compound (I) is a preferable embodiment. It is preferable to contain the compound (I) and a polymerizable monomer (II) which is not the compound (I) and is copolymerizable with the compound (I). It is preferable that the polymerizable monomer (II) is a (meth)acrylate compound. It is preferable to contain a polymerization initiator (III) and it is preferable to contain a polymerization accelerator (IV). It is preferable to contain a filler (V). It is preferable to contain a solvent (VI) and the solvent (VI) preferably contains water (VII).

A preferable embodiment of the composition containing the compound (I) is a dental composition, and the composition is preferable especially as a primer, a bonding material, a cement or a composite resin.

A method by which a carboxylic acid (a1) represented by the following formula (2) is caused to undergo condensation reaction with an amine (b1) represented by the following formula (3) is provided as a preferable method for producing the compound (I),

[Chem. 2]

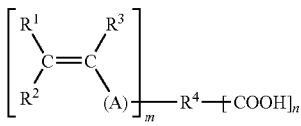
(2)

wherein R$^1$, R$^2$, R$^3$, R$^4$, (A), m and n are the same as those of the formula (1),

[Chem. 3]

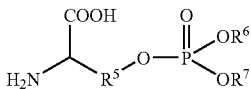
(3)

wherein R$^5$, R$^6$ and R$^7$ are the same as those of the formula (1).

In this embodiment, it is preferable that the carboxylic acid (a1) contains a (meth)acryl group, and it is preferable that the condensation agent used for the condensation reaction is a triazine-based condensing agent.

Moreover, it is preferable to provide a method for producing the compound (I), wherein it is obtained by causing an acid halide (a2) represented by the following formula (4) to undergo reaction with an amine (b1) represented by the following formula (3):

[Chem. 4]

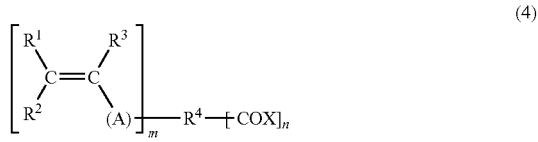
(4)

wherein R$^1$, R$^2$, R$^3$, R$^4$, (A), m and n are the same as those of the formula (1), and X is a halogen atom,

[Chem. 5]

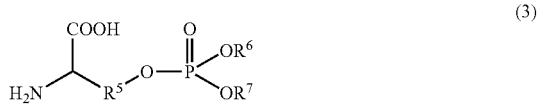
(3)

wherein R$^5$, R$^6$ and R$^7$ are the same as those of the formula (1).

In this embodiment, it is preferable that the acid halide (a2) contains a (meth)acryl group, and it is preferable that the amine (b1) is a phosphate of an amino acid. It is preferable that the amine (b1) is one selected from the group consisting of phosphoserine, phosphothreonine and phosphotyrosine.

The above-mentioned problems are solved also by providing a compound (VIII) represented by the following formula (5):

[Chem. 6]

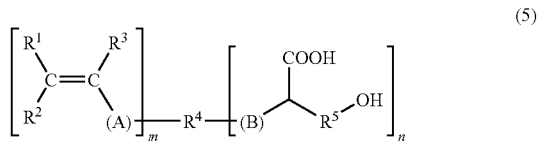
(5)

wherein R$^1$, R$^2$ and R$^3$ each independently are a hydrogen atom, a cyano group or a hydrocarbon group having 1 to 20 carbon atoms which may have a substituent; (A) and (B) are each any constituent unit; A is one selected from the group consisting of —CONH—, —COO—, —OCO—, —O—, —S—, —CH$_2$O—, —CH$_2$S—, —C$_6$H$_4$O—, —C$_6$H$_4$CONH—, —C$_6$H$_4$NHCO—, —C$_6$H$_4$COO—, —C$_6$H$_4$OCO— and —CONHCO—; B is one selected from the group consisting of —CONH—, —NHCO—, —COO— and —OCO—; m is an integer of from 1 to 3; n is an integer of from 1 to 3; R$^4$ is an organic group having 1 to 40 carbon atoms which may have a substituent; R$^5$ is a hydrocarbon group having 1 to 20 carbon atoms which may have a substituent.

Moreover, a method by which a carboxylic acid (a1) represented by the following formula (2) is caused to undergo condensation reaction with an amine (b2) represented by the following formula (6) is provided as a preferable method for producing the compound (VIII),

[Chem. 7]

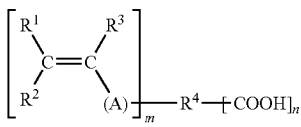

(2)

wherein $R^1$, $R^2$, $R^3$, $R^4$, (A), m and n are the same as those of the formula (5),

[Chem. 8]

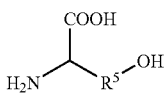

(6)

wherein $R^5$ is the same as that of the formula (2).

In this embodiment, it is preferable that the amine (b2) is an amino acid, and it is preferable that the amine (b2) is one selected from the group consisting of serine, threonine and tyrosine.

Moreover, the above-mentioned problems are solved also by providing a method for producing a polymerizable amide by which a carboxylic acid is caused to undergo condensation reaction with an amine to form an amide bond, wherein at least one of the carboxylic acid and the amine has a polymerizable group and the condensation reaction is performed using a triazine-based condensing agent (IX) represented by the following formula (7),

[Chem. 9]

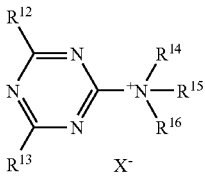

(7)

wherein $R^{12}$ and $R^{13}$ each independently are an alkoxy group or an alkyl group, $R^{14}$, $R^{15}$ and $R^{16}$ each independently are a hydrocarbon group having 1 to 20 carbon atoms which may have an oxygen atom, a nitrogen atom or a sulfur atom; X is a halogen atom, triflate, tosylate, mesylate or chloromethanesulfonate; $R^{14}$, $R^{15}$ and $R^{16}$ may link with each other to form a ring.

In this embodiment, it is preferable to obtain a polymerizable amide (X) represented by the following formula (10) by causing a carboxylic acid (a1) represented by the following formula (2) to undergo condensation reaction with an amine (b4) represented by the following formula (9),

[Chem. 10]

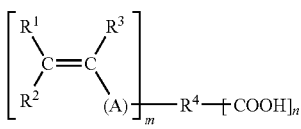

(2)

wherein $R^1$, $R^2$ and $R^3$ each independently are a hydrogen atom, a cyano group or a hydrocarbon group having 1 to 20 carbon atoms which may have a substituent; (A) is any constituent unit; A is one selected from the group consisting of —CONH—, —COO—, —OCO—, —O—, —S—, —CH$_2$O—, —CH$_2$S—, —C$_6$H$_4$O—, —C$_6$H$_4$CONH—, —C$_6$H$_4$NHCO—, —C$_6$H$_4$COO—, —C$_6$H$_4$OCO— and —CONHCO—; m is an integer of from 1 to 3; n is an integer of from 1 to 3; $R^4$ is an organic group having 1 to 40 carbon atoms which may have a substituent,

[Chem. 11]

$R^{18}$—NH$_2$    (9)

wherein $R^{18}$ is an organic group having 1 to 200 carbon atoms which may have a substituent,

[Chem. 12]

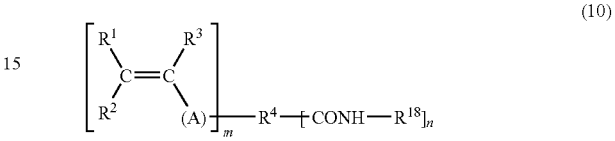

(10)

wherein $R^1$, $R^2$, $R^3$, $R^4$, $R^{18}$, (A), m and n are the same as those of the formula (2) and the formula (9).

Moreover, it is preferable that the carboxylic acid (a1) contains a (meth)acryloyl group. It is preferable that the amine (b4) is an amino acid, and it is preferable that the amine (b4) is a phosphate of an amino acid.

Furthermore, it is preferable to obtain a polymerizable amide (XI) represented by the following formula (13) by causing a carboxylic acid (a3) represented by the following formula (11) to undergo condensation reaction with an amine (b3) represented by the following formula (12),

[Chem. 13]

$R^{19}$—COOH    (11)

wherein $R^{19}$ is an organic group having 1 to 200 carbon atoms which may have a substituent,

[Chem. 14]

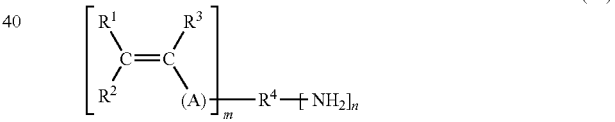

(12)

wherein $R^1$, $R^2$ and $R^3$ each independently are a hydrogen atom, a cyano group or a hydrocarbon group having 1 to 20 carbon atoms which may have a substituent; (A) is any constituent unit; A is one selected from the group consisting of —CONH—, —COO—, —OCO—, —O—, —S—, —CH$_2$O—, —CH$_2$S—, —C$_6$H$_4$O—, —C$_6$H$_4$CONH—, —C$_6$H$_4$NHCO—, —C$_6$H$_4$COO—, —C$_6$H$_4$OCO— and —CONHCO—; m is an integer of from 1 to 3; n is an integer of from 1 to 3; $R^4$ is an organic group having 1 to 40 carbon atoms which may have a substituent,

[Chem. 15]

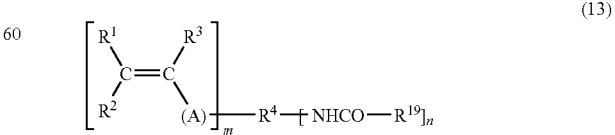

(13)

wherein $R^1$, $R^2$, $R^3$, $R^4$, $R^{19}$, (A), m and n are the same as those of the formula (11) and the formula (12).

Moreover, it is preferable that the amine (b3) contains a (meth)acryloyl group. It is preferable that the carboxylic acid (a3) is an amino acid, and it is preferable that the amine (a3) is a phosphate of an amino acid.

Furthermore, it is preferable that the triazine-based condensing agent (IX) be one represented by the following formula (8):

[Chem. 16]

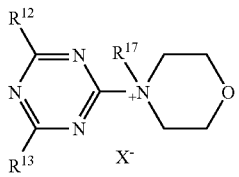
(8)

wherein $R^{12}$, $R^{13}$ and X are the same as those of the formula (7), and $R^{17}$ is a hydrocarbon group having 1 to 20 carbon atoms which may have a substituent.

Moreover, it is preferable that the reaction solvent to be used for the condensation reaction contains water, and it is also preferable that the reaction solvent to be used for the condensation reaction is a mixed solvent of water and alcohol.

Effect of the Invention

The new compound (I) of the present invention has a polymerizable group, a carboxyl group and a phosphoric acid group. When a composition containing the compound (I) of the present invention is used for a dental application, excellent bond strength is exhibited. Therefore, it is suitable as a dental composition and is suitable especially as a primer, a bonding material, a cement and a composite resin. The method for producing a polymerizable amide of the present invention can cause a condensation reaction of a carboxylic acid and an amine to proceed easily and is excellent in safety.

BEST MODE FOR CARRYING OUT THE INVENTION

The compound (I) of the present invention has a polymerizable group, a carboxyl group and a phosphoric acid group and a composition containing this compound is useful as a dental composition.

The compound (I) of the present invention is represented by the following formula (1) and has a polymerizable group. By having a polymerizable group, it becomes possible to undergo radical polymerization and also becomes possible to undergo copolymerization with other monomers. Examples of the polymerizable group include a (meth)acryl group, a (meth)acrylamide group, a vinyl(thio)ether group, an allyl (thio)ether group, a vinyl ester group and a styryl group. Among them, a (meth)acryl group or a (meth)acrylamide group is preferable from the viewpoint that radical polymerization is easy. While the compound (I) of the present invention is used preferably as a component of a dental composition, the polymerizable group may leave due to hydrolysis or the like because the inside of the oral cavity is under a wet environment. With consideration to the resistance to hydrolysis, it is more preferable to use to a (meth)acrylamide group as the polymerizable group. Furthermore, with consideration to the stimulativeness of a polymerizable group which has left to the living body, it is preferable to use a methacryl group or a methacrylamide group.

[Chem. 17]

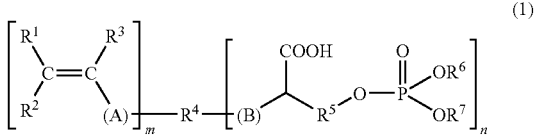
(1)

wherein $R^1$, $R^2$ and $R^3$ each independently are a hydrogen atom, a cyano group or a hydrocarbon group having 1 to 20 carbon atoms which may have a substituent; (A) and (B) are each any constituent unit; A is one selected from the group consisting of —CONH—, —COO—, —OCO—, —O—, —S—, —CH$_2$O—, —CH$_2$S—, —C$_6$H$_4$O—, —C$_6$H$_4$CONH—, —C$_6$H$_4$NHCO—, —C$_6$H$_4$COO—, —C$_6$H$_4$OCO— and —CONHCO—; B is one selected from the group consisting of —CONH—, —NHCO—, —COO— and —OCO—; m is an integer of from 1 to 3; n is an integer of from 1 to 3; $R^4$ is an organic group having 1 to 40 carbon atoms which may have a substituent; $R^5$ is a hydrocarbon group having 1 to 20 carbon atoms which may have a substituent; $R^6$ and $R^7$ each independently are a hydrogen atom, a hydrocarbon group having 1 to 20 carbon atoms which may have a substituent, or a metal atom.

In the formula (1), $R^1$, $R^2$ and $R^3$ each independently are a hydrogen atom, a cyano group or a hydrocarbon group having 1 to 20 carbon atoms which may have a substituent. Examples of the hydrocarbon group having 1 to 20 carbon atoms which may have a substituent include an alkyl group which may have a substituent, an alkenyl group which may have a substituent, a alkynyl group which may have a substituent, an aryl group which may have a substituent, an arylalkyl group which may have a substituent, an arylalkenyl group which may have a substituent, an arylalkynyl group which may have a substituent and a cycloalkyl group which may have a substituent.

In the present invention, the alkyl group which may have a substituent is a straight-chain or branched-chain alkyl group which may have a substituent. Examples of the alkyl group include a methyl group, an ethyl group, a n-propyl group, an isopropyl group, a n-butyl group, an isobutyl group, a sec-butyl group, a tert-butyl group, a n-pentyl, an isopentyl group, a neopentyl group, a tert-pentyl group, a n-hexyl group, an isohexyl group, a 2-ethylhexyl group, a n-heptyl group, a n-octyl group, a n-nonyl group and a n-decyl group.

In the present invention, the alkenyl group which may have a substituent is a straight-chain or branched-chain alkenyl group which may have a substituent. Examples of the alkenyl group include a vinyl group, an allyl group, a methylvinyl group, a propenyl group, a butenyl group, a pentenyl group, a hexenyl group, a cyclopropenyl group, a cyclobutenyl group, a cyclopentenyl group and a cyclohexyl group.

In the present invention, the alkynyl group which may have a substituent is a straight-chain or branched-chain alkynyl group which may have a substituent. Examples of the alkynyl group include ethynyl, 1-propynyl, 2-propynyl, 1-butynyl, 1-methyl-2-propynyl, 2-butynyl, 3-butynyl, 1-pentynyl, 1-ethyl-2-propynyl, 2-pentynyl, 3-pentynyl, 1-methyl-2-butynyl, 4-pentynyl, 1-methyl-3-butynyl, 2-methyl-3-butynyl, 1-hexynyl, 2-hexynyl, 1-ethyl-2-butynyl, 3-hexynyl, 1-methyl-2-pentynyl, 1-methyl-3-pentynyl, 4-methyl-1-pentynyl, 3-methyl-1-pentynyl, 5-hexynyl and 1-ethyl-3-butynyl.

In the present invention, the aryl group which may have a substituent is an aromatic hydrocarbon group which may have a substituent. Examples of the aryl group include a phenyl group, a naphthyl group, an anthryl group and a phenanthryl group.

In the present invention, the arylalkyl group which may have a substituent is an aryl-substituted straight-chain or branched-chain alkyl group which may have a substituent. Examples of the arylalkyl group include a benzyl group, a phenethyl group, a 3-phenylpropyl group, a trityl group, a 1-naphthylmethyl group, a 2-(1-naphthyl)ethyl group, a 2-(2-naphthyl)ethyl group and a 3-(2-naphthyl)propyl group.

In the present invention, the arylalkenyl group which may have a substituent is an aryl-substituted straight-chain or branched-chain alkenyl group which may have a substituent. Examples of the arylalkenyl group include a styryl group.

In the present invention, the arylalkynyl group which may have a substituent is an aryl-substituted straight-chain or branched-chain alkynyl group which may have a substituent. Examples of the arylalkynyl group include a phenylethynyl group.

In the present invention, the cycloalkyl group which may have a substituent is a cyclic alkyl group which may have a substituent. Examples of the cycloalkyl group include a cyclopropyl group, a cyclobutyl group, a cyclopentyl group, a cyclohexyl group, a cycloheptanyl group, a cyclooctanyl group, a cyclononanyl group, a cyclodecanyl group, a cycloundecanyl group and a cycldodecanyl group.

With respect to the formula (1), it is preferable that $R^1$ and $R^2$ are hydrogen atoms. This results in an advantage that the polymerizability is excellent. Moreover, with respect to the formula (1), it is preferable that $R^3$ is a hydrogen atom or a methyl group. This results in an advantage that the polymerizability is excellent. The case in which $R^1$ and $R^2$ are each a hydrogen atom and $R^3$ is a methyl group is advantageous in that, as described above, the compound of the present invention gives only a weak stimulation to a living body even if a polymerizable group has leaved from the compound due to an action of hydrolysis or the like.

In this embodiment, the number and the kind of the substituents which the hydrocarbon groups $R^1$, $R^2$ and $R^3$ have are not particularly limited. Embodiment in which there is a substituent between $R^1$, $R^2$ or $R^3$ and a double bond carbon are also included. It is preferable for $R^3$ that such a substituent is an ester bond. Examples of $R^3$ are the following:

[Chem. 18]

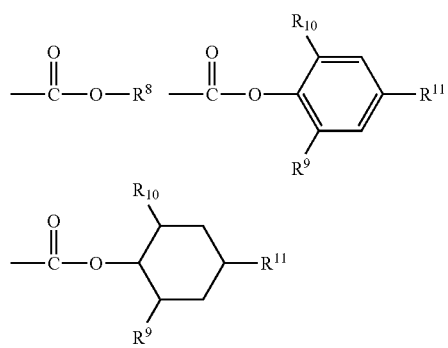

wherein $R^8$ is an alkyl group which may have a substituent, and $R^9$, $R^{10}$ and $R^{11}$ each independently are a hydrogen atom or an alkyl group which may have a substituent.

In the hydrocarbon groups having the ester bond shown above, the alkyl groups provided as examples in the description of $R^1$, $R^2$ and $R^3$ may be adopted for $R^8$; when $R^8$ is an alkyl group, it is preferable from the viewpoint of the polymerizability of the compound that $R^8$ is an alkyl group having 4 or less carbon atoms, and more preferably is a methyl group or an ethyl group. $R^9$, $R^{10}$ and $R^{11}$ each independently are a hydrogen atom or an alkyl group which may have a substituent. For the alkyl group which may have a substituent, those provided as examples in the description of $R^1$, $R^2$ and $R^3$ may be adopted. When $R^9$, $R^{10}$ and $R^{11}$ are alkyl groups, it is preferable, from the viewpoint of the polymerizability of the compound, that they are alkyl groups having 4 or less carbon atoms, and more preferably are a methyl group, an ethyl group or a tert-butyl group.

In the formula (1), (A) is an arbitrary constituent unit. A is one selected from the group consisting of —CONH—, —COO—, —OCO—, —O—, —S—, —CH$_2$O—, —CH$_2$S—, —C$_6$H$_4$O—, —C$_6$H$_4$CONH—, —C$_6$H$_4$NHCO—, —C$_6$H$_4$COO—, —C$_6$H$_4$OCO— and —CONHCO—. From the viewpoint that radical polymerization easily occurs, it is preferable that A is —CONH— or —COO—. Moreover, when the compound of the present invention is used for an embodiment in which the resistance to hydrolysis is particularly required, it is preferable that A is —CONH— or —CH$_2$O—.

In the formula (1), (B) is an arbitrary constituent unit. B is one selected from the group consisting of —CONH—, —NHCO—, —COO— and —OCO—. When the compound of the present invention is used for an embodiment in which the resistance to hydrolysis is particularly required, it is preferable that B is —CONH—.

In the formula (1), $R^4$ is an organic group having 1 to 40 carbon atoms which may have a substituent, wherein the organic group is a 2- to 6-valent substituent. The organic group may contain, in its structure, a bond other than a carbon-carbon bond, such as an ether bond, an ester bond, an amide bond, a sulfonyl bond, a urethane bond and a thioether bond. Moreover, it also may contain an aromatic ring, a double bond, a triple bond or an alicyclic hydrocarbon group. Furthermore, it also may have a substituent, such as a halogen atom, a hydroxyl group, an amino group, a cyano group and a nitro group. Specific examples of such organic groups include the following, wherein i, j, k, l, m, n, o, p, q, r, s and t in the formulae are positive integers.

[Chem. 19]

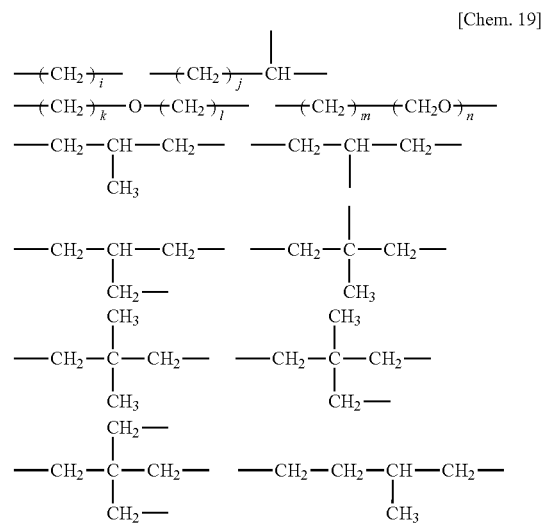

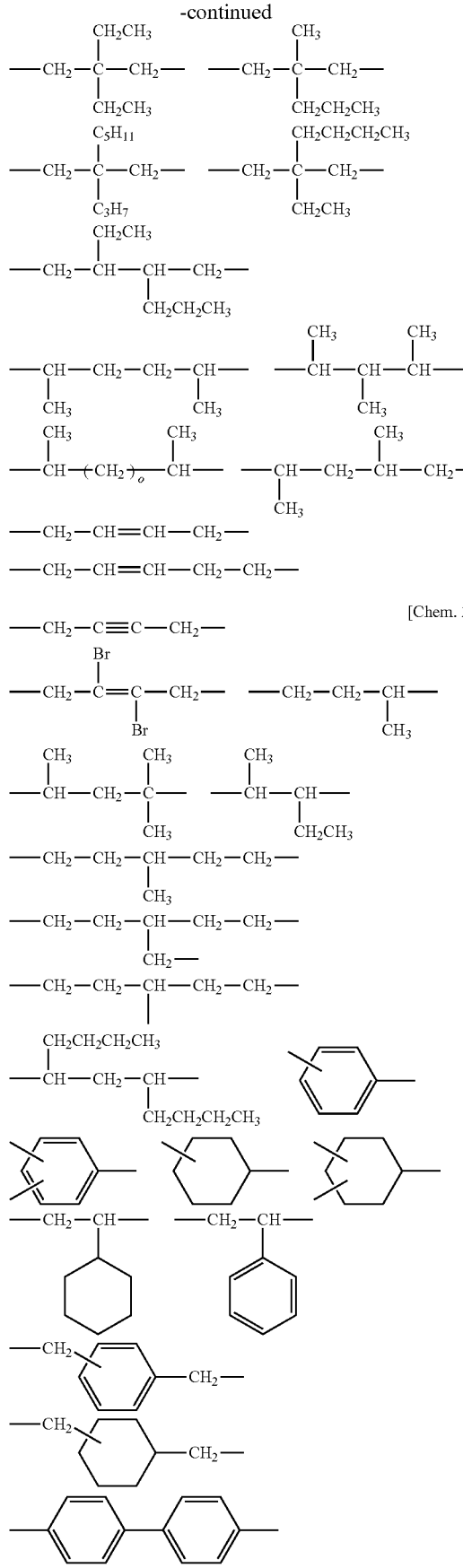

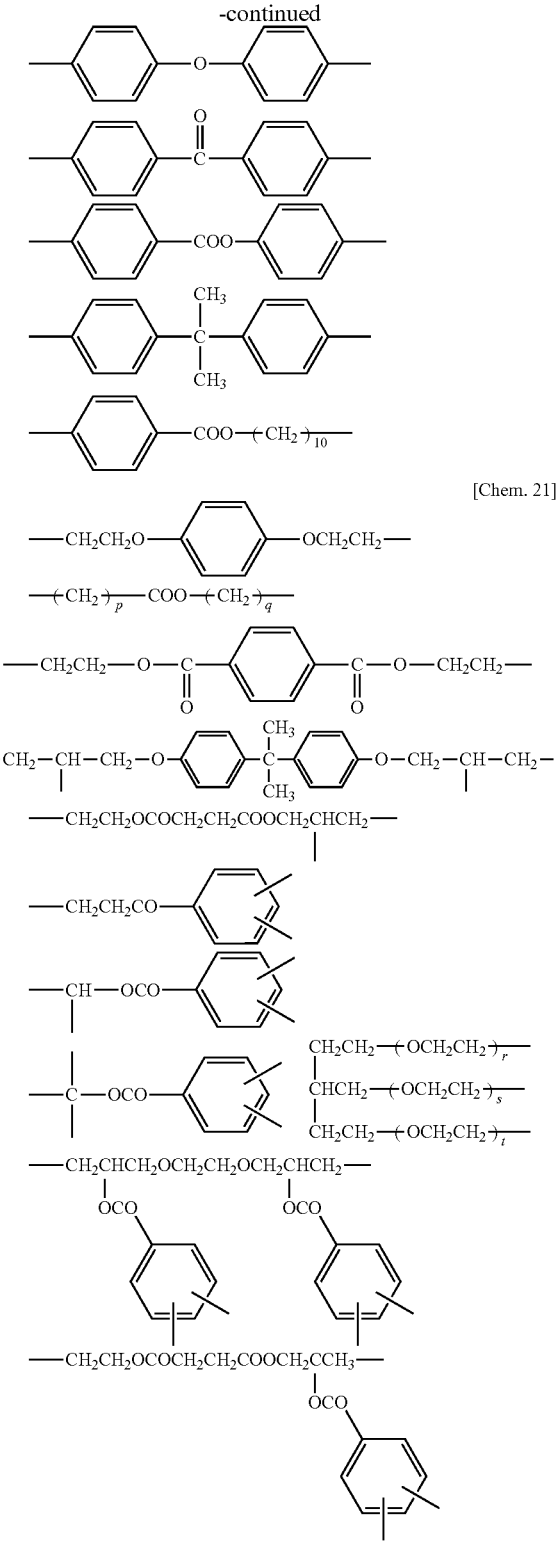

The mechanism in which an adhesive properties is developed in a case that a compound containing an acidic group and a polymerizable group and also having an organic group as a spacer is used as an adhesive is not necessarily clear. Generally, it is believed that the development of adhesive properties needs that an acidic group chemically bonds to an object to be adhered and then a polymerizable group (co)

polymerizes to form a coating. It is believed to be important, for the purpose of obtaining a excellent adhesive properties, that a compound having an acidic group and a polymerizable group is arranged regularly when it bonds to the object, so that it makes an effect densely to a surface for adhesion. The selection of the organic group to be used as a spacer is important for the purpose of arranging the compound regularly.

From such a viewpoint, the organic group is preferably a straight-chain aliphatic hydrocarbon group. One example of such a substituent is an alkylene group. From the viewpoint of increasing the adhesive properties, it is preferable that the acidic group and the polymerizable group is located at some distance from each other. The lower limit of the number of the carbon atoms in $R^4$ is preferably 4 or more, and more preferably 6 or more. Furthermore, a preferable embodiment of the compound (I) of the present invention is a dental composition. In the use for such an application, the lower limit of the number of the carbon atoms in $R^4$ is even more preferably 7 or more, and particularly preferably 8 or more because the inside of the oral cavity is under a wet environment. By determining the number of the carbon atoms in $R^4$ within such a range, the hydrophobicity of the compound as a whole increases, so that it becomes resistant to hydrolysis even under a wet environment, for example, in the oral cavity and, as a result, it becomes possible to maintain a high adhesive properties for a longer period of time.

Moreover, when a dental composition is used and is adhered to a tooth structure, it becomes necessary to provide a decalcification step by which the tooth structure surface is dissolved with an acidic component. There, however, is an advantage that the adjustment of the number of the carbon atoms of $R^4$ to within the foregoing range reduces the solubility to water of the calcium salt of the compound (I) generated in the decalcification step, so that the adhesive properties further increases. The upper limit of the number of the carbon atoms of $R^4$ is not particularly limited. If, however, the number of the carbon atoms reaches a certain level, there is a tendency that no further effect on improvement in adhesive properties is developed even if the number of the carbon atoms is further increased. For this reason, from the viewpoint that raw materials can be obtained easily, the upper limit of the number of the carbon atoms in $R^4$ is preferably 30 or less, more preferably 20 or less, even more preferably 18 or less, and particularly preferably 16 or less.

In the formula (1), $R^5$ is a hydrocarbon group having 1 to 20 carbon atoms which may have a substituent, and the substituents provided as examples above may be employed. In the formula (1), it is preferable that $R^5$ is one selected from the group consisting of —$CH_2$-Ph-, —$CH(CH_3)$— and —$CH_2$—. Because of the fact that $R^5$ is one selected from among such substituents, the arrangement of the carboxyl group and the phosphoric acid group in the molecule comes into a condition suitable for the interaction with calcium ion, and this contributes to the improvement in adhesive properties. From this viewpoint, $R^5$ is more preferably one selected from the group consisting of —$CH(CH_3)$— and —$CH_2$—, and is even more preferably composed of —$CH_2$—. With respect to $R^5$, it is preferable that the compound (I) of the present invention is produced using a phosphate of an amino acid like phosphoserine, phosphothreonine or phosphotyrosine as one of the raw materials. When phosphoserine is used, $R^5$ is —$CH_2$—. When phosphothreonine is used, $R^5$ is —$CH(CH_3)$—. When phosphotyrosine is used, $R^5$ is —$CH_2$-Ph-.

In the formula (1), $R^6$ and $R^7$ each independently are a hydrogen atom, a hydrocarbon group having 1 to 20 carbon atoms which may have a substituent, or a metal atom. For the hydrocarbon group having 1 to 20 carbon atoms which may have a substituent, the substituents provided as examples in the description of $R^1$, $R^2$ and $R^3$ may be adopted. The metal atom is preferably a metal atom of Group 1 or Group 2 of the periodic table. Specific examples include sodium, potassium, calcium and magnesium. From the viewpoint of the acidity of the compound (I), it is preferably that $R^6$ and $R^7$ are each a hydrogen atom or a hydrocarbon group having 1 to 6 carbon atoms, more preferably are each a hydrogen atom, a methyl group, an ethyl group or a phenyl group, and even more preferably are hydrogen atoms.

In the formula (1), m is an integer of from 1 to 3 and n is an integer of from 1 to 3. As described above, in order to regularly arrange the compound (I) which has bonded to an object to be adhered, it is preferable that m=1 and n=1. The case where m=1 and n=1 is beneficial also in that the process required by the synthesis becomes shorter, leading to an advantage in cost. On the other hand, in the case that there is a wish to increase the number of points of action at which it chemically interacts with the object, it is preferable that n is 2 or 3. This is effective particularly when the object is metal or porcelain. Furthermore, also when there is a wish to increase the coating film strength by imparting crosslinkability to the compound (I), it is preferable that m is 2 or 3. As described above, the proper values of m and n differ according to the embodiments and may be selected arbitrarily depending on the embodiment.

The method for producing the compound (I) of the present invention is not particularly limited. Preferably, it can be obtained by causing a carboxylic acid (a1) represented by the following formula (2) to undergo condensation reaction with an amine (b1) represented by the following formula (3).

[Chem. 22]

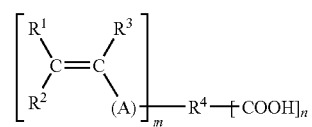

(2)

wherein $R^1$, $R^2$, $R^3$, $R^4$, (A), m and n are the same as those of the formula (1),

[Chem. 23]

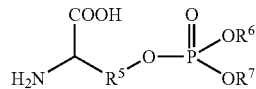

(3)

wherein $R^5$, $R^6$ and $R^7$ are the same as those of the formula (1).

The carboxylic acid (a1) represented by the formula (2) contains a polymerizable group. The polymerizable group is not particularly limited, and examples thereof include a (meth)acryl group, a (meth)acrylamide group, a vinyl(thio)ether group, an allyl(thio)ether group, a vinyl ester group and a styryl group. Among them, a (meth) acryl group or a (meth) acrylamide group is preferable from the viewpoint that radical polymerization is easy. While the compound (I) of the present invention is used preferably as a component of a dental composition, the polymerizable group may leave due to hydrolysis or the like because the inside of the oral cavity is under a wet environment. With consideration to the resistance to hydrolysis, it is more preferable to use to a (meth)acrylamide group as the polymerizable group. Furthermore, with consideration to the stimulativeness of a polymerizable group which has left to the living body, it is preferable to use a methacryl group or a methacrylamide group.

The amine (b1) represented by the formula (3) is preferably a phosphate of an amino acid. The phosphate of an amino acid is a substance in which a phosphoric acid group is attached to a hydroxyl group of an amino acid having the hydroxyl group. The fact that the amine (b1) is a phosphate of an amino acid causes the amino group of the amine (b1) and the carboxyl group of the carboxylic acid (a1) to undergo condensation reaction together, making the resulting compound (I) of the present invention have both a carboxyl group and a phosphoric acid group.

It is preferable that the amine (b1) to be used in the method for producing the compound (I) of the present invention is one selected from the group consisting of phosphoserine, phosphothreonine and phosphotyrosine. Amino acids are present extensively in the living body. In many cases, an amino acid having a hydroxyl group is phosphorylated in the living body to exist in the form of a phosphate of the amino acid. Therefore, even in the case that the compound (I) of the present invention was applied in the living body for a long period of time so that a decomposed product has been formed by the action of hydrolysis or the like, the use of the above-mentioned type of phosphate of an amino acid as the amine (b1) leads to the release, caused by decomposition, of a substance inherently contained in the living body. Therefore, it is of great merit from the viewpoint of safety. When $R^5$ is —$CH_2$— and $R^6$ and $R^7$ are each a hydrogen atom in the formula (3), it is phosphoserine; when $R^5$ is —$CH(CH_3)$— and $R^6$ and $R^7$ are each a hydrogen atom in the formula (3), it is phosphothreonine; and when $R^5$ is —$CH_2$-Ph- and $R^6$ and $R^7$ are each a hydrogen atom in the formula (3), it is phosphotyrosine.

While the condensing agent to be used in the method for producing the compound (I) of the present invention is not particularly limited, it is preferably a triazine-based condensing agent. Because of the use of a triazine-type condensing agent, it is possible to carry out condensation reaction under mild conditions, and the safety is good because, unlike carbodiimide-based condensing agents, such an agent causes no skin irritation.

Examples of such a triazine-based condensing agent include the substances represented by the following formula (7):

[Chem. 24]

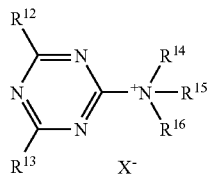

(7)

wherein $R^{12}$ and $R^{13}$ each independently are an alkoxy group or an alkyl group, $R^{14}$, $R^{15}$ and $R^{16}$ each independently are a hydrocarbon group having 1 to 20 carbon atoms which may have an oxygen atom, a nitrogen atom or a sulfur atom; X is a halogen atom, triflate, tosylate, mesylate or chloromethanesulfonate; $R^{14}$, $R^{15}$ and $R^{16}$ may link with each other to form a ring.

In the formula (7), the substituents $R^{12}$ and $R^{13}$ attached to a triazine ring are each independently an alkoxy group or an alkyl group. The alkoxy group includes straight-chain or branched-chain alkoxy groups having 1 to 20 carbon atoms, and examples thereof include a methoxy group, an ethoxy group, a n-propoxy, an isopropoxy group, a n-butoxy group, an isobutoxy group, a sec-butoxy group, a tert-butoxy group, a n-pentyloxy group, an isopentyloxy group, a neopentyloxy group, a n-hexyloxy group, an isohexyloxy group, a 2-ethylhexyloxy group, a n-heptyloxy group, a n-octyloxy group, a n-nonyloxy group and a n-decyloxy group. From the viewpoint of the reactivity of a condensing agent to be obtained, a methoxy group, an ethoxy group or an isopropoxy group is preferable, and a methoxy group is more preferable. The alkyl groups provided as examples in the foregoing descriptions about $R^1$, $R^2$ and $R^3$ may be adopted as the alkyl group. From the viewpoint of the reactivity of a condensing agent to be obtained, a methyl group, an ethyl group of a tert-butyl group is preferable. Among them, it is preferable that each of the substituents $R^{12}$ and $R^{13}$ is a methoxy group because of balance between the easiness of production and the reactivity of the condensing agent.

In the formula (7), $R^{14}$, $R^{15}$ and $R^{16}$ each independently are a hydrocarbon group having 1 to 20 carbon atoms which may have an oxygen atom, a nitrogen atom or a sulfur atom, and preferably are a hydrocarbon group having from 1 to 10 carbon atoms. $R^{14}$, $R^{15}$ and $R^{16}$ may link with each other to form a ring. Adjacent substituents may link to form a ring, or alternatively, substituents distant from each other may link to form a ring.

In the formula (7), X is a halogen atom, triflate, tosylate, mesylate or chloromethanesulfonate. The triazine-based condensing agent is preferably one resulting from a reaction of a triazine ring to which X is attached with a tertiary amine. X will leave through such a reaction to exist as a counter anion in the triazine-based condensing agent. It is preferable that the X is a functional group which is to be used a leaving group, and a halogen atom or triflate is preferably used. The halogen atom includes fluorine, chlorine, bromine, and iodine. Chlorine is preferably adopted in view of the balance between the reactivity and the storage stability of the condensing agent.

The triazine-based condensing agent represented by the formula (7) preferably has a morpholine ring as shown in the following formula (8). Thus, the condensing agent comes to have a proper reactivity and also comes to have an increased crystallinity, so that it can be handled in the form of a powder. Therefore, a great merit can be obtained with respect to purification, storage stability, handling efficiency, and the like.

[Chem. 25]

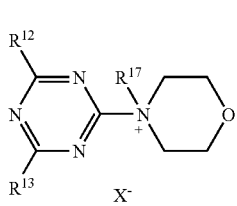

(8)

wherein $R^{12}$, $R^{13}$ and X are the same as those of the formula (7), and $R^{17}$ is a hydrocarbon group having 1 to 20 carbon atoms which may have a substituent.

The $R^{17}$ attached to the N of the morpholine ring in the formula (8) is a hydrocarbon group having 1 to 20 carbon atoms which may have a substituent, and the $R^{17}$ is preferably an alkyl group which may have a substituent. The alkyl groups provided as examples in the foregoing descriptions about $R^1$, $R^2$ and $R^3$ may be adopted as the alkyl group. From a viewpoint of the easiness in the production of a condensing agent and the storage stability of a resulting condensing agent, the alkyl group is preferably an alkyl group having 1 to 4 carbon atoms, and more preferably a methyl group.

In the production method of compound (I) of the present invention, while the used amount of the triazine-based condensing agent is not particularly limited, it is preferable to use the triazine-based condensing agents at an amount of 0.5 to 2 mol relative to 1 mol of the carboxylic acid (a1) represented by the formula (2), which is a raw material. If the used amount of the triazine-based condensing agent is less than 0.5 mol, a condensation reaction may become difficult to proceed and the reaction yield may decrease. The used amount of the triazine-based condensing agent is more preferably 0.6 mol or more, even more preferably 0.7 mol or more, and particularly preferably 0.8 mol or more relative to 1 mol of the carboxylic acid (a1). On the other hand, if the used amount of the triazine-based condensing agent exceeds 2 mol relative to 1 mol of the carboxylic acid (a1), the reactivity may become so high that an amino group-containing compound (specifically, amine (b1)) may further react with a carboxyl group in the molecule of the compound (I) of the present invention and, as a result, the reaction yield may decrease. From such a viewpoint, the used amount of the triazine-based condensing agent is more preferably 1.8 mol or less, even more preferably 1.6 mol or less, and particularly preferably 1.4 mol or less relative to 1 mol of the carboxylic acid (a1).

In the method for producing the compound (I) of the present invention, while the method of causing the carboxylic acid and the amine to react is not particularly limited, it is preferable to cause them to react while stirring them. At this time, the timing of adding the triazine-based condensing agent, the carboxylic acid and the amine is not particularly limited. It is permissible to add them simultaneously to the reaction system and then mix them. It is also permissible to add them sequentially. In the use of a carbodiimide-based condensing agent like DCC, it is necessary to cause a carboxylic acid and a condensing agent to react together first and then add an amine because the condensing agent can react with both the carboxylic acid and the amine. The yield may decrease depending upon the timing of the addition of the amine. On the other hand, the triazine-based condensing agent to be used in the present invention is advantageous in that no consideration about the timing of its addition is needed because it reacts selectively with only a carboxylic acid and does not react with an amine, and therefore the compound (I) of the present invention can be obtained at a high yield. It is preferable that the carboxylic acid and the amine have been dissolved completely when the triazine-based condensing agent is added. This leads to rapid proceeding of a condensation reaction.

In the production method of the present invention, an embodiment in which a triazine-based condensing agent is added to a reaction system so as to cause a carboxylic acid and an amine to react together is available. Also an embodiment in which a triazine-based condensing agent is generated in a reaction system by adding a triazine compound such as 2-chloro-4,6-dimethoxy-1,3,5-triazine (CDMT), and a tertiary amine such as dimethylglycine ethyl ester (DMGE), into the reaction system and then a carboxylic acid and an amine are caused to react together is available. The addition of the tertiary amine to the triazine compound causes the condensation reaction to proceed rapidly.

While the used amount of the triazine compound used in the preparation of the triazine-based condensing agent is not particularly limited, it is preferable to use the triazine compound at an amount of 0.5 to 2 mol, more preferably at an amount of 0.7 to 1.5 mol relative to 1 mol of the carboxylic acid. While the used amount of the tertiary amine is not particularly limited, the tertiary amine serves as a catalyst in the reaction system and, therefore, it is not necessary to add the amine at an equimolar amount with the triazine compound. For this reason, in view of the merit in cost, it is preferable to use a tertiary amine at an amount of 0.05 to 0.5 mol, more preferably at an amount of 0.1 to 0.3 mol relative to 1 mol of the triazine compound.

The reaction temperature used in the production of the compound (I) of the present invention by using the triazine-based condensing agent is not particularly limited, and it may be adjusted appropriately depending upon the kind of the carboxylic acid or the amine to be used and the reaction solvent. The use of the triazine-based condensing agent is advantageous in that it is possible to cause a reaction to proceed smoothly even at room temperature and, therefore, it is possible to carryout the reaction under very mild conditions. With respect to the reaction temperature, a temperature of 10 to 60° C. is ordinarily used, and the reaction temperature preferably is 15 to 45° C.

The reaction time in the production of the compound (I) of the present invention is not particularly limited, and it may be adjusted appropriately depending upon the kind of the carboxylic acid or the amine to be used and the reaction solvent. It is ordinarily 10 minutes to 24 hours, and preferably 20 minutes to 16 hours.

In the method for producing the compound (I) of the present invention by using the triazine-based condensing agent, it is preferable to carry out the reaction under a neutral condition. The reaction may not proceed under acidic conditions. Under basic conditions, an amide bond in the resulting compound (I) of the present invention may be hydrolyzed. Therefore, in the method for producing the compound (I) of the present invention by using the triazine-based condensing agent, the pH of the reaction system is preferably 6.5 to 8, more preferably 7 to 8, and particularly preferably 7 to 7.6.

The reaction solvent to be used in the method for producing the compound (I) of the present invention is not particularly limited. When the triazine-based condensing agent is used, however, it is preferable that the reaction solvent contains water. Usually, in condensation reactions by which an ester bond or an amide bond is formed, water is a substance which is to be removed. If water is present, the reaction efficiency often decreases. On the other hand, in the method for producing the compound (I) of the present invention, the reaction proceeds without decrease in reaction efficiency. Moreover, amidation can be accomplished by the use of a compound which is hardly-soluble in organic solvents other than water, e.g., an amino acid having a phosphoric acid group and a reaction advances with no decrease in reaction efficiency, and it also excels in the field of environmental protection.

The organic solvent to be used as a reaction solvent includes halogen-containing solvents such as methylene chloride and chloroform; hydrocarbon solvents such as hexane and toluene; ester solvents such as ethyl acetate; ether solvents such as diethyl ether, diisopropyl ether and tetrahydrofuran; acetonitrile; dimethylformamide (DMF); dimethyl sulfoxide (DMSO); and alcohol solvents such as methanol, ethanol and isopropyl alcohol. Among them, at least one selected from the group consisting of ester solvents, ether solvents and alcohol solvents is preferred, and particularly the use of an alcohol solvent is preferred from the viewpoint that it is possible to cause the triazine-based condensing agent to exist with stability. It is known that it is more difficult to use alcohol than water because when alcohol is used as a reaction solvent, a competitive reaction where the solvent alcohol and a carboxylic acid produce an ester occurs. In the method for producing the compound (I) of the present invention, alcohol can be used as a reaction solvent if the triazine-based condensing agent is used, because the amide formation is extremely higher in selectivity than the ester formation. When alcohol is used, it is more useful than organic solvents which are relatively high in boiling point, like DMF and DMSO, because of the facts that a variety of compounds are soluble therein in comparison to water, the solvent can be removed easily because of its low boiling point, or it is less expensive, or the like.

The alcohol to be used for the method for producing the compound (I) of the present invention is not particularly limited and includes aliphatic alcohols such as methanol, ethanol, n-propanol, 2-propanol, n-butanol, 2-butanol, cyclopropanol, cyclopentanol and cyclohexanol; and aromatic alcohol such as phenol, m-cresol and benzyl alcohol. These alcohols may be used singly or in combination of two or more of them. In the case that a mixed solvent of water and an alcohol is used as a reaction solvent, it is preferable from the viewpoint of the miscibility with water to use at least one selected from the group consisting of methanol, ethanol, n-propanol and 2-propanol. The use of methanol is particularly preferred from the viewpoint that it easily dissolves a carboxylic acid, a raw material, and the solvent can be removed easily due to its low boiling point.

In the case that the triazine-based condensing agent is used in the method for producing the compound (I) of the present invention, it is preferable that the reaction solvent is a mixed solvent of water and an alcohol. It can be used with an appropriate adjustment of the mixed ratio of the alcohol to the water depending upon the solubility of the reactants, the mixed ratio of the alcohol to the water (alcohol/water) is preferably 9/1 to 1/9, more preferably 8/2 to 2/8, and even more preferably 8/2 to 5/5.

In the method for producing the compound (I) of the present invention, the reaction proceeds in two steps as illustrated with a reaction formula below by taking as an example a case in which the triazine-based condensing agent represented by the formula (8), the carboxylic acid represented by the formula (2) and the amine represented by the formula (3) are used, m=1, n=1 and X is a chlorine atom. That is, in a first stage, a carboxylic acid represented by formula (2a) is attached to a triazine ring represented by formula (8a), so that an ester intermediate represented by formula (2b) is generated, and simultaneously a morpholine represented by formula (8b) and hydrochloric acid are generated. Subsequently, in a second stage, an amine represented by the formula (3) acts on the ester intermediate represented by the formula (2b), so that the compound (I) of the present invention represented by formula (1a) is obtained and simultaneously a hydroxytriazine represented by formula (8c) is generated. While a neutralizing agent or the like may be added in order to neutralize the hydrochloric acid produced at that reaction, it is not necessary to add a neutralizing agent and the reaction proceeds well because the hydrochloric acid is captured by the morpholine represented by the formula (8b) which was generated in the first stage.

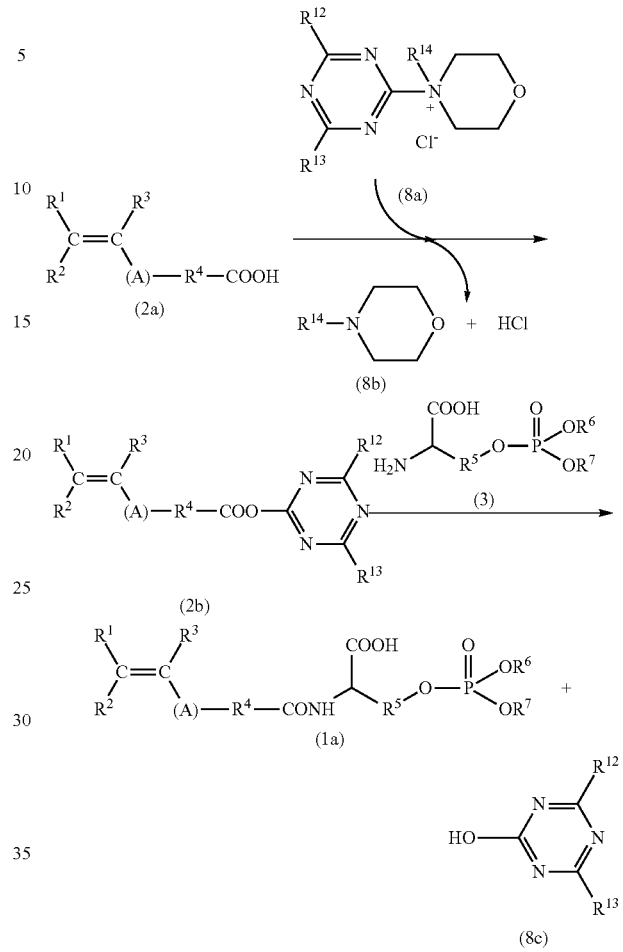

[Chem. 26]

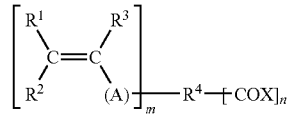

With regard to the method for producing the compound (I) of the present invention, the compound (I) can be also obtained by causing an acid halide (a2) represented by the following formula (4) to react with an amine (b1) represented by the following formula (3).

[Chem. 27]

$$\left[ \begin{array}{c} R^1 \\ R^2 \end{array} C = C \begin{array}{c} R^3 \\ (A) \end{array} \right]_m R^4 \mbox{\textemdash} [COX]_n \quad (4)$$

wherein $R^1$, $R^2$, $R^3$, $R^4$, (A), m and n are the same as those of the formula (1), and X is a halogen atom,

[Chem. 28]

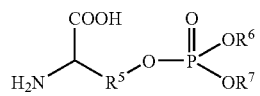

wherein $R^5$, $R^6$ and $R^7$ are the same as those of the formula (1).

In the formula (4), X is a halogen atom and the halogen atom includes fluorine, chlorine, bromine, and iodine. From the viewpoint of the stability and the easiness in preparation of the acid halide (a2), chlorine is preferably adopted.

The acid halide (a2) represented by the formula (4) contains a polymerizable group. The polymerizable group is not particularly limited, and examples thereof include a (meth) acryl group, a (meth)acrylamide group, a vinyl(thio)ether group, an allyl(thio)ether group, a vinyl ester group and a styryl group. Among them, a (meth)acryl group or a (meth) acrylamide group is preferable from the viewpoint that radical polymerization is easy. While the compound (I) of the present invention is used preferably as a component of a dental composition, the polymerizable group may leave due to hydrolysis or the like because the inside of the oral cavity is under a wet environment. With consideration to the resistance to hydrolysis, it is more preferable to use to a (meth) acrylamide group as the polymerizable group. Furthermore, with consideration to the stimulativeness of a polymerizable group which has left to the living body, it is preferable to use a methacryl group or a methacrylamide group.

While the method by which the acid halide (a2) represented by the formula (4) and the amine (b1) represented by the formula (3) are caused to react together is not particularly limited, Schotten-Baumann reaction, which is conducted in the presence of alkali, can be employed. In this method, sodium hydroxide or the like is added to a reaction system in which an amine (b1) has been dissolved uniformly to make the reaction system have an alkaline pH, and then an acid halide (a2) is dropped to this. The acidification of the reaction solution which is carried out after the dropping results in the formation of a precipitate, and the precipitate is purified to give the compound (I) of the present invention. By carrying out the reaction by this method, it is possible to obtain the compound (I) of the present invention under mild conditions.

While the used amounts of the acid halide (a2) and the amine (b1) are not particularly limited, it is preferable to use 0.5 to 3 mol, more preferably 0.6 to 2 mol of the acid halide (a2) relative to 1 mol of the amine (b1). The used amounts depend on the easiness with which the acid halide (a2) and the amine (b1) are obtained. That is, if it is more difficult to obtain the acid halide (a2) than the amine (b1), it is more economically advantageous to adjust the used amount of the acid halide (a2) to 1 mol or less relative to 1 mol of the amine (b1) and thereby cause all the acid halide (a2) to react. The converse is true if the amine (b1) is more difficult to obtain.

The reaction temperature at which the acid halide (a2) and the amine (b1) are caused to react is not particularly limited. It is preferable to employ a production method by which the acid halide (a2) is dropped slowly while a solution containing the amine (b1) is stirred. The acid halide (a2) may be dropped either with or without being diluted with a solvent. While the temperature at which the dropping is carried out is not particularly limited, it is preferably −10 to 10° C., and more preferably −5 to 5° C. After the completion of the dropping, stirring is continued until the reaction is completed. The reaction temperature employed in this course is normally 10 to 60° C., and preferably 15 to 45° C.

While the reaction time during which the acid halide (a2) and the amine (b1) are caused to react is not particularly limited, it is normally 1 to 6 hours, and preferably 2 to 4 hours. The maintenance of the pH of the reaction system is important for this reaction. There is a possibility that the reaction fails to proceed due to the decrease in the reactivity of the amino group of the amine (b1) under acidic conditions. On the other hand, if the reaction system is excessively basic, there is a possibility that the amide bond in the resulting compound (I) of the present invention is hydrolyzed. For this reason, in practicing this reaction, the pH of the reaction system is preferably 8 to 9. The pH in the system decreases to shift to the acidic side with the proceeding of the dropping of the acid halide (a2) or the proceeding of the reaction. Therefore, it is preferable to adjust the pH of the reaction system appropriately by adding a basic solution while monitoring the pH in the system by a pH meter or the like. While the basic solution is not particularly limited, a solution of sodium hydroxide or potassium hydroxide is preferably used.

While the compound (I) of the present invention has at least one polymerizable group, at least one phosphoric acid group and at least one carboxyl group, it can be produced by introducing a phosphoric acid group into a compound (VIII) represented by the following formula (5). This compound (VIII) is a novel compound.

[Chem. 29]

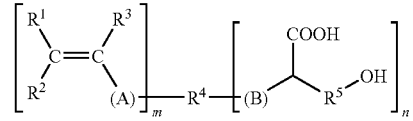

(5)

wherein $R^1$, $R^2$ and $R^3$ each independently are a hydrogen atom, a cyano group or a hydrocarbon group having 1 to 20 carbon atoms which may have a substituent; (A) and (B) are each any constituent unit; A is one selected from among —CONH—, —COO—, —OCO—, —O—, —S—, —CH$_2$O—, —CH$_2$S—, —C$_6$H$_4$O—, —C$_6$H$_4$CONH—, —C$_6$H$_4$NHCO—, —C$_6$H$_4$COO—, —C$_6$H$_4$OCO— and —CONHCO—; B is one selected from among —CONH—, —NHCO—, —COO— and —OCO—; m is an integer of from 1 to 3; n is an integer of from 1 to 3; $R^4$ is an organic group having 1 to 40 carbon atoms which may have a substituent, and $R^5$ is a hydrocarbon group having 1 to 20 carbon atoms which may have a substituent.

In the compound (VIII) represented by the formula (5), $R^1$, $R^2$, $R^3$, $R^4$, $R^5$, (A), (B), m and n are the same as in the formula (1), and those provided in the description of the formula (1) are employed. The compound (VIII) represented by the formula (5) has at least one polymerizable group, at least one hydroxy group, and at least one carboxyl group. The fact that the compound (VIII) has a polymerizable group enables the compound to undergo radical polymerization and also enables it to undergo copolymerization with other monomers. Examples of the polymerizable group include a (meth)acryl group, a (meth)acrylamide group, a vinyl(thio)ether group, an allyl(thio)ether group, a vinyl ester group and a styryl group. Among them, a (meth)acryl group or a (meth)acrylamide group is preferable from the viewpoint that radical polymerization is easy. While the compound (I) of the present invention is used preferably as a component of a dental composition, the polymerizable group may leave due to hydrolysis or the like because the inside of the oral cavity is under a wet environment. With consideration to the resistance to hydrolysis, it is more preferable to use to a (meth)acrylamide group as the polymerizable group. Furthermore, with consideration to the stimulativeness of a polymerizable group which has left to the living body, it is preferable to use a methacryl group or a methacrylamide group. When the compound (VIII) has a hydroxyl group, it is possible to obtain the compound (I) of the present invention by causing the group to undergo dehydration condensation with a phosphoric acid group. Because the compound (VIII) has a carboxyl group, it is possible to decalcify the tooth structure when the resulting compound (I) is used in the form of a dental composition and, therefore, it can be used for applications of adhesives such as primers and bonding materials.

While the method for producing the compound (VIII) represented by the formula (5) is not particularly limited, it can be obtained by causing a carboxylic acid (a1) represented by the following formula (2) to undergo condensation reaction with an amine (b2) represented by the following formula (6).

[Chem. 30]

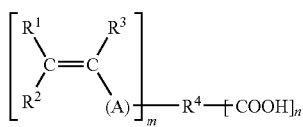
(2)

wherein $R^1$, $R^2$, $R^3$, $R^4$, (A), m and n are the same as those of the formula (1),

[Chem. 31]

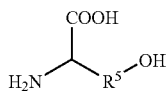
(6)

wherein $R^5$ is the same as that of the formula (5).

In the carboxylic acid (a1) represented by the formula (2), polymerizable groups which are the same as those provided in the description about the formula (1) are preferably employed. The amine (b2) represented by the formula (6) is preferably an amino acid, and particularly preferably an amino acid having a hydroxyl group. Because the amine (b2) is an amino acid, the compound (VIII) which results from a condensation reaction of the amino group of the amine (b2) and the carboxyl group of the carboxylic acid (a1) comes to have both a carboxyl group and a hydroxyl group.

It is preferable that the amine (b2) is one selected from the group consisting of serine, threonine and tyrosine. The selection of the amine (b2) from among these amino acids offers the same merits as those derived from the use of a phosphate of an amino acid as the amine (b1). When $R^5$ is —$CH_2$— in the formula (6), it is serine; when $R^5$ is —$CH(CH_3)$— in the formula (6), it is threonine; and when $R^5$ is —$CH_2$-Ph- in the formula (6), it is tyrosine.

The method for producing the compound (VIII) represented by the formula (5) is not particularly limited, and a method the same as the method for producing the compound (I) of the present invention described above may be adopted. The thus-obtained compound (VIII) can be used suitably as an intermediate for obtaining the compound (I) of the present invention.

The compound (I) of the present invention obtained by the above-mentioned method may be used alone. It, however, is preferable to use it in the form of a composition by mixing it with other components. When using the composition in the form of a composition, it is preferable that the composition contains the compound (I) of the present invention and a polymerizable monomer (II), other than the compound (I), which can be copolymerized with the compound (I). While the polymerizable monomer (II) which can be copolymerized is not particularly limited, it is preferably a (meth)acrylate compound. Specific examples of the (meth)acrylate compound are listed below.

Examples of a monofunctional monomer having no acidic group (namely, a polymerizable monomer having one polymerizable group) include methyl (meth)acrylate, ethyl (meth)acrylate, propyl (meth)acrylate, isopropyl (meth)acrylate, butyl (meth)acrylate, isobutyl (meth)acrylate, benzyl (meth)acrylate, lauryl (meth)acrylate, tetrahydrofurfuryl (meth)acrylate, glycidyl (meth)acrylate, 2-(N,N-dimethylamino)ethyl (meth)acrylate, 2,3-dibromopropyl (meth)acrylate, 3-chloro-2-hydroxypropyl (meth)acrylate and 3-methacryloyloxypropyltrimethoxysilane. Examples of a monofunctional monomer having no acidic group and having a hydroxyl group (namely, a polymerizable monomer having a hydroxyl group) include 2-hydroxylethyl (meth)acrylate, 3-hydroxypropyl (meth)acrylate, 6-hydroxyhexyl (meth)acrylate, 10-hydroxydecyl (meth)acrylate, glycerol mono(meth)acrylate, erythritol mono(meth)acrylate, 2,3-dihydroxybutyl (meth)acrylate, 2,4-dihydroxybutyl (meth)acrylate, 2-hydroxymethyl-3-hydroxypropyl (meth)acrylate, 2,2-bis(hydroxymethyl)-3-hydroxypropyl (meth)acrylate, 2,3,4,5-tetrahydroxypentyl (meth)acrylate, diethylene glycol mono(meth)acrylate, triethylene glycol mono(meth)acrylate, tetraethylene glycol mono(meth)acrylate, pentaethylene glycol mono(meth)acrylate, N-methylol(meth)acrylamide, N-hydroxyethyl(meth)acrylamide and N,N-(dihydroxyethyl)(meth)acrylamide. Among them, 2-hydroxylethyl (meth)acrylate, 3-hydroxypropyl (meth)acrylate, glycerol mono(meth)acrylate and erythritol mono(meth)acrylate are more preferable, and 2-hydroxylethyl (meth)acrylate is particularly preferable because these compounds are easy to be obtained and have appropriate hydrophilicity. When using a composition containing the compound (I) of the present invention as a "primer composition" or a "bonding material for used in a one-bottle, one-step adhesive system," which are described later, it is particularly preferable to incorporate the aforementioned polymer having a hydroxyl group into the composition.

Examples of a monofunctional monomer having one carboxyl group or an anhydride group thereof in the molecule include (meth)acrylic acid, N-(meth)acryloylglycine, N-(meth)acryloylaspartic acid, N-(meth)acryloyl-5-aminosalicylic acid, 2-(meth)acryloyloxyethyl hydrogen succinate, 2-(meth)acryloyloxyethyl hydrogen phthalate, 2-(meth)acryloyloxyethyl hydrogen malate, 6-(meth)acryloyloxyethyl naphthalene-1,2,6-tricarboxylic acid, O-(meth)acryloyltyrosine, N-(meth)acryloyltyrosine, N-(meth)acryloylphenylalanine, N-(meth)acryloyl-p-aminobenzoic acid, N-(meth)acryloyl-o-aminobenzoic acid, p-vinylbenzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, N-(meth)acryloyl-4-aminosalicylic acid, and the like, and acid anhydrides or acid halides of the foregoing radical polymerizable monomers.

Examples of a monofunctional monomer having two or more carboxyl groups or anhydride groups thereof in the molecule include 11-(meth)acryloyloxyundecane-1,1-dicarboxylic acid, 10-(meth)acryloyloxydecane-1,1-dicarboxylic acid, 12-(meth)acryloyloxydodecane-1,1-dicarboxylic acid, 6-(meth)acryloyloxyhexane-1,1-dicarboxylic acid, 2-(meth)acryloyloxyethyl-3'-methacryloyloxy-2'-(3,4-dicarboxybenzoyloxy)propylsuccinate, 4-(2-(meth)acryloyloxyethyl)trimellitate anhydride, 4-(2-(meth)acryloyloxyethyl) trimellitate, 4-(meth)acryloyloxyethyl trimellitate, 4-(meth)acryloyloxybutyl trimellitate, 4-(meth)acryloyloxyhexyl trimellitate, 4-(meth)acryloyloxydecyl trimellitate, 6-(meth)acryloyloxyethylnaphthalene-1,2,6-tricarboxylic anhydride, 6-(meth)acryloyloxyethylnaphthalene-2,3,6-tricarboxylic anhydride, 4-(meth)acryloyloxyethylcarbonyl propionoyl-1,8-naphthalic anhydride, 4-(meth)acryloyloxyethyl naphthalene-1,8-tricarboxylic anhydride, 9-(meth)acryloyloxynonane-1,1-dicarboxylic acid, 13-(meth)acryloyloxytridecane-1,1-dicarboxylic acid, and 11-(meth)acrylamidoundecane-1,1-dicarboxylic acid.

Examples of a monofunctional monomer having a phosphinyloxy group or a phosphonooxy group in the molecule, which may be referred to as a monofunctional radically polymerizable acidic phosphoric acid ester, include 2-(meth)acryloyloxyethyl dihydrogen phosphate, 2-(meth)acryloyloxyethylphenyl hydrogen phosphate, 10-(meth)acryloyloxydecyl dihydrogen phosphate, 6-(meth)acryloyloxyhexyl dihydrogen phosphate, 2-(meth)acryloyloxyethyl-2-bromoethyl hydrogen phosphate, and 2-(meth)acrylamidoethyl dihydrogen phosphate.

Other monofunctional groups having an acidic group include monofunctional groups having a sulfo group in the molecule such as 2-(meth)acrylamido-2-methylpropane sulfonic acid and 10-sulfodecyl (meth)acrylate.

The bifunctional monomers can be divided roughly into two categories, the aromatic compound type and the aliphatic compound type. Examples of the aromatic compound type bifunctional monomers include 2,2-bis((meth)acryloyloxyphenyl) propane, 2,2-bis[(4-(3-(meth)acryloyloxy)-2-hydroxypropoxyphenyl)]propane (common name "Bis-GMA"), 2,2-bis(4-(meth)acryloyloxyphenyl) propane, 2,2-bis(4-(meth)acryloyloxypolyethoxyphenyl) propane, 2,2-bis (4-(meth)acryloyloxydiethoxyphenyl) propane, 2,2-bis(4-(meth)acryloyloxytetraethoxyphenyl) propane, 2,2-bis(4-(meth)acryloyloxypentaethoxyphenyl) propane, 2,2-bis(4-(meth)acryloyloxydipropoxyphenyl) propane, 2-(4-(meth)acryloyloxydiethoxyphenyl)-2-(4-(meth)acryloyloxydiethoxyphenyl) propane, 2-(4-(meth)acryloyloxydiethoxyphenyl)-2-(4-(meth)acryloyloxyditriethoxyphenyl) propane, 2-(4-(meth)acryloyloxydipropoxyphenyl)-2-(4-(meth)acryloyloxytriethoxyphenyl) propane, 2,2-bis(4-(meth)acryloyloxypropoxyphenyl) propane, 2,2-bis(4-(meth)acryloyloxyisopropoxyphenyl) propane, and 1,4-bis(2-(meth)acryloyloxyethyl)pyromellitate. Among them, 2,2-bis[(4-(3-(meth)acryloyloxy)-2-hydroxypropoxyphenyl)]propane (common name "Bis-GMA") and 2,2-bis(4-(meth)acryloyloxypolyethoxyphenyl)propane are preferable. In the use of a composition containing the compound (I) of the present invention as a "bonding material for use in a one-bottle, one-step adhesive system" which is described later, it is preferable to incorporate the above-mentioned bifunctional monomer of the aromatic compound type into the composition, and it is preferable particularly to incorporate 2,2-bis[(4-(3-(meth)acryloyloxy)-2-hydroxypropoxyphenyl)]propane (common name "Bis-GMA").

Examples of the aliphatic compound type bifunctional monomers include ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, polyethylene glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, 1,2-bis(3-methacryloyloxy-2-hydroxypropoxy)ethane, 2,2,4-trimethylhexamethylene bis(2-carbamoyloxyethyl) dimethacrylate (common name "UDMA"), bis[2-(meth)acryloyloxyethyl]hydrogen phosphate, bis(6-(meth)acryloyloxyhexyl)hydrogen phosphate, bis(10-(meth)acryloyloxydecyl)hydrogen phosphate and bis{2-(meth)acryloyloxy(1-hydroxymethyl)ethyl}hydrogen phosphate. Among them, triethylene glycol di(meth)acrylate, neopentyl glycol di(meth)acrylate, 1,6-hexanediol di(meth)acrylate, 1,10-decanediol di(meth)acrylate, 1,2-bis(3-methacryloyloxy-2-hydroxypropoxy)ethane, and 2,2,4-trimethylhexamethylenebis(2-carbamoyl oxyethyl) dimethacrylate (common name "UDMA") are preferable. In the use for applications where hydrophilicity is required such as primer compositions, triethylene glycol di(meth)acrylate and 1,2-bis(3-methacryloyloxy-2-hydroxypropoxy)ethane are more preferable, and 1,2-bis(3-methacryloyloxy-2-hydroxypropoxy)ethane is particularly preferable.

Examples of tri- or higher functional monomer include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol tri(meth)acrylate, dipentaerythritol tetra(meth)acrylate, dipentaerythritol penta(meth)acrylate, N,N-(2,2,4-trimethylhexamethylene) bis[2-(aminocarboxy)propane-1,3-diol]tetramethacrylate, and 1,7-diacryloyloxy-2,2,6,6-tetraacryloyloxymethyl-4-oxyheptane.

Each of the (meth)acrylate compounds may be used singly or in combination of two or more compounds. If necessary, esters of unsaturated organic acids, such as α-cyanoacrylic acid, α-halogenated acrylic acid, crotonic acid, cinnamic acid, sorbic acid, maleic acid and itaconic acid, vinyl esters, vinyl ethers, mono-N-vinyl derivatives, styrene derivative, and the like may be used together with a (meth)acrylate compound.

The incorporated amount ratios of the compound (I) and the polymerizable monomer (II) are not particularly limited. In a preferable embodiment, when the sum total of the (I) and the (II) is let be 100 parts by weight, the incorporated amount ratios are 1 to 99 parts by weight of the (I) and 1 to 99 parts by weight of the (II). The incorporated amount ratios are more preferably 2 to 90 parts by weight of the (I) and 10 to 98 parts by weight of (II), and even more preferably 3 to 80 parts by weight of the (I) and 20 to 97 parts by weight of the (II).

As the polymerization initiator (III) to be used for the present invention, polymerization initiators which are in use in the industrial field can be selected and employed. In particular, polymerization initiators which are used for dental applications are preferably used. Especially, polymerization initiators for photopolymerization and chemical polymerization are used individually or in proper combination of two or more of them.

Among the polymerization initiator (III) to be used for the present invention, the photopolymerization initiators include (bis)acylphosphine oxides, water-soluble acylphosphine oxides, thioxanthones or quarternary ammonium salts of thioxanthones, ketals, α-diketones, coumarins, anthraquinones, benzoin alkyl ether compounds, and α-aminoketone compounds.

Among the (bis)acylphosphine oxides contained in the photopolymerization initiator to be used for the present invention, the acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyldi-(2,6-dimethylphenyl) phosphonate. The bisacylphosphine oxide includes bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl)phenylphosphine oxide, bis(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, and (2,5,6-trimethylbenzoyl)-2,4,4-trimethylpentylphosphine oxide.

The water-soluble acylphosphine oxide contained in the photopolymerization initiator to be used for the present invention preferably has an alkali metal ion, an alkaline earth metal ion, a pyridinium ion or an ammonium ion in an acylphosphine oxide molecule. For example, the water-soluble acylphosphine oxides can be synthesized by the method disclosed in European Patent No. 0009348 or Japanese Laid-Open Patent Publication No. 57-197289.

Specific examples of the water-soluble acylphosphine oxides include sodium monomethylacetylphosphonate, sodium monomethyl(1-oxopropyl)phosphonate, sodium monomethylbenzoylphosphonate, sodium monomethyl(1-oxobutyl)phosphonate, sodium monomethyl(2-methyl-1-oxopropyl)phosphonate, sodium acetylphosphonate, sodium monomethylacetylphosphonate, sodium acetylmethylphosphonate, sodium methyl 4-(hydroxymethoxyphosphinyl)-4-oxobutanoate, monosodium methyl-4-oxophosphonobutanoate, sodium acetylphenylphosphinate, sodium (1-oxopropyl)pentylphosphinate, sodium methyl-4-(hydroxypentylphosphinyl)-4-oxobutanoate, sodium acetylpentylphosphinate, sodium acetylethylphosphinate, sodium methyl(1,1-dimethyl)methylphosphinate, sodium (1,1-diethoxyethyl)methylphosphinate, lithium methyl-4-(hydroxymethylphosphinyl)-4-oxobutanoate, dilithium 4-(hydroxymethylphosphinyl)-4-oxobutanoate, sodium methyl(2-methyl-1,3-dioxolan-2-yl)phosphinate, sodium methyl(2-methyl-1,3-thiazolidin-2-yl)phosphonite, sodium (2-methylperhydro-1,3-diazin-2-yl)phosphonite, sodium acetylphosphinate, sodium (1,1-diethoxyethyl)phosphonite, sodium (1,1-diethoxyethyl)methylphosphonite, sodium methyl(2-methyloxathiolan-2-yl)phosphinate, sodium methyl(2,4,5-trimethyl-1,3-dioxolan-2-yl)phosphinate, sodium methyl(1,1-propoxyethyl)phosphinate, sodium (1-methoxyvinyl)methylphosphinate, sodium methyl(1-ethylthiovinyl)methylphosphinate, sodium methyl(2-methylperhydro-1,3-diazin-2-yl)phosphinate, sodium methyl(2-methylperhydro-1,3-thiazin-2-yl)phosphinate, sodium methyl (2-methyl-1,3-diazolidin-2-yl)phosphinate, sodium methyl (2-methyl-1,3-thiazolidin-2-yl)phosphinate, sodium (2,2-dicyano-1-methylethynyl)phosphinate, sodium acetylmethylphosphinate oxime, sodium acetylmethylphosphinate-O-benzyloxime, sodium 1-[(N-ethoxyimino)ethyl]methylphosphinate, sodium methyl(1-phenyliminoethyl)phosphinate, sodium methyl(1-phenylhydrazoneethyl)phosphinate, sodium [-(2,4-dinitrophenylhydrazono)ethyl]methylphosphinate, sodium acetylmethylphosphinatesemicarbazone, sodium (1-cyano-1-hydroxyethyl)methylphosphinate, sodium (dimethoxymethyl)methylphosphinate, sodium formylmethylphosphinate, sodium (1,1-dimethoxypropyl)methylphosphinate, sodium methyl(1-oxopropyl)phosphinate, dodecylguanidine methyl(1,1-dimethoxypropyl)phosphinate, isopropylamine 1,1-dimethoxypropyl)methylphosphinate, sodium acetylmethylphosphinate thiosemicarbazone, 1,3,5-tributyl-4-methylamino-1,2,4-triazolium (1,1-dimethoxyethyl)-methylphosphinate, 1-butyl-4-butylaminomethylamino-3,5-dipropyl-1,2,4-triazolium (1,1-dimethoxyethyl)-methylphosphinate, sodium 2,4,6-trimethylbenzoylphenylphosphine oxide, potassium 2,4,6-trimethylbenzoylphenylphosphone oxide, and an ammonium salt of 2,4,6-trimethylbenzoylphenylphosphine oxide. In addition, compounds disclosed in Japanese Laid-Open Patent Publication No. 2000-159621 are also included.

Among these (bis)acylphosphine oxides and water-soluble acylphosphine oxides, 2,4,6-trimethylbenzoyldiphenylphosphine oxide, 2,4,6-trimethylbenzoylmethoxyphenylphosphine oxide, bis(2,4,6-trimethylbenzoyl)acylphosphine oxide and sodium 2,4,6-trimethylbenzoylphenylphosphine oxide are particularly preferable.

Examples of the thioxanthone or the quarternary ammonium salt of a thioxanthone contained in the photopolymerization initiator to be used for the present invention include thioxanthone, 2-chlorothioxanthen-9-one, 2-hydroxy-3-(9-oxy-9H-thioxanthen-4-yloxy)-N,N,N-trimethyl-propaneaminium chloride, 2-hydroxy-3-(1-methyl-9-oxy-9H-thioxanthen-4-yloxy)-N,N,N-trimethyl-propaneaminium chloride, 2-hydroxy-3-(9-oxo-9H-thioxanthen-2-yloxy)-N,N,N-trimethyl-propaneaminium chloride, 2-hydroxy-3-(3,4-dimethyl-9-oxo-9H-thioxanthen-2-yloxy)-N,N,N-trimethyl-1-propaneaminium chloride, 2-hydroxy-3-(3,4-dimethyl-9H-thioxanthen-2-yloxy)-N,N,N-trimethyl-1-propaneaminium chloride, and 2-hydroxy-3-(1,3,4-trimethyl-9-oxo-9H-thioxanthen-2-yloxy)-N,N,N-trimethyl-1-propaneaminium chloride.

Among these thioxanthones or quaternary ammonium salts of thioxanthones, a particularly preferable thioxanthone is 2-chlorothioxanthen-9-one, and a particularly preferable quarternary ammonium salt of thioxanthone is 2-hydroxy-3-(3,4-dimethyl-9H-thioxanthen-2-yloxy)-N,N,N-trimethyl-1-propaneaminium chloride.

Examples of the ketal contained in the photopolymerization initiator to be used for the present invention include benzyl dimethyl ketals and benzyl diethyl ketals.

Examples of the α-diketone contained in the photopolymerization initiator to be used for the present invention include diacetyl, dibenzyl, camphorquinone, 2,3-pentadione, 2,3-octadione, 9,10-phenanthrenequinone, 4,4'-oxybenzyl, and acenaphthenequinone. Among them, camphorquinone is particularly preferable from the viewpoint of having a maximum absorption wavelength in the visible light region.

Examples of the coumarin compound contained in the photopolymerization initiator used for the present invention include compounds disclosed in Japanese Laid-Open Patent Publication Nos. 9-3109 and 10-245525 such as 3,3'-carbonylbis(7-diethylamino)coumarin, 3-(4-methoxybenzoyl)coumarin, 3-thienoylcoumarin, 3-benzoyl-5,7-dimethoxycoumarin, 3-benzoyl-7-methoxycoumarin, 3-benzoyl-6-methoxycoumarin, 3-benzoyl-8-methoxycoumarin, 3-benzoylcoumarin, 7-methoxy-3-(p-nitrobenzoyl)coumarin, 3-(p-nitrobenzoyl)coumarin, 3-benzoyl-8-methoxycoumarin, 3,5-carbonylbis(7-methoxycoumarin), 3-benzoyl-6-bromocoumarin, 3,3'-carbonylbiscumarin, 3-benzoyl-7-dimethylaminocoumarin, 3-benzoylbenzo[f]coumarin, 3-carboxycoumarin, 3-carboxy-7-methoxycoumarin, 3-ethoxycarbonyl-6-methoxycoumarin, 3-ethoxycarbonyl-8-methoxycoumarin, 3-acetylbenzo[f]coumarin, 7-methoxy-3-(p-nitrobenzoyl)coumarin, 3-(p-nitrobenzoyl)coumarin, 3-benzoyl-6-nitrocoumarin, 3-benzoyl-7-diethylaminocoumarin, 7-dimethylamino-3-(4-methoxybenzoyl)coumarin, 7-diethylamino-3-(4-methoxybenzoyl)coumarin, 7-diethylamino-3-(4-diethylamino)coumarin, 7-methoxy-3-(4-methoxybenzoyl)coumarin, 3-(4-nitrobenzoyl)benzo[f]coumarin, 3-(4-ethoxycinnamoyl)-7-methoxycoumarin, 3-(4-dimethylaminocinnamoyl)coumarin, 3-(4-diphenylaminocinnamoyl)coumarin, 3-[(3-dimethylbenzothiazol-2-ylidene)

acetyl]coumarin, 3-[(1-methylnaphtho[1,2-d]thiazole-2-ylidene)acetyl]coumarin, 3,3'-carbonylbis(6-methoxycoumarin), 3,3'-carbonylbis(7-acetoxycoumarin), 3,3'-carbonylbis(7-dimethylaminocoumarin), 3-(2-benzothiazoyl)-7-(diethylamino)coumarin, 3-(2-benzothiazoyl)-7-(dibutylamino)coumarin, 3-(2-benzoimidazoyl)-7-(diethylamino)coumarin, 3-(2-benzothiazoyl)-7-(dioctylamino)coumarin, 3-acetyl-7-(dimethylamino) coumarin, 3,3-carbonylbis(7-dibutylaminocoumarin), 3,3'-carbonyl-7-diethylaminocoumarin-7'-bis(butoxyethyl) aminocoumarin, 10-[3-[4-(dimethylamino)phenyl]-1-oxo-2-propenyl]-2,3,6,7-1,1,7,7-tetramethyl-1H,5H,11H-[1]benzopyrano[6,7,8-ij]quinolidin-1'-one, and 10-(2-benzothiazoyl)-2,3,6,7-tetrahydro-1,1,7,7-tetramethyl-1H, 5H,11H-[1]benzopyrano[6,7,8-ij]quinolidin-11-one.

Among the coumarin compounds listed above, 3,3'-carbonylbis(7-diethylaminocoumarin) and 3,3'-carbonylbis(7-dibutylaminocoumarin) are particularly preferable.

Example of the anthraquinone contained in the photopolymerization initiator to be used for the present invention include anthraquinone, 1-chloroanthraquinone, 2-chloroanthraquinone, 1-bromoanthraquinone, 1,2-benzanthraquinone, 1-methylanthraquinone, 2-ethylanthraquinone, and 1-hydroxyanthraquinone.

Examples of the benzoin alkyl ether contained in the photopolymerization initiator to be used for the present invention include benzoin methyl ether, benzoin ethyl ether, benzoin isopropyl ether, and benzoin isobutyl ether.

Examples of the α-aminoketone contained in the photopolymerization initiator to be used for the present invention include 2-methyl-1-[4-(methylthio)phenyl]-2-morpholino-propan-1-one.

Among these photopolymerization initiators, it is preferable to use at least one selected from the group consisting of the (bis)acylphosphine oxides and the salts thereof, the α-diketones and the coumarin compounds. This makes it possible to obtain an adhesive composition containing the compound (I) which is excellent in photocurability in the visible region and the near ultraviolet region and exerts sufficient photocurability when any light source selected from halogen lamp, light-emitting diode (LED) and xenon lamp is used.

Among the polymerization initiators (III) to be used for the present invention, organic peroxides are used preferably as chemical polymerization initiators. The organic peroxides to be used as chemical polymerization initiators are not particularly limited and known organic peroxides can be used. Representative organic peroxides include ketone peroxides, hydroperoxides, diacyl peroxides, dialkyl peroxides, peroxyketals, peroxyesters, and peroxydicarbonates.

The ketone peroxides include methyl ethyl ketone peroxide, methyl isobutyl ketone peroxide, methylcyclohexanone peroxide, and cyclohexanone peroxide.

The hydroperoxides include 2,5-dimethylhexane-2,5-dihydroperoxide, diisopropylbenzene hydroperoxide, cumene hydroperoxide, and tert-butyl hydroperoxide.

The diacyl peroxides include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide. The dialkyl peroxides include di-tert-butyl peroxide, dicumyl peroxide, tert-butyl cumyl peroxide, 2,5-dimethyl-2,5-di-(tert-butylperoxy)hexane, 1,3-bis(tert-butylperoxyisopropyl)benzene, and 2,5-dimethyl-2,5-di(tert-butylperoxy)-3-hexyne.

The peroxyketals include 1,1-bis(tert-butyl peroxy)-3,3,5-trimethylcyclohexane, 1,1-bis(tert-butylperoxy)cyclohexane, 2,2-bis(tert-butylperoxy)butane, 2,2-bis(tert-butylperoxy)octane, and n-butyl 4,4-bis(tert-butylperoxy)valerate.

The peroxyesters include α-cumyl peroxy neodecanoate, tert-butyl peroxy neodecanoate, tert-butyl peroxy pivalate, 2,2,4-trimethylpentyl peroxy-2-ethylhexanoate, tert-amyl peroxy-2-ethylhexanoate, tert-butyl peroxy-2-ethylhexanoate, di-tert-butyl peroxy isophthalate, di-tert-butyl peroxy hexahydroterephthalate, tert-butyl peroxy 3,3,5-trimethyl hexanoate, tert-butyl peroxyacetate, tert-butyl peroxybenzoate, and tert-butyl peroxy maleic acid.

The peroxydicarbonates include di-3-methoxy peroxydicarbonate, di-2-ethylhexyl peroxydicarbonate, bis(4-tert-butylcyclohexyl) peroxydicarbonate, diisopropyl peroxydicarbonate, di-n-propyl peroxydicarbonate, di-2-ethoxyethyl peroxydicarbonate, and diallyl peroxydicarbonate.

Among these organic peroxide, diacyl peroxides are preferably used because of their overall balance among safety, storage stability and radical generating ability. Among them, benzoyl peroxide is particularly preferably used.

The incorporated amount of the polymerization initiator (III) is not particularly limited. From the viewpoint, for example, of the curability of a composition to be obtained, it is preferable that the polymerization initiator (III) is incorporated at an amount of 0.01 to 15 parts by weight, more preferably 0.03 to 10 parts by weight relative to 100 parts by weight in total of the compound (I) and the polymerizable monomer (II).

In a preferable embodiment, the polymerization initiator (III) is used together with a polymerization accelerator (IV). Examples of the polymerization accelerator (IV) to be used for the present invention include amines, sulfinic acid and salts thereof, borate compounds, barbituric acid derivatives, triazine compounds, copper compounds, tin compounds, vanadium compounds, halogen compounds, aldehydes and thiol compounds.

The amines included in the polymerization accelerator (IV) to be used for the present invention are divided into aliphatic amines and aromatic amines. The aliphatic amines include primary aliphatic amines such as n-butylamine, n-hexylamine and n-octylamine; secondary aliphatic amines such as diisopropylamine, dibutylamine and N-methyldiethanolamine; tertiary aliphatic amines such as N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine and tributylamine. Among them, the tertiary amines are preferred from the viewpoint of the curability and the storage stability of a composition. Among them, N-methyldiethanolamine and triethanolamine are more preferably used.

Examples of the aromatic amines include N,N-bis(2-hydroxyethyl)-3,5-dimethylaniline, N,N-di(2-hydroxyethyl-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-tert-butyl aniline, N,N-bis(2-hydroxyethyl)-3,5-di-isopropylaniline, N,N-bis(2-hydroxyethyl)-3,5-di-tert-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-tert-butylaniline, N,N-dimethyl-3,5-di-tert-butylaniline, ethyl 4-N,N-dimethylaminobenzoate, methyl 4-N,N-dimethylaminobenzoate, n-butoxyethyl N,N-dimethylaminobenzoate, 2-(methacryloyloxy)ethyl 4-N,N-dimethylaminobenzoate, 4-N,N-dimethylaminobenzophenone, and butyl 4-dimethylaminobenzoate. Among them, at least one selected from the group consisting of N,N-di(2-hydroxyethyl)-p-toluidine, ethyl 4-N,N-dimethylaminobenzoate, n-butoxyethyl N,N-dimethylaminobenzoate, and 4-N,N-dimethylaminobenzophenone is used preferably from the viewpoint of being able to impart excellent curability to a composition.

Examples of the sulfinic acid and the salt thereof included in the polymerization accelerator (IV) to be used for the present invention include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethybenzenesulfinate, potassium 2,4,6-triethylbenzenesulfinate, lithium 2,4,6-triethylbenzenesulfinate, calcium 2,4,6-triethylbenzenesulfinate, 2,4,6-isopropylbenzenesulfinic acid, sodium 2,4,6-isopropylbenzenesulfinate, potassium 2,4,6-isopropylbenzenesulfinate, lithium 2,4,6-isopropylbenzenesulfinate, and calcium 2,4,6-isopropylbenzenesulfinate. Sodium benzenesulfinate, sodium p-toluenesulfinate, and sodium 2,4,6-isopropylbenzenesulfinate are particularly preferable.

The borate compounds included in the polymerization accelerator (IV) to be used for the present invention are preferably aryl borate compounds. Specific examples of the aryl borate compounds to be preferably used include, as borate compounds having one aryl group in one molecule, sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts and butylquinolinium salts of trialkylphenylboron, trialkyl(p-chlorophenyl)boron, trialkyl(p-fluorophenyl)boron, trialkyl(3,5-bistrifluoromethyl)phenylboron, trialkyl[3,5-bis(1,1,1,3,3,3-hexafluoro-2-methoxy-2-propyl)phenyl]boron, trialkyl(p-nitrophenyl)boron, trialkyl(m-nitrophenyl)boron, trialkyl(p-butylphenyl)boron, trialkyl(m-butylphenyl)boron, trialkyl(p-butyloxyphenyl)boron, trialkyl(m-butyloxyphenyl)boron, trialkyl(p-octyloxyphenyl)boron and trialkyl(m-octyloxyphenyl)boron (the alkyl group is at least one selected from the group consisting of a n-butyl group, a n-octyl group, a n-dodecyl group, or the like).

Borate compounds having two aryl groups in one molecule include sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts and butylquinolinium salts of dialkyl diphenylboron, dialkyl di(p-chlorophenyl)boron, dialkyl di(p-fluorophenyl)boron, dialkyl di(3,5-bistrifluoromethyl)phenylboron, dialkyl di[3,5-bis(1,1,1,3,3,3-hexafluoro-2-methoxy-2-propyl)phenyl]boron, dialkyl di(p-nitrophenyl)boron, dialkyl di(m-nitrophenyl)boron, dialkyl di(p-butylphenyl)boron, dialkyl di(m-butylphenyl)boron, dialkyl di(p-butyloxyphenyl)boron, dialkyl di(m-butyloxyphenyl)boron and dialkyl di(m-octyloxyphenyl)boron (the alkyl group is at least one selected from the group consisting of a n-butyl group, a n-octyl group, a n-dodecyl group, or the like).

Borate compounds having three aryl groups in one molecule include sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts and butylquinolinium salts of monoalkyl triphenylboron, monoalkyl tri(p-chlorophenyl)boron, monoalkyl tri(p-fluorophenyl)boron, monoalkyl tri(3,5-bis trifluoromethyl)phenylboron, monoalkyl tri[3,5-bis(1,1,1,3,3,3-hexafluoro-2-methoxy-2-propyl)phenyl]boron, monoalkyl tri(p-nitrophenyl)boron, monoalkyl tri(m-nitrophenyl)boron, monoalkyl tri(p-butylphenyl)boron, monoalkyl tri(m-butylphenyl)boron, monoalkyl tri(p-butyloxyphenyl)boron, monoalkyl tri(m-butyloxyphenyl)boron, monoalkyl tri(p-octyloxyphenyl)boron and monoalkyl tri(m-octyloxyphenyl)boron (the alkyl group is one selected from a n-butyl group, a n-octyl group, a n-dodecyl group, or the like).

Borate compounds having four aryl groups in one molecule include sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts and butylquinolinium salts of tetraphenylboron, tetrakis(p-chlorophenyl)boron, tetrakis(p-fluorophenyl)boron, tetrakis(3,5-bistrifluoromethyl)phenylboron, tetrakis[3,5-bis(1,1,1,3,3,3-hexafluoro-2-methoxy-2-propyl)phenyl]boron, tetrakis(p-nitrophenyl)boron, tetrakis(m-nitrophenyl)boron, tetrakis(p-butylphenyl)boron, tetrakis(m-butylphenyl)boron, tetrakis(p-butyloxyphenyl)boron, tetrakis(m-butyloxyphenyl)boron, tetrakis(p-octyloxyphenyl)boron, tetrakis(m-octyloxyphenyl)boron, (p-fluorophenyl)triphenylboron, (3,5-bistrifluoromethyl)phenyltriphenylboron, (p-nitrophenyl)triphenylboron, (m-butyloxyphenyl)triphenylboron, (p-butyloxyphenyl)triphenylboron, (m-octyloxyphenyl)triphenylboron and (p-octyloxyphenyl)triphenylboron.

Among these aryl borate compounds, a borate compound having three or four aryl groups in one molecule is preferably used from the viewpoint of the storage stability. These aryl borate compounds may be used singly or in the form of a mixture of two or more of them.

The barbituric acid derivatives included in the polymerization accelerator (IV) to be used for the present invention include barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl-n-butylbarbituric acid, 1,3-dimethyl-5-isobutylbarbituric acid, 1,3-dimethylbarbituric acid, 1,3-dimethyl-5-cyclopentylbarbituric acid, 1,3-dimethyl-5-cyclohexylbarbituric acid, 1,3-dimethyl-5-phenylbarbituric acid, 1-cyclohexyl-1-ethylbarbituric acid, 1-benzyl-5-phenylbarbituric acid, 5-methylbarbituric acid, 5-propylbarbituric acid, 1,5-diethylbarbituric acid, 1-ethyl-5-methylbarbituric acid, 1-ethyl-5-isobutylbarbituric acid, 1,3-diethyl-5-butylbarbituric acid, 1-cyclohexyl-5-methylbarbituric acid, 1-cyclohexyl-5-ethylbarbituric acid, 1-cyclohexyl-5-octylbarbituric acid, 1-cyclohexyl-5-hexylbarbituric acid, 5-butyl-1-cyclohexylbarbituric acid, 1-benzyl-5-phenylbarbituric acid, and thiobarbituric acids and their salts (especially, alkali metals or alkaline earth metals are preferable). Examples of the salts of these barbituric acids include sodium 5-butylbarbiturate, sodium 1,3,5-trimethylbarbiturate, and sodium 1-cyclohexyl-5-ethylbarbiturate.

Particularly preferable barbituric acid derivatives include 5-butylbarbituric acid, 1,3,5-trimethylbarbituric acid, 1-cyclohexyl-5-ethylbarbituric acid, 1-benzyl-5-phenylbarbituric acid, and sodium salts of these barbituric acids.

Examples of the triazine compounds included in the polymerization accelerator (IV) to be used for the present invention include 2,4,6-tris(trichloromethyl)-s-triazine, 2,4,6-tris(tribromomethyl)-s-triazine, 2-methyl-4,6-bis(trichloromethyl)-s-triazine, 2-methyl-4,6-bis(tribromomethyl)-s-triazine, 2-phenyl-4,6-bis(trichloromethyl)-s-triazine, 2-(p-methoxyphenyl)-4,6-bis(trichloromethyl)-s-triazine, 2-(p-methylthiophenyl)-4,6-bis(trichloromethyl)-s-triazine, 2-(p-chlorophenyl)-4,6-bis(trichloromethyl)-s-triazine, 2-(2,4-dichlorophenyl)-4,6-bis(trichloromethyl)-s-triazine, 2-(p-bromophenyl)-4,6-bis(trichloromethyl)-s-triazine, 2-(p-tolyl)-4,6-bis(trichloromethyl)-s-triazine, 2-n-propyl-4,6-bis(trichloromethyl)-s-triazine, 2-(α,α,β-trichloroethyl)-4,6-bis(trichloromethyl)-s-triazine, 2-styryl-4,6-bis(trichloromethyl)-s-triazine, 2-[2-(p-methoxyphenyl)ethenyl]-4,6-bis(trichloromethyl)-s-triazine, 2-[2-(o-methoxyphenyl)ethenyl]-4,6-bis(trichloromethyl)-s-triazine, 2-[2-(p-butoxyphenyl)ethenyl]-4,6-bis(trichloromethyl)-s-triazine, 2-[2-(3,4-dimethoxyphenyl)ethenyl]-4,6-bis(trichloromethyl)-s-triazine, 2-[2-(3,4,5-trimethoxyphenyl)ethenyl]-4,6-bis(trichloromethyl)-s-triazine, 2-(1-naphthyl)-4,6-bis(trichloromethyl)-s-triazine, 2-(4-biphenylyl)-4,6-bis(trichloromethyl)-s-triazine, 2-[2-{N,N-bis(2-hydroxyethyl)amino}ethoxy]-4,6-bis(trichloromethyl)-s-triazine, 2-[2-{N-hydroxyethyl-N-ethylamino}ethoxy]-4,6-bis(trichloromethyl)-s-triazine, 2-[2-{N-hydroxyethyl-N-methylamino}ethoxy]-4,6-bis(trichloromethyl)-s-triazine, and 2-[2-{N,N-diallylamino}ethoxy]-4,6-bis(trichloromethyl)-s-triazine.

Among the triazine compounds provided above as examples, particularly preferable compounds are 2,4,6-tris(trichloromethyl)-s-triazine from the viewpoint of polymerization activity, and 2-phenyl-4,6-bis(trichloromethyl)-s-triazine, 2-(p-chlorophenyl)-4,6-bis(trichloromethyl)-s-triazine, and 2-(4-biphenylyl)-4,6-bis(trichloromethyl)-s-triazine from the viewpoint of storage stability. The triazine compounds may be used singly or in the form of a mixture of two or more of them.

As the copper compound included in the polymerization accelerator (IV) to be used for the present invention, acetylacetone copper, cupric acetate, copper oleate, cupric chloride, cupric bromide, and the like are preferably used.

Examples of the tin compound included in the polymerization accelerator (IV) to be used for the present invention include di-n-butyltin dimaleate, di-n-octyltin dimaleate, di-n-octyltin dilaurate, and di-n-butyltin dilaurate. Particularly preferable tin compounds are di-n-octyltin dilaurate and di-n-butyltin dilaurate.

The vanadium compounds included in the polymerization accelerator (IV) to be used for the present invention preferably are IV-valent and/or V-valent vanadium compounds. Examples of the IV-valent and/or V-valent vanadium compounds include the compounds disclosed in Japanese Laid-Open Patent Publication No. 2003-96122, such as divanadium(IV) tetraoxide, vanadium(IV) oxide acetylacetonate, vanadyl(IV) oxalate, vanadyl(IV) sulfate, oxobis(1-phenyl-1,3-butanedionate)vanadium(IV), bis(maltolato)oxovanadium(IV), vanadium(V) pentoxide, sodium metavanadate (V), and ammonium metavanadate(V).

As the halogenated compound included in the polymerization accelerator (IV) to be used for the present invention, dilauryldimethylammonium chloride, lauryldimethylbenzylammonium chloride, benzyltrimethylammonium chloride, tetramethylammonium chloride, benzyldimethylcetylammonium chloride, dilauryldimethylammonium bromide, and the like are preferably used.

Examples of the aldehydes included in the polymerization accelerator (IV) to be used for the present invention include terephthalaldehyde and benzaldehyde derivatives. The benzaldehyde derivatives include dimethylaminobenzaldehyde, p-methyloxybenzaldehyde, p-ethyloxybenzaldehyde, and p-n-octyloxybenzaldehyde. Among them, p-n-octyloxybenzaldehyde is preferably used from the viewpoint of curability.

Examples of the thiol compounds included in the polymerization accelerator (IV) to be used for the present invention include 3-mercaptopropyltrimethoxysilane, 2-mercaptobenzoxazole, decanethiol, and thiobenzoic acid.

The incorporated amount of the polymerization accelerator (IV) is not particularly limited. From the viewpoint, for example, of the curability of a composition to be obtained, it is preferable that the polymerization accelerator (IV) is incorporated at an amount of 0.01 to 15 parts by weight relative to 100 parts by weight in total of the compound (I) and the polymerizable monomer (II).

In some embodiments, it is preferable that the composition containing the compound (I) of the present invention further contains filler (V). Such filler is usually divided roughly into organic filler, inorganic filler, and organic-inorganic composite filler. The organic filler includes polymethyl methacrylate, polyethyl methacrylate, methyl methacrylate-ethyl methacrylate copolymer, crosslinked type polymethyl methacrylate, crosslinked type polyethyl methacrylate, polyamide, polyvinyl chloride, polystyrene, chloroprene rubber, nitrile rubber, ethylene-vinyl acetate copolymer, styrene-butadiene copolymer, acrylonitrile-styrene copolymer, and acrylonitrile-styrene-butadiene copolymer. These may be used singly or in the form of a mixture of two or more of them. The organic filler is not particularly limited in shape, and it can be used with proper selection of the particle diameter of the filler. From the viewpoint of the handling efficiency and the mechanical strength of a composition to be obtained, the average particle diameter of the organic filler is preferably 0.001 to 50 μm, and more preferably 0.001 to 10 μm.

The inorganic filler includes quartz, silica, alumina, silica-titania, silica-titania barium oxide, silica-zirconia, silica-alumina, lanthanum glass, borosilicate glass, soda glass, barium glass, strontium glass, glass-ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. These may also be used singly or in the form of a mixture of two or more of them. The inorganic filler is not particularly limited in shape, and it can be used with proper selection of the particle diameter of the filler. From the viewpoint of the handling efficiency and the mechanical strength of a composition to be obtained, the average particle diameter of the inorganic filler is preferably 0.001 to 50 μm, and more preferably 0.001 to 10 μm.

With respect to the shape of the inorganic filler, irregularly shape filler and spherical filler are mentioned. From the viewpoint of improving the mechanical strength of a composition, it is preferable to use a spherical filler as the inorganic filler. Furthermore, when the spherical filler is used, there is an advantage that when a composition containing the compound (I) of the present invention is used as a dental composite resin, a composite resin with excellent surface smoothness can be obtained. The spherical filler as used herein is such a filler that when the filler is photographed by a scanning electron microscope (hereinafter, abbreviated as SEM), the particles found in a unit field of view are roundish and the average uniformity ratio, obtained by dividing the particle diameter in the direction perpendicular to the maximum diameter by the maximum diameter, is 0.6 or more. The average particle diameter of the spherical filler is preferably 0.1 to 5 μm. If the average particle diameter is less than 0.1 μm, the mechanical strength may decrease due to decrease in the filling factor of the spherical filler in the composition. On the other hand, if the average particle diameter exceeds 5 μm, no cured material having high mechanical strength may be obtained due to decrease in the surface area of the spherical filler.

In order to adjust the fluidity of a composition, the inorganic filler may be used after being subjected to surface treatment with a conventional surface treating agent such as a silane coupling agent, according to necessity. Examples of such surface treating agent include vinyltrimethoxysilane, vinyltriethoxysilane, vinyltrichlorosilane, vinyltri(β-methoxyethoxy)silane, γ-methacryloyloxypropyltrimethoxysilane, 11-methacryloyloxy undecyl trimethoxysilane, γ-glycidoxypropyltrimethoxysilane, γ-mercaptopropyl trimethoxysilane, and γ-aminopropyltriethoxysilane.

The organic-inorganic composite filler to be used in the present invention is a material obtained by adding a polymerizable monomer to the inorganic filler beforehand to form a paste, followed by polymerization and subsequent pulverization. As the organic-inorganic composite filler, TMPT filler (a product obtained by mixing trimethylolpropane methacrylate and silica filler, followed by polymerization and pulverization) can be used, for example. The organic-inorganic composite filler is not particularly limited in shape, and it can be used with proper selection of the particle diameter of the filler. From the viewpoint of the handling efficiency and the mechanical strength of a composition to be obtained, the average particle diameter of the organic-inorganic composite filler is preferably 0.001 to 50 μm, and more preferably 0.001 to 10 μm.

The incorporated amount of the filler (V) is not particularly limited. In a preferable embodiment, the filler (V) is incorporated at an amount of 0.1 to 2000 parts by weight relative to 100 parts by weight in total of the compound (I) and the polymerizable monomer (II). The preferable amount of the filler (V) to be incorporated may vary greatly according to the embodiment to be used. Therefore, the preferable amount of the filler (V) to be added for an individual embodiment is described with the following description about a specific embodiment of the compound (I) of the present invention.

In some specific embodiments, the composition containing the compound (I) of the present invention preferably contains a solvent (VI). The solvent (VI) includes water, methanol, ethanol, propanol, butanol, acetone, methyl ethyl ketone, hexane, toluene, chloroform, ethyl acetate, and butyl acetate. Among them, at least one selected from the group consisting of water, ethanol and acetone is used preferably when both the safety to a living body and the easiness of removal based on volatility are taken into consideration. Among them, it is preferable that the composition containing the compound (I) of the present invention further contains water (VII). Containing water (VII) provides an advantage that when a composition containing the compound (I) of the present invention is used as a dental composition, the decalcifying function of the tooth structure can be promoted. The water (VII) preferably contains no impurities which provide bad effects, and distilled water or ion exchange water is preferred. The water (VII) may be used singly, or alternatively may be used in the form of a mixed solvent of the water (VII) and a solvent (VI) other than the water (VII). The incorporated amount of the water (VI) is not particularly limited, and no incorporation of the solvent (VI) is needed in some embodiments. In embodiments in which the solvent (VI) is used, the solvent (VI) is incorporated at an amount of 1 to 5000 parts by weight relative to 100 parts by weight in total of the compound (I) and the polymerizable monomer (II). The preferable amount of the solvent (VI) to be incorporated may vary greatly according to the embodiment to be used. Therefore, the preferable amount of the solvent (VI) to be incorporated for an individual embodiment is described with the following description about a specific embodiment of the compound (I) of the present invention.

In addition, to the composition containing the compound (I) of the present invention, a polymerization inhibitor, a UV absorber, a thickener, a colorant, an antibacterial agent, a perfume, and the like may be incorporated unless the effect of the present invention is impaired.

The composition containing the compound (I) of the present invention is used suitably as a dental composition. The dental composition containing the compound (I) of the present invention can be employed as primer, bonding material, composite resin, cement (resin cement, glass ionomer cement, resin-reinforced glass ionomer cement), fissure sealant, resin for denture bases, or the like. Particularly, the dental composition containing the compound (I) of the present invention is used suitably as primer, bonding material, composite resin, or cement. A detailed description is made to an embodiment of each of the applications.

As described above, for filling a repair material into a defective part of a tooth or covering a defective part of a tooth with a repair material, a dental adhesive is usually used. Typically, the dental adhesive is applied to the dentin. When such a dental adhesive is applied to the dentin, it is important that the dental adhesive has a decalcifying function that an acidic component dissolves the surface of the dentin, a permeating function that a monomer component permeates a collagen layer of the dentin, and a curing function that the monomer component which has permeated hardens to form a hybrid layer with collagen (hereinafter, the layer may be referred to as a "resin impregnated layer"). The adhering system that separately performs the three steps "decalcification", "permeation", and "curing" is usually called "three-step adhering system." Basically, the product to be used for the permeation step is a primer, and the product to be used for the curing step is a bonding material.

For the simplification of a work process, a product by which the decalcification step and the permeation step are combined to be performed in a single stage has recently been developed and has been put into practice. The product is called a "self-etching primer." An adhesive system using a self-etching primer and a bonding material is usually called a "two-step adhesive system." The compound (I) of the present invention has a phosphoric acid group, so that it exhibits high acidity and has excellent decalcification ability. In addition, because it has a phosphoric acid group and a carboxyl group in the molecule, it exhibits high permeability to the collagen layer of the dentin. For this reason, it is preferable to use a composition containing the compound (I) of the present invention as a dental primer, and it also is preferable to use the composition as a self-etching primer for dental applications. In fact, as is clear from the comparison of Example 1 to Comparative Examples 1 and 2 in Examples provided infra, the use of the compound (I) of the present invention leads to great improvement in adhesive properties and it exerts excellent performance as a self-etching primer.

The primer containing the compound (I) of the present invention is preferably a composition containing the compound (I), a polymerizable monomer (II), a polymerization initiator (III), a polymerization accelerator (IV), and a solvent (VI). With respect to the incorporated amount of each component, when the total amount of the (I) and the (II) is let be 100 parts by weight, it is preferable that the amount of the (I) is 5 to 50 parts by weight and the amount of the (II) is 50 to 95 parts by weight; it is more preferable that the amount of the (I) is 10 to 45 parts by weight and the amount of the (II) is 55 to 90 parts by weight; and it is even more preferable that the amount of the (I) is 15 to 45 parts by weight and the amount of the (II) is 55 to 85 parts by weight. It is preferable that 0.1 to 5 parts by weight of the (III), 1 to 30 parts by weight of the (IV) and 20 to 300 parts by weight of the (VI) are contained relative to 100 parts by weight in total of the (I) and the (II); it is more preferable that 0.2 to 4 parts by weight of the (III), 2 to 25 parts by weight of the (IV) and 30 to 250 parts by weight of the (VI) are contained; and it is even more preferable that 0.3 to 3 parts by weight of the (III), 3 to 20 parts by weight of the (IV) and 40 to 200 parts by weight of the (VI) are contained.

From the viewpoint of increasing the hydrophilicity of a composition and increasing the permeability to the collagen layer of the dentin, the polymerizable monomer (II) to be used is preferably a monomer having a hydroxyl group in the molecule. The (II) to be used is preferably a mixture of a polymerizable monomer (II-a) having a hydroxyl group and a polymerizable monomer (II-b) having two or more polymerizable groups, and the polymerizable monomer (II-b) having two or more polymerizable groups is preferably an aliphatic compound-based bifunctional monomer. With regard to the incorporated amounts of the individual components, when the total amount of (I), (II-a) and (II-b) is let be 100 parts by weight, it is preferable that the (I) is at an amount of 5 to 50 parts by weight, the (II-a) is at an amount of 35 to 90 parts by weight, and the (II-b) is at an amount of 5 to 60 parts by weight; it is more preferable that the (I) is at an amount of 10 to 45 parts by weight, the (II-a) is at an amount of 40 to 83 parts by weight, and the (II-b) is at an amount of 7 to 50 parts by weigh; and it is even more preferable that the (I) is at an amount of 15 to 45 parts by weight, the (II-a) is at an amount of 45 to 75 parts by weight, and the (II-b) is at an amount of 10 to 40 parts by weight. Likewise, the polymerization accelerator (IV) is preferably an amine, and the solvent (VI) preferably contains water (VII). The content of the water (VII) in the solvent (VI) is preferably 50% by weight or more, more preferably 70% by weight or more, and particularly preferably 90% by weight or more. It is most preferable that the solvent (VI) is composed substantially only of water (VII).

Since the compound (I) of the present invention has a phosphoric acid group and a carboxyl group in the molecule, it strongly interacts with calcium in the hydroxyapatite which constitutes the tooth structure. Therefore, the composition containing the compound (I) of the present invention is used preferably as a bonding material. The bonding material in the "two-step adhesive system" is preferably a composition containing the (I), (II), (III), (IV) and (V). With respect to the incorporated amount of each component, when the total amount of the (I) and the (II) is let be 100 parts by weight, it is preferable that the amount of the (I) is 1 to 30 parts by weight and the amount of the (II) is 70 to 99 parts by weight; it is more preferable that the amount of the (I) is 2 to 20 parts by weight and the amount of the (II) is 80 to 98 parts by weight; and it is even more preferable that the amount of the (I) is 3 to 15 parts by weight and the amount of the (II) is 85 to 97 parts by weight. From the viewpoint of increasing the mechanical strength of a cured material, the (II) to be used is more preferably a polymerizable monomer having two or more polymerizable groups. It is preferable that 0.1 to 10 parts by weight of the (III), 0.1 to 20 parts by weight of the (IV) and 1 to 30 parts by weight of the (V) are contained relative to 100 parts by weight in total of the (I) and the (II); it is more preferable that 0.2 to 8 parts by weight of the (III), 0.5 to 15 parts by weight of the (IV) and 3 to 20 parts by weight of the (V) are contained; and it is even more preferable that 0.3 to 6 parts by weight of the (III), 1 to 10 parts by weight of the (IV) and 4 to 15 parts by weight of the (V) are contained.

Since further simplification of work has been desired in recent years, a product with which three steps "decalcification", "permeation", and "curing" are carried out collectively in a single stage has been developed, which is called "one-step adhesive system." As the bonding material used for such a one-step adhesive system, a bonding material which is used by mixing two separate bottles, A liquid and B liquid, just before the use, and a bonding material of a so-called "one-bottle one-step adhesive system," which is provided originally in the form of one bottle are two representative products. Among them, the one-bottle type is of great merit in use because it offers a more simplified step. When the composition containing the compound (I) of the present invention is used as a bonding material of the one-bottle one-step adhesive system, the composition is preferably a composition containing the (I), (II), (III), (IV), (V) and (VI). With respect to the incorporated amount of each component, when the total amount of the (I) and the (II) is let be 100 parts by weight, it is preferable that the amount of the (I) is 1 to 30 parts by weight and the amount of the (II) is 70 to 99 parts by weight; it is more preferable that the amount of the (I) is 5 to 25 parts by weight and the amount of the (II) is 75 to 95 parts by weight; and it is even more preferable that the amount of the (I) is 7 to 20 parts by weight and the amount of the (II) is 80 to 93 parts by weight. Since "permeation" and "curing" are carried out simultaneously in a one-bottle one-step adhesive system, the (II) to be used is preferably a mixture or a polymerizable monomer (II-a) having a hydroxyl group and a polymerizable monomer (II-b) having two or more polymerizable groups, and the polymerizable monomer (II-b) having two or more polymerizable groups is more preferably an aromatic compound-based bifunctional monomer. With regard to the incorporated amounts of the individual components, when the total amount of (I), (II-a) and (II-b) is let be 100 parts by weight, it is preferable that the (I) is at an amount of 1 to 30 parts by weight, the (II-a) is at an amount of 10 to 89 parts by weight, and the (II-b) is at an amount of 10 to 89 parts by weight; it is more preferable that the (I) is at an amount of 5 to 25 parts by weight, the (II-a) is at an amount of 15 to 80 parts by weight, and the (II-b) is at an amount of 15 to 80 parts by weight; and it is even more preferable that the (I) is at an amount of 7 to 20 parts by weight, the (II-a) is at an amount of 20 to 63 parts by weight, and the (II-b) is at an amount of 20 to 63 parts by weight. It is preferable that 0.5 to 20 parts by weight of the (III), 0.1 to 20 parts by weight of the (IV), 1 to 40 parts by weight of the (V) and 5 to 70 parts by weight of the (VI) are contained relative to 100 parts by weight in total of the (I) and the (II); it is more preferable that 1 to 17 parts by weight of the (III), 0.5 to 15 parts by weight of the (IV), 3 to 30 parts by weight of the (V) and 10 to 65 parts by weight of the (VI) are contained; and it is even more preferable that 3 to 15 parts by weight of the (III), 1 to 10 parts by weight of the (IV), 5 to 25 parts by weight of the (V) and 20 to 60 parts by weight of the (VI) are contained.

Since the compound (I) of the present invention has a phosphoric acid group and a carboxyl group in the molecule, it strongly interacts with calcium in the hydroxyapatite which constitutes the tooth structure. Therefore, the composition containing the compound (I) of the present invention is preferably used as a composite resin. When the composition containing the compound (I) of the present invention is used as a composite resin, the composition is preferably a composition containing the (I), (II), (III), (IV) and (V). composite resin is usually used by grinding a part where a dental caries has occurred to form a cavity and then filling the composite resin into the cavity. Then, the filled composite resin is cured usually by photopolymerization. Therefore, it is preferable to use a photopolymerization initiator as the (III). Moreover, the composite resin which has been filled and cured as described above is required to have excellent mechanical strength because it receives occlusal pressure in the oral cavity. For this reason, the composition preferably contains the filler (V) at an amount of 200 to 2000 parts by weight, more preferably 250 to 1500 parts by weight, and even more preferably 300 to 1200 parts by weight relative to 100 parts by weight in total of the (I) and the (II). If the content of the filler (V) is less than 200 parts by weight, the mechanical strength of a cured material may become insufficient. On the other hand, if the content of the filler (V) exceeds 2000 parts by weight, it may become difficult to disperse the filler (V) in the (I) and (II) uniformly, resulting in a composition which is insufficient in mechanical strength and handling efficiency.

The use of the compound (I) of the present invention as a dental cement by making the most of its strong interaction to the tooth structure is one of the preferable embodiments. Preferable examples of the cement include resin cement, glass ionomer cement, and resin-reinforced glass ionomer cement. When the composition containing the compound (I) of the present invention is used as a resin cement, the composition is preferably a composition containing the (I), (II), (III), (IV) and (V). A dental cement is preferably used, for example, as a luting material to be used for fixing, to a tooth, a restorative material for tooth crown made of metal or ceramic, called an inlay or a crown. Therefore, high mechanical strength is required in order to resist the occlusal pressure, and the like. From such a point of view, the (II) is more preferably a polymerizable monomer having two or more polymerizable groups. In the above-mentioned mode of use, because many of the restorative materials for dental caps are optically impermeable, it is not easy to cure the cement by photopolymerization. For this reason, it is preferable to use a chemical polymerization initiator as the (III). In order to increase the reactivity when polymerizing the compound (I) by using a chemical polymerization initiator, it is preferable to use an amine and/or a sulfinic acid or a salt thereof as the (IV), and it is more preferable to use an amine, a sulfinic acid and a salt thereof together at the same time. The filler (V) to be used is not particularly limited. When wishing to impart sustained fluorine releasability to the cement, it is preferable to use, as the filler (V), at least one selected from the group consisting of fluoroaluminosilicate glass, calcium fluoroaluminosilicate glass, strontium fluoroaluminosilicate glass, barium fluoroaluminosilicate glass and strontium calcium fluoroaluminosilicate glass. It is more preferable to use fluoroaluminosilicate glass and/or barium fluoroaluminosilicate glass. On the other hand, when wishing to impart radiopacity to the cement, it is preferable to use, as the filler (V), at least one selected from the group consisting of barium glass, strontium glass, barium boroaluminosilicate glass, strontium boroaluminosilicate glass, strontium fluoroaluminosilicate glass and barium fluoroaluminosilicate glass. It is more preferable to use barium glass and/or barium fluoroaluminosilicate glass.

When a chemical polymerization initiator is used, it is preferable, from the viewpoint of storage stability, to store the (III) and the (IV) in separate containers. That is, in a preferable embodiment, the resin cement is used in a two-component form. In a preferred embodiment, when a filler (V) is incorporated, a composition (liquid) containing the compound (I) of the present invention and the filler (V) (powder) are mixed to form a paste. Because of this, in a more preferable embodiment, the resin cement is used in a two-paste form. It is preferable to store respective pastes while keeping the pastes separated from one another and then mix the two pastes immediately before use to cause them to undergo chemical polymerization to cause curing. Moreover, the compound (I) of the present invention has a phosphoric acid group, so that it exhibits strong acidity. Therefore, when an amine and/or a sulfinic acid and a salt thereof is used as the (IV), it is preferable, from the viewpoint of storage stability, to store the (I) and the (IV) in separate containers. When the two pastes are called "paste A" and "paste B," respectively, an embodiment is particularly preferably employed in which paste A contains the (I), (II), (III), and (V) and paste B contains the (II), (IV) and (V).

When the composition containing the compound (I) of the present invention is used as a dental cement, the incorporated amount of each component is not particularly limited. However, when the sum total of the (I) and the (II) is let be 100 parts by weight, it is preferable that the (I) is at an amount of 0.1 to 30 parts by weight and the (II) is at an amount of 70 to 99.9 parts by weight. It is more preferable that the (I) is at an amount of 0.3 to 20 parts by weight and the (II) is at an amount of 80 to 99.7 parts by weight, and even more preferable that the (I) is at an amount of 0.5 to 10 parts by weight and the (II) is at an amount of 90 to 99.5 parts by weight. With respect to the incorporated amounts of the (III) and the (V), when taking into consideration that an appropriate setting time can be obtained, it is preferable to contain the (III) at an amount of 0.1 to 10 parts by weight and the (V) at an amount of 0.1 to 10 parts by weight, each relative to 100 parts by weight in total of the (I) and the (II), more preferable to contain the (III) at an amount of 0.3 to 8 parts by weight and the (IV) at an amount of 0.3 to 8 parts by weight, and even more preferable to contain the (III) at an amount of 0.5 to 6 parts by weight and the (IV) at an amount of 0.5 to 6 parts by weight.

Furthermore, it is preferable to contain the filler (V) at an amount of 20 to 1000 parts relative to 100 parts by weight in total of the (I) and the (II), more preferable to contain it at an amount of 40 to 600 parts by weight, and even more preferable to contain it at an amount of 70 to 400 parts by weight. If the content of the filler (V) is less than 20 parts by weight, the cured product may become insufficient in mechanical strength. On the other hand, if the content of the filler (V) exceeds 1000 parts by weight, when the resin cement is used in the form of a two-paste type cement, which is a preferred embodiment thereof, the paste may become insufficient in fluidity, so that it becomes difficult to perform sufficient mixing, and, as a result, the strength of the cured product may decrease.

It is preferable to use the composition containing the compound (I) of the present invention as a glass ionomer cement, and is more preferable to use it as a resin-reinforced type glass ionomer cement. It is believed that the glass ionomer cement typically develops its adhering function by a mechanism that an inorganic filler like fluoroaluminosilicate glass and a polyalkenic acid like polyacrylic acid react and cure through an acid-base reaction, and the polyacrylic acid and calcium in the hydroxyapatite which constitutes tooth structure interact together. Since the compound (I) of the present invention exhibits a very strong interaction with calcium as described above, it is conceivable that the compound is suitable for being used for a glass ionomer application. When the composition containing the compound (I) of the present invention is used as a glass ionomer cement, and particularly preferably as a resin-reinforced type glass ionomer cement, it is preferable that the composition is a composition containing (I), (II), (III), (IV), (V), (VI), and a polyalkenic acid.

The polyalkenic acid is a polymer of unsaturated monocarboxylic acid or unsaturated dicarboxylic acid. Specific examples of the polyalkenic acid include homopolymers of acrylic acid, methacrylic acid, 2-chloroacrylic acid, 2-cyanoacrylic acid, aconitic acid, mesaconic acid, maleic acid, itaconic acid, fumaric acid, glutaconic acid, citraconic acid, utraconic acid, and the like, or copolymers of such unsaturated carboxylic acids with monomers which can be copolymerized therewith. In the case of a copolymer, the proportion of the unsaturated carboxylic acid units is preferably 50 mol % or more to all the structural units. The copolymerizable monomer is preferably an ethylenically unsaturated polymerizable monomer; for example, styrene, acrylamide, acrylonitrile, methyl methacrylate, acrylic acid salts, vinyl chloride, allyl chloride, vinyl acetate, and 1,1,6-trimethylhexamethylene dimethacrylate ester. Among these polyalkenic acids, homopolymers or copolymers of acrylic acid or maleic acid are preferable. With respect to these polyalkenic acids, if the weight average molecular weight is less than 5,000, the cured product of a dental cement composition may become lower in strength and, as a result, the durability may be insufficient. On the other hand, if the weight average molecular weight exceeds 40,000, the consistency of a dental cement composition at the time of mixing may become harder and, as a result, the operability may decrease. Therefore, a preferable weight average molecular weight of the polyalkenic acid is 5,000 to 40,000.

From the viewpoint of the curability in an acid-base reaction and the sustained fluorine releasability, it is preferable to use, as the filler (V) to be used, at least one selected from the group consisting of fluoroaluminosilicate glass, calcium fluoroaluminosilicate glass, strontium fluoroaluminosilicate glass, barium fluoroaluminosilicate glass and strontium calcium fluoroaluminosilicate glass. It is more preferable to use fluoroaluminosilicate glass and/or barium fluoroaluminosilicate glass.

With respect to the solvent (VI) to be used, from the viewpoint of causing an acid-base reaction to proceed smoothly, it is preferable that the solvent (VI) contains water (VII). The content of the water (VII) in the solvent (VI) is preferably 50% by weight or more, more preferably 70% by weight or more, and particularly preferably 90% by weight or more. It is most preferable that the solvent (VI) is composed substantially only of water (VII).

When a composition containing the compound (I) of the present invention is used as a glass ionomer cement, particularly preferably as a resin-reinforced type glass ionomer cement, the incorporated amount of each component is not particularly limited. However, when the sum total of the (I) and the (II) is let be 100 parts by weight, it is preferable that the (I) is at an amount of 1 to 99 parts by weight and the (II) is at an amount of 1 to 99 parts by weight, and more preferable that the (I) is at an amount of 3 to 90 parts by weight and the (II) is at an amount of 10 to 97 parts by weight. With respect to the incorporated amounts of the (III) and the (V), when taking into consideration that an appropriate setting time can be obtained, it is preferable to contain the (III) at an amount of 0.1 to 10 parts by weight and the (IV) at an amount of 0.1 to 10 parts by weight, each relative to 100 parts by weight in total of the (I) and the (II), more preferable to contain the (III) at an amount of 0.3 to 8 parts by weight and the (IV) at an amount of 0.3 to 8 parts by weight, and even more preferable to contain the (III) at an amount of 0.5 to 6 parts by weight and the (IV) at an amount of 0.5 to 6 parts by weight. Furthermore, it is preferable to contain the filler (V) at an amount of 10 to 1000 parts relative to 100 parts by weight in total of the (I) and the (II), more preferable to contain it at an amount of 20 to 600 parts by weight, and even more preferable to contain it at an amount of 25 to 900 parts by weight. If the content of the filler (V) is less than 10 parts by weight, the cured product may become insufficient in mechanical strength. On the other hand, if the content of the filler (V) exceeds 1000 parts by weight, the composition paste comes to have a reduced fluidity and, as a result, it becomes difficult to achieve sufficient mixing. This may prevent an acid-base reaction from proceeding smoothly. As a result, the strength of a cured product may decrease.

Furthermore, it is preferable to contain the solvent (VI) at an amount of 10 to 300 parts relative to 100 parts by weight in total of the (I) and the (II), more preferable to contain it at an amount of 20 to 250 parts by weight, and even more preferable to contain it at an amount of 30 to 200 parts by weight. By containing the solvent (VI) at an amount within such a range, it is possible to cause an acid-base reaction to proceed smoothly and the mechanical strength of a resulting cured product and its adhesive properties to a tooth structure are enhanced.

It is preferable to contain the polyalkenic acid at an amount of 10 to 300 parts relative to 100 parts by weight in total of the (I) and the (II), more preferable to contain it at an amount of 20 to 250 parts by weight, and even more preferable to contain it at an amount of 30 to 200 parts by weight. By containing the polyalkenic acid at an amount within such a range, the curing due to an acid-base reaction proceeds smoothly and it is possible to reduce disintegration of a resulting cured product due to hydrolysis occurring in the oral cavity.

As described above, because curing is caused by the proceeding of an acid-base reaction, it is preferable, from the viewpoint of storage stability, that the filler (V) and the polyalkenic acid are packaged in separate containers and are used by being mixed immediately before use. With respect to the form of a product, while a so-called powder-liquid type form is preferably used, it is more preferable, from the viewpoint of improvement in handling efficiency, that the product is in a two-paste type glass ionomer cement containing two kinds of pastes. In the case of a two-paste type form, when the two pastes are called "paste A" and "paste B," respectively, an embodiment is particularly preferably employed in which paste A contains the (I), (II), (IV), (V), (VI) and polyalkenic acid and paste B contains the (II), (III) and (V). Likewise, an embodiment in which paste A contains the (I), (II), (III), (V), (VI) and polyalkenic acid and paste B contains the (II), (IV), and (V) is used preferably. In any embodiment, because paste A contains the polyalkenic acid, it is preferable to use, as the filler (V) contained in the B paste, at least one selected from the group consisting of fluoroaluminosilicate glass, calcium fluoroaluminosilicate glass, strontium fluoroaluminosilicate glass, barium fluoroaluminosilicate glass and strontium calcium fluoroaluminosilicate glass. It is more preferable to use fluoroaluminosilicate glass and/or barium fluoroaluminosilicate glass. As the filler (V) contained in the A paste, it is preferable to use a filler which exhibits no reactivity to a polyalkenic acid, and quartz is particularly preferably used.

The above are descriptions about the compound (I) of the present invention and a composition containing the same, a method for producing the compound (I) by causing a carboxylic acid and an amine to undergo condensation reaction by using a triazine-based condensing agent, and a method for producing the compound (I) by causing an acid halide and an amine to react. The method for producing a polymerizable amide by which a carboxylic acid and an amine are caused to undergo condensation reaction by using a triazine-based condensing agent is a novel production method, and it is useful also as a production method for obtaining not only the compound (I) but other polymerizable amides.

That is, the production method of the present invention is a method for producing a polymerizable amide by which a carboxylic acid is caused to undergo condensation reaction with an amine to form an amide bond, wherein at least one of the carboxylic acid and the amine has a polymerizable group and the condensation reaction is performed using a triazine-based condensing agent (IX).

In the production method of the present invention, at least one of the carboxylic acid and the amine has a polymerizable group. Therefore, the polymerizable amide obtained by causing the carboxylic acid and the amine to undergo condensation reaction also has a polymerizable group. The fact that the resulting polymerizable amide has a polymerizable group enables the amide to undergo polymerization and also enables it to undergo copolymerization with other monomers. Examples of the polymerizable group include a (meth)acryl group, a (meth)acrylamide group, a vinyl(thio)ether group, an allyl(thio)ether group, a vinyl ester group and a styryl group. Among them, a (meth)acryl group or a (meth)acrylamide group is preferable from the viewpoint that radical polymerization is easy.

In the production method of the present invention, a triazine-based condensing agent (IX) is used when a carboxylic acid and an amine are caused to undergo condensation reaction to form an amide bond. This makes it possible to carry out condensation reaction under mild conditions, and the safety is good because, unlike carbodiimide-based condensing agents, such an agent causes no skin irritation. The triazine-based condensing agent (IX) represented by the following formula (7) to be used for the production method of the present invention is described below.

[Chem. 32]

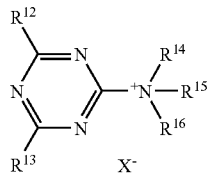

(7)

wherein $R^{12}$ and $R^{13}$ each independently are an alkoxy group or an alkyl group, $R^{14}$, $R^{15}$ and $R^{16}$ each independently are a hydrocarbon group having 1 to 20 carbon atoms which may have an oxygen atom, a nitrogen atom or a sulfur atom; X is a halogen atom, triflate, tosylate, mesylate or chloromethanesulfonate; $R^{14}$, $R^{15}$ and $R^{16}$ may link with each other to form a ring.

In the formula (7), the substituents $R^{12}$ and $R^{13}$ attached to a triazine ring are each independently an alkoxy group or an alkyl group. The alkoxy group includes straight-chain or branched-chain alkoxy groups having 1 to 20 carbon atoms, and examples thereof include a methoxy group, an ethoxy group, a n-propoxy, an isopropoxy group, a n-butoxy group, an isobutoxy group, a sec-butoxy group, a tert-butoxy group, a n-pentyloxy group, an isopentyloxy group, a neopentyloxy group, a n-hexyloxy group, an isohexyloxy group, a 2-ethylhexyloxy group, a n-heptyloxy group, a n-octyloxy group, a n-nonyloxy group and a n-decyloxy group. From the viewpoint of the reactivity of a condensing agent to be obtained, a methoxy group, an ethoxy group or an isopropoxy group is preferable, and a methoxy group is more preferable.

In the present invention, the alkyl group includes a straight-chain or branched-chain alkyl group having 1 to 20 carbon atoms, and examples thereof include a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a n-hexyl group, an isohexyl group, a 2-ethylhexyl group, a n-heptyl group, a n-octyl group, a n-nonyl group and a n-decyl group. From the viewpoint of the reactivity of a condensing agent to be obtained, a methyl group, an ethyl group or a tert-butyl group is preferable. Among them, it is preferable that each of the substituents $R^{12}$ and $R^{13}$ are a methoxy group because of the easiness of production and the balance with the reactivity of the condensing agent.

In the formula (7), $R^{14}$, $R^{15}$ and $R^{16}$ each independently are a hydrocarbon group having 1 to 20 carbon atoms which may have an oxygen atom, a nitrogen atom or a sulfur atom, and preferably are a hydrocarbon group having from 1 to 10 carbon atoms. $R^{14}$, $R^{15}$ and $R^{16}$ may link with each other to form a ring. Adjacent substituents may link to form a ring, or alternatively, substituents distant from each other may link to form a ring.

In the formula (7), X is a halogen atom, triflate, tosylate, mesylate or chloromethanesulfonate. The triazine-based condensing agent preferably is one resulting from a reaction of a triazine ring to which X is attached with a tertiary amine. X will leave through such a reaction to exist as a counter anion in the triazine-based condensing agent. It is preferable that the X is a functional group which is to be used a leaving group, and a halogen atom or triflate is preferably used. The halogen atom includes fluorine, chlorine, bromine, and iodine. Chlorine is preferably adopted in view of the balance between the reactivity and the storage stability of the condensing agent.

The triazine-based condensing agent (IX) to be used in the present invention preferably has a morpholine ring as shown in the following formula (8). As a result of this, the condensing agent comes to have a proper reactivity and also comes to have an increased crystallinity, so that it can be handled in the form of a powder. Therefore, a great merit can be obtained with respect to purification, storage stability, handling efficiency, and the like.

[Chem. 33]

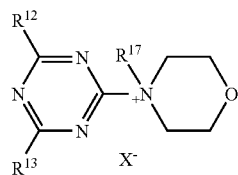

(8)

wherein $R^{12}$, $R^{13}$ and X are the same as those of the formula (7), and $R^{17}$ is a hydrocarbon group having 1 to 20 carbon atoms which may have a substituent.

The $R^{17}$ attached to the N of the morpholine ring in the formula (8) is a hydrocarbon group having 1 to 20 carbon atoms which may have a substituent, and the $R^{17}$ is preferably an alkyl group which may have a substituent. The alkyl groups provided as examples in the descriptions about $R^{12}$ and $R^{13}$ may be adopted as the alkyl group. From a viewpoint of the easiness in the production of a condensing agent and the storage stability of a resulting condensing agent, the alkyl group is preferably an alkyl group having 1 to 4 carbon atoms, and more preferably a methyl group.

In a preferable production method of the present invention, it is possible to obtain a polymerizable amide (X) by causing a carboxylic acid having a polymerizable group and an amine to undergo condensation reaction by the use of the triazine-based condensing agent (IX). As the carboxylic acid having a polymerizable group, a carboxylic acid (a1) represented by the following formula (2) can be used preferably.

[Chem. 34]

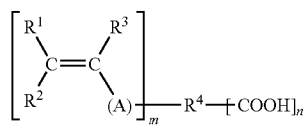

(2)

wherein $R^1$, $R^2$ and $R^3$ each independently are a hydrogen atom, a cyano group or a hydrocarbon group having 1 to 20 carbon atoms which may have a substituent; (A) is any constituent unit; A is one selected from the group consisting of —CONH—, —COO—, —OCO—, —O—, —S—, —CH$_2$O—, —CH$_2$S—, —C$_6$H$_4$O—, —C$_6$H$_4$CONH—, —C$_6$H$_4$NHCO—, —C$_6$H$_4$COO—, —C$_6$H$_4$OCO— and —CONHCO—; m is an integer of from 1 to 3; n is an integer of from 1 to 3; $R^4$ is an organic group having 1 to 40 carbon atoms which may have a substituent.

In the formula (2), $R^1$, $R^2$ and $R^3$ are not particularly limited unless they inhibit the condensation reaction of the present invention, and they each independently may employ a hydrogen atom, a cyano group or a hydrocarbon group having 1 to 20 carbon atoms which may have a substituent. Examples of the hydrocarbon group having 1 to 20 carbon atoms which may have a substituent include an alkyl group which may have a substituent, an alkenyl group which may have a substituent, an alkynyl group which may have a substituent, an aryl group which may have a substituent, an arylalkyl group which may have a substituent, an arylalkenyl group which may have a substituent, an arylalkynyl group which may have a substituent, and a cycloalkyl group which may have a substituent.

In the present invention, the alkyl group which may have a substituent is a straight-chain or branched-chain alkyl group which may have a substituent, and the alkyl groups provided as examples in the descriptions about $R^{12}$ and $R^{13}$ may be adopted as the alkyl group.

In the present invention, the alkenyl group which may have a substituent is a straight-chain or branched-chain alkenyl group which may have a substituent. Examples of the alkenyl group include a vinyl group, an allyl group, a methylvinyl group, a propenyl group, a butenyl group, a pentenyl group, a hexenyl group, a cyclopropenyl group, a cyclobutenyl group, a cyclopentenyl group and a cyclohexenyl group.

In the present invention, an alkynyl group which may have a substituent is a straight-chain or branched chain alkenyl group which may have a substituent, and examples of the alkenyl group include ethynyl, 1-propynyl, 2-propynyl, 1-butynyl, 1-methyl-2-propynyl, 2-butynyl, 3-butynyl, 1-pentynyl, 1-ethyl-2-propynyl, 2-pentynyl, 3-pentynyl, 1-methyl-2-butynyl, 4-pentynyl, 1-methyl-3-butynyl, 2-methyl-3-butynyl, 1-hexynyl, 2-hexynyl, 1-ethyl-2-butynyl, 3-hexynyl, 1-methyl-2-pentynyl, 1-methyl-3-pentynyl, 4-methyl-1-pentynyl, 3-methyl-1-pentynyl, 5-hexynyl, and 1-ethyl-3-butynyl.

In the present invention, the aryl group which may have a substituent is an aromatic hydrocarbon group which may have a substituent, and examples of the aryl group include a phenyl group, a naphthyl group, an anthryl group and a phenanthryl group.

In the present invention, the arylalkyl group which may have a substituent is an aryl-substituted straight-chain or branched-chain alkyl group which may have a substituent, and examples of the arylalkyl group include a benzyl group, a phenethyl group, a 3-phenylpropyl group, a trityl group, a 1-naphthylmethyl group, a 2-(1-naphthyl)ethyl group, a 2-(2-naphthyl)ethyl group and a 3-(2-naphthyl)propyl group.

In the present invention, the arylalkenyl group which may have a substituent is an aryl-substituted straight-chain or branched-chain alkenyl group which may have a substituent, and examples of the arylalkenyl group include a styryl group.

In the present invention, the arylalkynyl group which may have a substituent is an aryl-substituted straight-chain or branched-chain alkynyl group which may have a substituent, and examples of the arylalkynyl group include a phenylethynyl group.

In the present invention, the cycloalkyl group which may have a substituent is a cyclic alkyl group which may have a substituent, and examples of the cycloalkyl group include a cyclopropyl group, a cyclobutyl group, a cyclopentyl group, a cyclohexyl group, a cycloheptanyl group, a cyclooctanyl group, a cyclononanyl group, a cyclodecanyl group, a cycloundecanyl group and a cycldodecanyl group.

With respect to the formula (2), it is preferable that $R^1$ and $R^2$ are hydrogen atoms. This results in an advantage that the polymerizability is excellent. Moreover, with respect to the formula (2), it is preferable that $R^3$ is a hydrogen atom or a methyl group. This results in an advantage that the polymerizability is excellent. The case in which $R^1$ and $R^2$ are each a hydrogen atom and $R^3$ is a methyl group is advantageous in that a compound obtained by the production method of the present invention gives only a weak stimulation to a living body even if a polymerizable group has leaved from the compound due to an action of hydrolysis or the like.

In this embodiment, the number and the kind of the substituents which the hydrocarbon groups $R^1$, $R^2$ and $R^3$ have are not particularly limited. Embodiment in which there is a substituent between $R^1$, $R^2$ or $R^3$ and a double bond carbon are also included. It is preferable for $R^3$ that such a substituent is an ester bond. Examples of $R^3$ are the following:

[Chem. 35]

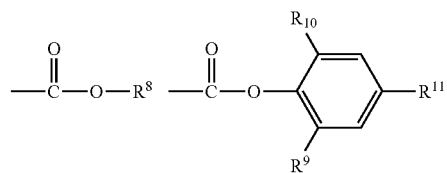

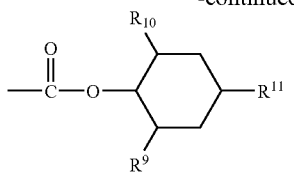

wherein $R^8$ is an alkyl group which may have a substituent, and $R^9$, $R^{10}$ and $R^{11}$ each independently are a hydrogen atom or an alkyl group which may have a substituent.

In the above-mentioned hydrocarbon groups having an ester bond, the alkyl groups provided as examples in the description of $R^{12}$ and $R^{13}$ may be adopted for $R^8$. When $R^8$ is an alkyl group, it is preferable, from the viewpoint of the polymerizability of the compound, that $R^8$ is an alkyl group having up to 4 carbon atoms, and more preferably is a methyl group or an ethyl group. $R^9$, $R^{10}$ and $R^{11}$ each independently are a hydrogen atom or an alkyl group which may have a substituent. For the alkyl group which may have a substituent, those provided as examples in the description of $R^{12}$ and $R^{13}$ may be adopted. When $R^9$, $R^{10}$ and $R^{11}$ are alkyl groups, it is preferable, from the viewpoint of the polymerizability of the compound, that they are alkyl groups having up to 4 carbon atoms, and more preferably are a methyl group, an ethyl group or a tert-butyl group.

In the formula (2), (A) is an arbitrary constituent unit. While A is one selected from the group consisting of —CONH—, —COO—, —OCO—, —O—, —S—, —CH$_2$O—, —CH$_2$S—, —C$_6$H$_4$O—, —C$_6$H$_4$CONH—, —C$_6$H$_4$NHCO—, —C$_6$H$_4$COO—, —C$_6$H$_4$OCO— and —CONHCO—, it is preferable from the viewpoint that radical polymerization easily occurs that A is —CONH— or —COO—. Moreover, when the compound obtained by the production method of the present invention is used for an embodiment in which the resistance to hydrolysis is particularly required, it is preferable that A is —CONH— or —CH$_2$O—.

In the formula (2), $R^4$ is an organic group having 1 to 40 carbon atoms which may have a substituent. As the $R^4$ in the formula (2), organic groups which are the same as those provided as examples in the description of the $R^4$ in the formula (1) can be used.

When the compound obtained by the production method of the present invention is a compound having an acidic group and a polymerizable group and also having an organic group as a spacer, the mechanism in which adhesive properties is developed in the case that the compound is used as an adhesive is not necessarily clear. Generally, it is believed that the development of adhesive properties needs that an acidic group chemically bonds to an object to be adhered and then a polymerizable group (co)polymerizes to form a coating film. It is believed to be important, for the purpose of obtaining a excellent adhesive properties, that a compound having an acidic group and a polymerizable group is arranged regularly when it bonds to an object to be adhered, so that it makes an effect densely to a surface for adhesion. The selection of the organic group to be used as a spacer is important for the purpose of arranging the compound regularly.

From such a viewpoint, the organic group is preferably a straight-chain aliphatic hydrocarbon group. One example of such a substituent is an alkylene group. From the viewpoint of increasing the adhesive properties, it is preferable that the acidic group and the polymerizable group are located at some distance from each other. The lower limit of the number of the carbon atoms in $R^4$ is preferably 4 or more, and more preferably 6 or more. Furthermore, when the compound obtained by the production method of the present invention is used as a component of a dental composition, the lower limit of the number of the carbon atoms in $R^4$ is even more preferably 7 or more, and particularly preferably 8 or more because the inside of the oral cavity is under a wet environment. By determining the number of the carbon atoms in $R^4$ within such a range, the hydrophobicity of the compound as a whole increases, so that it becomes resistant to hydrolysis even under a wet environment, for example, in the oral cavity and, as a result, it becomes possible to maintain a high adhesive properties for a longer period of time.

Moreover, when the compound obtained by the production method of the present invention is used as a component of a dental composition and is adhered to a tooth structure, it becomes necessary to provide a decalcification step by which the tooth structure surface is dissolved with an acidic component. There, however, is an advantage that the adjustment of the number of the carbon atoms in $R^4$ set within the foregoing range reduces the solubility to water of the calcium salt of the compound generated in the decalcification step, so that the adhesive properties further increases. The upper limit of the number of the carbon atoms in $R^4$ is not particularly limited. If, however, the number of the carbon atoms reaches a certain level, there is a tendency that no further effect on improvement in adhesive properties is developed even if the number of the carbon atoms is further increased. For this reason, from the viewpoint that raw materials can be obtained easily and so on, the upper limit of the number of the carbon atoms in $R^4$ is preferably 30 or less, more preferably 20 or less, even more preferably 18 or less, and particularly preferably 16 or less.

In the formula (2), m is an integer of from 1 to 3 and n is an integer of from 1 to 3. As described above, in order to regularly arrange the compound which has bonded to an object to be adhered, it is preferable that m=1 and n=1. The case where m=1 and n=1 is beneficial also in that the step required by the synthesis becomes shorter, leading to an advantage in cost. On the other hand, in the case that there is a wish to increase the number of points of action at which it chemically interacts with the object to be adhered, it is preferable that n is 2 or 3. This is effective particularly when the object to be adhered is metal or porcelain. Furthermore, also when there is a wish to increase the coating film strength by imparting crosslinkability to the compound obtained by the production method of the present invention, it is preferable that m is 2 or 3. As described above, the proper values of m and n differ according to the embodiments and may be selected arbitrarily depending on the embodiment.

In the production method of the present invention, it is preferable that the carboxylic acid (a1) represented by the formula (2) contains a (meth)acryl group or a (meth)acrylamide group. By containing a (meth)acryl)acryl group or a (meth)acrylamide) group, it becomes easier to undergo radical polymerization. When the compound obtained by the production method of the present invention is used as a component of a dental composition, the polymerizable group may leave due to hydrolysis or the like because the inside of the oral cavity is under a wet environment. With consideration to the resistance to hydrolysis, it is more preferable to use a (meth) acrylamide group as the polymerizable group. Furthermore, with consideration to the stimulativeness of a polymerizable group which has left to the living body, it is preferable to use a methacryl group or a methacrylamide group.

In the production method of the present invention, when the carboxylic acid is a carboxylic acid (a1) represented by the formula (2), the amine to be used in the execution of a condensation reaction is preferably an amine (b4) represented by the following formula (9):

[Chem. 36]

$$R^{18}-NH_2 \quad (9)$$

wherein $R^{18}$ is an organic group having 1 to 200 carbon atoms which may have a substituent.

In the amine (b4) represented by the formula (9), $R^{18}$ is an organic group having 1 to 200 carbon atoms which may have a substituent. The organic group may contain, in its structure, a bond other than a carbon-carbon bond, such as an ether bond, an ester bond, an amide bond, a sulfonyl bond, a urethane bond and a thioether bond. Moreover, it may also contain an aromatic ring, a double bond, a triple bond, an alicyclic hydrocarbon group, or a heterocycle. Furthermore, it may also have a substituent such as a halogen atom, a hydroxyl group, an amino group, a cyano group and a nitro group. For example, an amine in which many pyranose rings are linked like chitosan may be used as a substrate.

In the production method of the present invention, the amine (b4) represented by the formula (9) preferably is an amino acid, and particularly preferably is an amino acid having a hydroxyl group. Examples of such an amino acid include serine, threonine and tyrosine.

In addition, the amine (b4) represented by the formula (9) is preferably a phosphate of an amino acid. The phosphate of an amino acid is preferably a substance in which a phosphoric acid group is attached to a hydroxyl group of an amino acid having the hydroxyl group. The various amino acids described above may be employed as the amino acid. Specific examples include phosphoserine, a phosphothreonine, phosphotyrosine. It is also permissible to use, as the amine (b4) represented by the formula (9), polysaccharides having an amino group, which are represented by chitosan.

Amino acids, phosphates of amino acids and polysaccharides having an amino group are present extensively in the natural world. In particular, amino acids are also present extensively in the living body. In many cases, an amino acid having a hydroxyl group is phosphorylated in the living body to exist in the form of a phosphate of the amino acid. Therefore, the compound obtained by the production method of the polymerizable amide of the present invention by using the amine (b4) is advantageous in that even if decomposed products are formed by the action of hydrolysis or the like, the substances released through the decomposition are highly safe.

By causing the carboxylic acid (a1) represented by the formula (2) and the amine (b4) represented by the formula (9) to undergo condensation reaction together by the use of the triazine-based condensing agent (IX), a polymerizable amide (X) represented by the following formula (10) is obtained.

[Chem. 37]

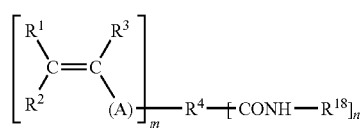

(10)

wherein $R^1$, $R^2$, $R^3$, $R^4$, $R^{18}$, (A), m and n are the same as those of the formula (2) and the formula (9).

In the method for producing the polymerizable amide of the present invention, the reaction proceeds in two stages as illustrated with a reaction formula below by taking as an example a case in which the triazine-based condensing agent (IX) represented by the formula (8), the carboxylic acid represented by the formula (2) and the amine represented by the formula (9) are used, m=1, n=1 and X is a chlorine atom. That is, in a first stage, a carboxylic acid represented by the following formula (2a) is attached to a triazine ring represented by the formula (8a), so that an ester intermediate represented by the following formula (2b) is generated, and simultaneously a morpholine represented by the following formula (8b) and hydrochloric acid are generated. Subsequently, in a second stage, an amine represented by the formula (9) acts on the ester intermediate represented by the following formula (2b), so that a polymerizable amide represented by the following formula (10a) is obtained and simultaneously a hydroxytriazine represented by the formula (8c) is generated. While a neutralizing agent or the like may be added in order to neutralize the hydrochloric acid produced at that reaction, it is not necessary to add a neutralizing agent and the reaction proceeds well because the hydrochloric acid is captured by the morpholine represented by the following formula (8b) which was produced in the first stage.

[Chem. 38]

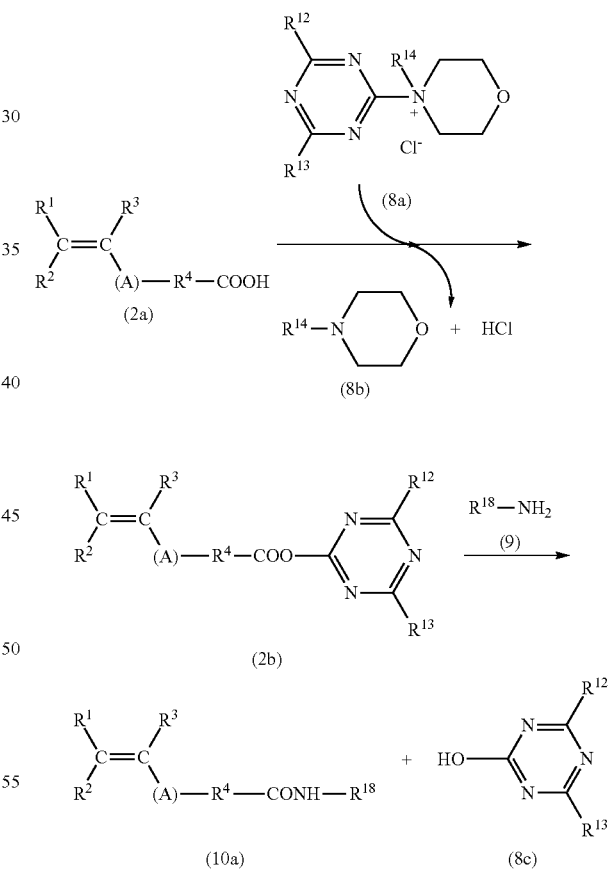

In a preferable production method of the present invention, it is possible to obtain a polymerizable amide (XI) by causing a carboxylic acid and an amine having a polymerizable group to undergo condensation reaction by the use of the triazine-based condensing agent (IX). As the amine having a polymerizable group, an amine (b3) represented by the following formula (12) can be preferably used.

[Chem. 39]

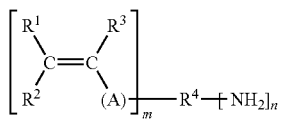

(12)

wherein $R^1$, $R^2$ and $R^3$ each independently are a hydrogen atom, a cyano group or a hydrocarbon group having 1 to 20 carbon atoms which may have a substituent; (A) is any constituent unit; A is one selected from the group consisting of —CONH—, —COO—, —OCO—, —O—, —S—, —CH$_2$O—, —CH$_2$S—, —C$_6$H$_4$O—, —C$_6$H$_4$CONH—, —C$_6$H$_4$NHCO—, —C$_6$H$_4$COO—, —C$_6$H$_4$OCO— and —CONHCO—; m is an integer of from 1 to 3; n is an integer of from 1 to 3; and $R^4$ is an organic group having 1 to 40 carbon atoms which may have a substituent.

In the amine (b3) represented by the formula (12), $R^1$, $R^2$, $R^3$, $R^4$, (A), m and n are the same as those of the formula (2), and those provided in the description of the formula (2) are employed.

In the production method of the present invention, it is preferable that the amine (b3) represented by the formula (12) contains a (meth)acryl group or a (meth)acrylamide group. By containing a (meth)acryl group or a (meth)acrylamide group, it becomes easier to undergo radical polymerization. When the compound obtained by the production method of the present invention is used as a component of a dental composition, the polymerizable group may leave due to hydrolysis or the like because the inside of the oral cavity is under a wet environment. With consideration to the resistance to hydrolysis, it is more preferable to use a (meth)acrylamide group as the polymerizable group. Furthermore, with consideration to the stimulativeness of a polymerizable group which has left to the living body, it is preferable to use a methacryl group or a methacrylamide group.

In the production method of the present invention, when the amine is an amine (b3) represented by the formula (12), the carboxylic acid to be used in the execution of a condensation reaction is preferably a carboxylic acid (a3) represented by the following formula (11):

[Chem. 40]

$$R^{19}—COOH \quad (11)$$

wherein $R^{19}$ is an organic group having 1 to 200 carbon atoms which may have a substituent.

In the carboxylic acid (a3) represented by the formula (11), $R^{19}$ is an organic group having 1 to 200 carbon atoms which may have a substituent. The organic group may contain, in its structure, a bond other than a carbon-carbon bond such as an ether bond, an ester bond, an amide bond, a sulfonyl bond, a urethane bond and a thioether bond. Moreover, it also may contain an aromatic ring, a double bond, a triple bond, an alicyclic hydrocarbon group, or a heterocycle. Furthermore, it also may have a substituent such as a halogen atom, a hydroxyl group, an amino group, a cyano group and a nitro group.

By causing the carboxylic acid (a3) represented by the formula (11) and the amine (b3) represented by the formula (12) to undergo condensation reaction together by the use of a triazine-based condensing agent (IX), a polymerizable amide (XI) represented by the following formula (13) is obtained.

[Chem. 41]

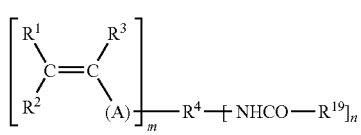

(13)

wherein $R^1$, $R^2$, $R^3$, $R^4$, $R^{19}$, (A), m and n are the same as those of the formula (11) and the formula (12).

In the method for producing the polymerizable amide of the present invention, the reaction proceeds in two stages as illustrated with a reaction formula below by taking as an example a case in which the triazine-based condensing agent (IX) represented by the formula (8), the carboxylic acid represented by the formula (11) and the amine represented by the formula (12) are used, m=1, n=1 and X is a chlorine atom. That is, in a first stage, a carboxylic acid represented by the formula (11) is attached to a triazine ring represented by the formula (8a), so that an ester intermediate represented by the following formula (11a) is generated, and simultaneously a morpholine represented by the following formula (8b) and hydrochloric acid are generated. Subsequently, in a second stage, an amine represented by the formula (12a) acts on the ester intermediate represented by the following formula (11a), so that a polymerizable amide represented by the following formula (8a) is obtained and simultaneously a hydroxytriazine represented by the formula (8c) is generated. While a neutralizing agent or the like may be added in order to neutralize the hydrochloric acid produced at that reaction, it is not necessary to add a neutralizing agent and the reaction proceeds well because the hydrochloric acid is captured by the morpholine represented by the following formula (8b) which was produced in the first stage.

[Chem. 42]

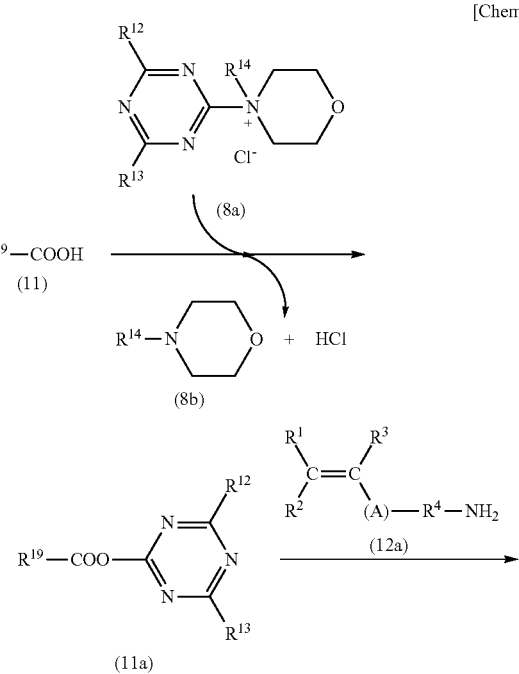

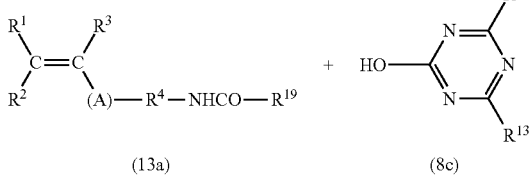

(13a)  (8c)

In the production method of the present invention, while the used amount of the triazine-based condensing agent (IX) is not particularly limited, it is preferable to use the triazine-based condensing agent (IX) at an amount of 0.5 to 2 mol relative to 1 mol of the carboxylic acid. If the used amount of the triazine-based condensing agent (IX) is less than 0.5 mol, a condensation reaction may become difficult to proceed and the reaction yield may decrease. The used amount of the triazine-based condensing agent (IX) is more preferably 0.6 mol or more, even more preferably 0.7 mol or more, and particularly preferably 0.8 mol or more relative to 1 mol of the carboxylic acid. On the other hand, if the used amount of the triazine-based condensing agent (IX) exceeds 2 mol relative to 1 mol of the carboxylic acid, the reactivity may become so high that an amino group-containing compound may further react with a carboxyl group in the molecule of a resulting compound and, as a result, the reaction yield may decrease. From such a viewpoint, the used amount of the triazine-based condensing agent (IX) is more preferably 1.8 mol or less, even more preferably 1.6 mol or less, and particularly preferably 1.4 mol or less relative to 1 mol of the carboxylic acid.

In the production method of the present invention, while the method of causing the carboxylic acid and the amine to react is not particularly limited, it is preferable to cause them to react while stirring them. At this time, the timing of adding the triazine-based condensing agent (IX), the carboxylic acid and the amine is not particularly limited. It is permissible to add them simultaneously to the reaction system and then mix them. It is also permissible to add them sequentially. In the use of a carbodiimide-based condensing agent like DCC, it is necessary to cause a carboxylic acid and a condensing agent to react together first and then add an amine because the condensing agent can react with both the carboxylic acid and the amine. The yield may decrease depending upon the timing of the addition of the amine. On the other hand, the triazine-based condensing agent (IX) to be used in the present invention is advantageous in that no consideration about the timing of its addition is needed because it reacts selectively with only a carboxylic acid and does not react with an amine, and therefore a polymerizable amide can be obtained at a high yield. It is preferable that the carboxylic acid and the amine have been dissolved completely when the triazine-based condensing agent (IX) is added. This leads to rapid proceeding of a condensation reaction.

In the production method of the present invention, while an embodiment in which a triazine-based condensing agent (IX) is added to a reaction system so as to cause a carboxylic acid and an amine to react together is available described above, an embodiment in which a triazine-based condensing agent (IX) is generated in a reaction system by adding a triazine compound like 2-chloro-4,6-dimethoxy-1,3,5-triazine (CDMT) and a tertiary amine like dimethylglycine ethyl ester (DMGE) into the reaction system and then a carboxylic acid and an amine are caused to react together is also available. The addition of the tertiary amine to the triazine compound causes the condensation reaction to proceed rapidly.

While the used amount of the triazine compound used in the preparation of the triazine-based condensing agent (IX) is not particularly limited, it is preferable to use the triazine compound at an amount of 0.5 to 2 mol, more preferably at an amount of 0.7 to 1.5 mol relative to 1 mol of the carboxylic acid. While the used amount of the tertiary amine is not particularly limited, the tertiary amine serves as a catalyst in the reaction system and, therefore, it is not necessary to add the amine at an equimolar amount with the triazine compound. For this reason, in view of the merit in cost, it is preferable to use a tertiary amine at an amount of 0.05 to 0.5 mol, more preferably at an amount of 0.1 to 0.3 mol relative to 1 mol of the triazine compound.

In the production method of the present invention, the reaction temperature during the process of causing the carboxylic acid and the amine to react is not particularly limited, and it may be adjusted appropriately depending upon the kind of the carboxylic acid or the amine to be used and the reaction solvent. The use of the triazine-based condensing agent is advantageous in that it is possible to cause a reaction to proceed smoothly even at room temperature and, therefore, it is possible to carry out the reaction under very mild conditions. With respect to the reaction temperature, a temperature of 10 to 60° C. is ordinarily used, and the reaction temperature is preferably 15 to 45° C.

In the production method of the present invention, the reaction time during the process of causing the carboxylic acid and the amine to react is not particularly limited, and it may be adjusted appropriately depending upon the kind of the carboxylic acid or the amine to be used and the reaction solvent. It is ordinarily 10 minutes to 24 hours, and is preferably 20 minutes to 16 hours.

In the production method of the present invention, it is preferable to execute the reaction under neutral conditions. The reaction may not proceed under acidic conditions. Under basic conditions, an amide bond in the resulting compound may be hydrolyzed. Therefore, in the production method of the present invention, the pH of the reaction system is preferably 6.5 to 8, more preferably 7 to 8, and particularly preferably 7 to 7.6.

While the reaction solvent to be used in the production method of the present invention is not particularly limited, it is preferable that the reaction solvent contains water. Usually, in condensation reactions by which an ester bond or an amide bond is formed, water is a substance which is to be removed. If water is present, the reaction efficiency often decreases. On the other hand, in the production method of the present invention, the reaction proceeds without decrease in reaction efficiency. Moreover, amidation can be accomplished by the use of a compound which is hardly-soluble in organic solvents other than water, e.g., a dicarboxylic acid, and it also excels in the field of environmental protection.

The organic solvent to be used as a reaction solvent includes halogen-containing solvents such as methylene chloride and chloroform; hydrocarbon solvents such as hexane and toluene; ester solvents such as ethyl acetate; ether solvents such as diethyl ether, diisopropyl ether and tetrahydrofuran; acetonitrile; dimethylformamide (DMF); dimethyl sulfoxide (DMSO); and alcohol solvents such as methanol, ethanol and isopropanol. Among them, at least one selected from the group consisting of ester solvents, ether solvents and alcohol solvents is preferred, and particularly the use of an alcohol solvent is preferred from the viewpoint that it is possible to cause the triazine-based condensing agent (IX) to exist with stability. It is known that it is more difficult to use alcohol than water because when alcohol is used as a reaction solvent, a competitive reaction where the solvent alcohol and a carboxylic acid produce an ester occurs. In the production method of the present invention, alcohol can be used as a reaction solvent if the triazine-based condensing agent (IX) is used, because the amide formation is extremely higher in selectivity than the ester formation. When alcohol is used, it is more useful than organic solvents which are relatively high in boiling point, like DMF and DMSO, because a wider variety of compounds are soluble therein in comparison to water, the solvent can be removed easily because of its low boiling point, or it is less expensive.

The alcohol to be used in the production method of the present invention is not particularly limited, and examples thereof include aliphatic alcohols such as methanol, ethanol, n-propanol, 2-propanol, n-butanol, 2-butanol, cyclopropanol, cyclopentanol and cyclohexanol; and aromatic alcohols such as phenol, m-cresol and benzyl alcohol. These alcohols may be used singly or in combination of two or more of them. When a mixed solvent of water and alcohol is used as a reaction solvent, it is preferable, from the viewpoint of the miscibility with water, to use at least one selected from the group consisting of methanol, ethanol, n-propanol and 2-propanol. The use of methanol is particularly preferred from the viewpoint that it easily dissolves a carboxylic acid and the solvent can be removed easily due to its low boiling point.

In the production method of the present invention, the reaction solvent to be used for a condensation reaction is preferably a mixed solvent of water and alcohol. It can be used with an appropriate adjustment of the mixed ratio of the alcohol to the water depending upon the solubility of the reactants, the mixed ratio of the alcohol to the water (alcohol/water) is preferably 9/1 to 1/9, more preferably 8/2 to 2/8, and even more preferably 8/2 to 5/5.

The polymerizable amide obtained by the production method of the present invention can be used as a raw material of a dental composition. When the polymerizable amide obtained has a phosphoric acid group or a carboxyl group, it can be particularly preferably used. The dental composition includes primer, bonding material, composite resin, cement (resin cement, glass ionomer cement, resin-reinforced glass ionomer cement), fissure sealant, and resin for denture bases. In particular, when the polymerizable amide obtained by the production method of the present invention is a compound (I) represented by the formula (1), the dental composition containing the compound (I) can be preferably used as a primer, a bonding material, a composite resin, or a cement as described above.

In addition, the polymerizable amide obtained by the production method of the present invention is also useful for applications other than dental applications, such as bone cement, building adhesive, adhesive for ceramic ware, sealant and coating material.

EXAMPLES

The present invention is illustrated below more concretely with reference to examples.

Synthesis of N-methacryloyl-12-aminododecanoic acid

To a 5000 mL beaker, 1700 mL of water was added and then 11 g of sodium hydroxide was added, followed by stirring to dissolve the sodium hydroxide completely. Then, 26.9 g of 12-aminododecanoic acid (produced by Wako Pure Chemical Industries, Ltd.) was added to the reaction system, followed by stirring for 30 minutes to obtain a homogeneous solution. Subsequently, the internal temperature of the reaction system was cooled to −5° C. with an ice-salt bath. After the cooling treatment, 14.3 g of methacryloyl chloride (produced by Wako Pure Chemical Industries, Ltd.) was dropped over 15 minutes with a dropping funnel while stirring the reaction system. During the dropping, cooling was continued so that the internal temperature of the reaction system might not exceed 0° C. After the end of the dropping, the bath was changed to an ice bath and the reaction system was stirred at 0° C. for 1 hour. After stirring for 1 hour, a 6 mol/L aqueous hydrochloric acid solution was added to adjust the pH of the reaction solution at 3 or less. With the addition of the aqueous hydrochloric acid solution, white precipitate formed in the reaction system. To the solution was added 600 g of sodium chloride, and then extraction was carried out three times using 800 mL of ethyl acetate. The resulting ethyl acetate solution was washed with saturated aqueous sodium chloride solution and then magnesium sulfate was added to the ethyl acetate layer to dehydrate it. After the dehydration, ethyl acetate was distilled off under reduced pressure with a rotary evaporator to give white crude crystals. The resulting crude crystals were recrystallized from ethyl acetate to give 24 g of white crystals of N-methacryloyl-12-aminododecanoic acid (melting point: 73 to 74° C.). The chemical reaction formula of this Example is shown below.

[Chem. 43]

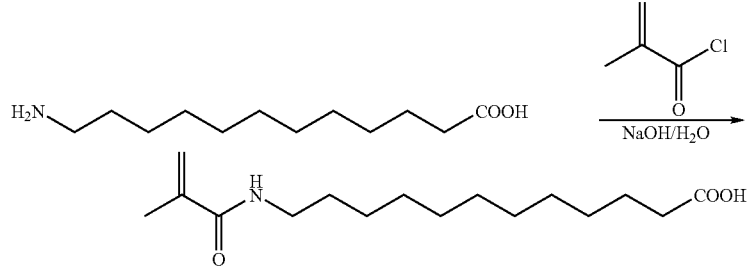

Synthesis of polymerizable amide, compound (I)

To a 1000 mL beaker, 10 of N-methacryloyl-12-aminododecanoic acid obtained by the aforementioned method and 6.3 g of phosphoserine (produced by Tokyo Chemical Industry Co., Ltd.) were added. Then, 500 ml of a mixed solvent of methanol and water (volume ratio of methanol to water (methanol/water)=7/3) was added, and was mixed with a stirring bar. A pH meter ("pH meter F-55" manufactured by HORIBA, Ltd.) was set into the solution. When 20 mL of a 2 mol/L aqueous sodium hydroxide solution was added, it became a colorless, transparent homogeneous solution. At this time, the pH was 6.4. When 3.5 mL of a 6 mol/L aqueous sodium hydroxide solution was added additionally, the pH was 7.4. Then, 10.67 g of 4-(4,6-dimethoxy-1,3,5-triazin-2-yl)-4-methylmorpholinium chloride ("DMT-MM" produced by Kokusan Chemical Co., Ltd. (water content 12%); this hereinafter may be abbreviated as "DMT-MM") was added gradually with a spatula, followed by stirring at room temperature for 16 hours. The added amount of the DMT-MM was 0.96 mol relative to 1 mol of N-methacryloyl-12-aminododecanoic acid. Subsequently, 50 mg of methyl ether hydroquinone (this may be abbreviated as "MEHQ") as a polymerization inhibitor was added, and then the reaction solution was transferred to a 2000 mL recovery flask. The methanol in the reaction solution was distilled off under reduced pressure at a bath temperature of 25° C. with a rotary evaporator. The concentrated solution remaining after the distillation under reduced pressure was transferred to a 1000 mL separating funnel, and then 200 mL of water was added, so that the entire amount of the water layer was adjusted at about 400 mL. To the separating funnel was added 100 mL of ethyl acetate, and the water layer was washed with the ethyl acetate three times. To the water layer in the separating funnel was added 150 mL of a 1 mol/L aqueous hydrochloric acid solution, and then the separating funnel was shaken to give white emulsion. The pH of the aqueous layer was 1.3. About 550 mL of a water layer obtained by the procedures described above was extracted with 400 mL of ethyl acetate five times to give an organic layer containing the target compound (by strongly acidifying the pH of the water layer, the target compound becomes prone to be extracted to the organic layer). To the resulting organic layer was added 50 mg of MEHQ, and then the organic layer was concentrated under reduced pressure at a bath temperature of 25° C. with a rotary evaporator. After the completion of the concentration, white oily substance settled on the bottom of the flask. To the oily substance, 75 mL of methanol was added to dissolve the substance, and then the resulting methanol solution was filtered through a cotton plug. Subsequently, the filtrate was concentrated under reduced pressure at a temperature of 25° C. with a rotary evaporator to give 8.8 g of compound (I) of the present invention, which was the target polymerizable amide. The chemical reaction formula of this Example is shown below.

The $^1$H-NMR spectrum (400 MHz, CD$_3$OD) of the compound (I) obtained by the above-described method was measured. The chemical shifts δ (ppm, TMS) were as follows:
δ=1.31 (s; 14H), 1.53 (t; 2H), 1.62 (t; 2H), 1.93 (s; 3H), 2.27 (m; 2H), 3.21 (t; 2H), 4.11 (m; 1H), 4.23 (m; 1H), 4.57 (t; 1H), 5.34 (s; 1H), 5.65 (s; 1H)

The $^{13}$C-NMR spectrum (100 MHz, CD$_3$OD) of the compound (I) obtained by the above-described method was measured. The chemical shifts δ (ppm) were as follows:
δ=18.9, 26.8, 28.0, 30.2, 30.3, 30.4, 30.5, 30.6, 36.8, 40.6, 52.8, 54.9, 65.5, 120.0, 141.3, 151.4, 171.0, 171.7, 176.2

The abbreviations used below are as follows:
[Acidic Monomer]
  A-1: Compound (I)
  A-2: N-Methacryloyl-12-aminododecanoic acid
  A-3: 2-Methacryloyloxyethylphosphoric acid
[Water-Soluble Polymerizable Monomer]
  HEMA: 2-Hydroxyethyl methacrylate
[Crosslinkable Polymerizable Monomer]
  BisGMA: Bisphenol A diglycidyl methacrylate
  #801: 1,2-Bis(3-methacryloyloxy-2-hydroxypropyloxy)ethane
  NPG: Neopentyl glycol dimethacrylate
[Photopolymerization Initiator]
  TMDPO: 2,4,6-Trimethylbenzoyldiphenylphosphine oxide
  CQ: Camphorquinone
[Amines]
  Amine 1: n-Butoxyethyl N,N-dimethylaminobenzoate
  Amine 2: Triethanolamine
[Inorganic Filler]
  Inorganic filler 1: "R972" produced by Japan Aerosil
  Inorganic filler 2: "Ar380" produced by Japan Aerosil
[Preparation of Two-Bottle Type Dental Composition]

Example 1

A primer composition and a bonding material composition were prepared by mixing the components given below at normal temperature, and then the bond strength to the bovine enamel and the bond strength to the bovine dentin were measured.

[Chem. 44]

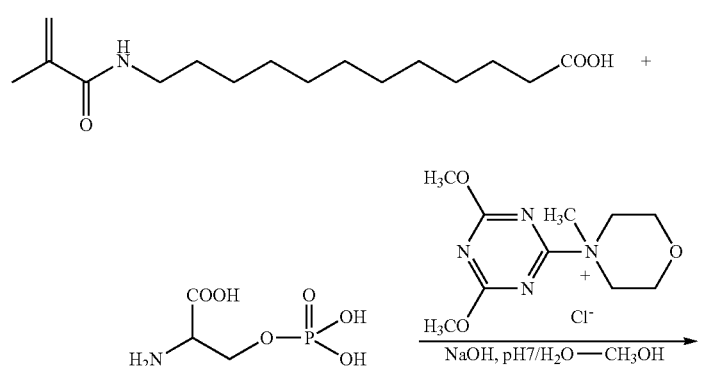

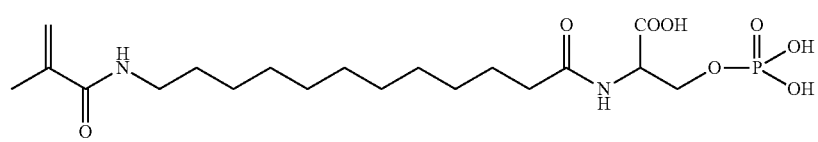

Primer Composition:

| | |
|---|---|
| A-1 | 15 parts by weight |
| HEMA | 40 parts by weight |
| Water | 40 parts by weight |
| #801 | 10 parts by weight |
| Ethanol | 8 parts by weight |
| TMDPO | 0.5 parts by weight |

Bonding Material Composition:

| | |
|---|---|
| BisGMA | 40 parts by weight |
| HEMA | 40 parts by weight |
| NPG | 20 parts by weight |
| TMDPO | 3 parts by weight |
| Inorganic filler 1 | 5.5 parts by weight |
| Inorganic filler 2 | 1.5 parts by weight |

[Evaluation Method of Adhesion to Bovine Enamel and Bovine Dentin]

The labial surface of a bovine mandibular incisor was polished with #80 silicon carbide paper (manufactured by Nihon Kenshi Co., Ltd.) under running water, so that a sample with an exposed flat surface of the enamel and a sample with an exposed flat surface of the dentin were obtained, respectively. Each of the samples obtained was further polished with #1000 silicon carbide paper (manufactured by Nihon Kenshi Co., Ltd.) under running water. After the completion of the polishing, the water on the surface was dried by air-blowing. An adhesive tape with a thickness of approximately 150 μm having a round hole with a diameter of 3 mm was adhered onto the smooth surface after the drying, thereby restricting the adhesion area.

The primer composition prepared above was applied within the round hole with a brush, followed by being left at rest for 20 seconds. Then, the surface was dried by air-blowing until the primer composition applied lost its fluidity. Subsequently, the bonding material composition was applied on the tooth surface where the primer had applied and dried. Then, the resultant was irradiated with light for 20 seconds with a dental visible light irradiator "JET LIGHT 3000" (manufactured by J. Morita USA), thereby curing the primer composition and the bonding material composition applied.

The surface of the resulting cured bonding material composition was coated with a composite resin for dental filling (produced by Kuraray Medical Inc., trade name "Clearfil AP-X" (registered trademark)), and then it was covered with a release film (polyester). Subsequently, a slide glass was placed on and pressed against the release film, so that the applied surface of the composite resin was smoothened. Then, the composite resin was irradiated with light through the release film for 20 seconds by the use of the irradiator "JET LIGHT 3000", so that the composite resin was cured.

To the surface of the resulting cured composite resin for dental filling, one end face (circular section) of a cylindrical bar made of stainless steel (7 mm in diameter and 2.5 cm in length) was adhered with a commercially available dental resin cement (produced by Kuraray Medical Inc., trade name "PANAVIA 21"). After the adhering, the sample was left at rest at room temperature for 30 minutes, and then was immersed in distilled water. The resulting sample which had been immersed in distilled water was placed at rest for 24 hours in a thermostat held at 37° C., so that a test sample for an adhering test was prepared. Five test samples for adhering test were prepared.

[Measurement of Bond Strength]

The tensile bond strengths of the five test samples for adhesive test were measured with a universal testing machine (manufactured by Shimadzu Corporation) at a cross head speed set at 2 mm/min. The average of the measurements was used as the tensile bond strength. The bond strength to the bovine enamel was 25.0 MPa, and the bond strength to the bovine dentin was 18.4 MPa. The results obtained are summarized in Table 1.

Comparative Example 1

A primer composition and a bonding material composition were prepared in the same manner as in Example 1 except for using 15 parts by weight of "A-2" instead of using 15 parts by weight of the acidic monomer "A-1" in Example 1, and then the bond strength to the bovine enamel and the bond strength to the bovine dentin were measured. The results obtained are summarized in Table 1.

Comparative Example 2

A primer composition and a bonding material composition were prepared in the same manner as in Example 1 except for using 15 parts by weight of "A-3" instead of using 15 parts by weight of the acidic monomer "A-1" in Example 1, and then the bond strength to the bovine enamel and the bond strength to the bovine dentin were measured. The results obtained are summarized in Table 1.

[Preparation of One-Bottle Dental Composition]

Example 2

A one-bottle bonding material composition, which was a one-bottle dental composition, was prepared by mixing the components given below, and then the bond strength to the bovine dentin was measured.

One-Bottle Bonding Material Composition:

| | |
|---|---|
| A-1 | 10 parts by weight |
| BisGMA | 30 parts by weight |
| HEMA | 30 parts by weight |
| Water | 15 parts by weight |
| Ethanol | 15 parts by weight |
| TMDPO | 5 parts by weight |
| Inorganic filler 1 | 5 parts by weight |

[Evaluation Method of Adhesion to Bovine Enamel and Bovine Dentin]

The labial surface of a bovine mandibular incisor was polished with #80 silicon carbide paper (manufactured by Nihon Kenshi Co., Ltd.) under running water, so that a sample with an exposed flat surface of the enamel and a sample with an exposed flat surface of the dentin were obtained. Each of the samples obtained was further polished with #1000 silicon carbide paper (manufactured by Nihon Kenshi Co., Ltd.) under running water. After the completion of the polishing, the water on the surface was dried by air-blowing. An adhesive tape with a thickness of approximately 150 μm having a round hole with a diameter of 3 mm was adhered onto the smooth surface after the drying, thereby restricting the adhesion area.

The one-bottle bonding material composition prepared above was applied within the round hole with a brush, followed by being left at rest for 20 seconds. Then, the surface was dried by air-blowing until the one-bottle bonding material composition applied lost its fluidity. Then, the resultant was irradiated with light for 20 seconds with a dental visible light irradiator "JET LIGHT 3000" (manufactured by J. Morita USA), thereby curing the one-bottle bonding material composition applied.

The surface of the cured one-bottle bonding material composition was coated with a composite resin for dental filling (produced by Kuraray Medical Inc., trade name "Clearfil AP-X" (registered trademark)), and then it was covered with a release film (polyester). Subsequently, a slide glass was placed on and pressed against the release film, so that the applied surface of the composite resin was smoothened. Then, the composite resin was irradiated with light through the release film for 20 seconds by the use of the irradiator "JET LIGHT 3000", so that the composite resin was cured.

To the surface of the resulting cured composite resin for dental filling, one end face (circular section) of a cylindrical bar made of stainless steel (7 mm in diameter and 2.5 cm in length) was adhered with a commercially available dental resin cement (produced by Kuraray Medical Inc., trade name "PANAVIA 21"). After the adhering, the sample was left at rest at room temperature for 30 minutes, and then was immersed in distilled water. The resulting sample which had been immersed in distilled water was placed at rest for 24 hours in a thermostat held at 37° C., so that a test sample for an adhering test was prepared. Five test samples for adhering test were prepared.

[Measurement of Bond Strength]

The tensile bond strengths of the five test samples for adhesive test were measured with a universal testing machine (manufactured by Shimadzu Corporation) at a cross head speed set at 2 mm/min. The average of the measurements was used as the tensile bond strength. The bond strength to the bovine enamel was 16.8 MPa, and the bond strength to the bovine dentin was 20.7 MPa. The results obtained are summarized in Table 2.

Comparative Example 3

A one-bottle bonding material composition was prepared in the same manner as in Example 2 except for using 10 parts by weight of "A-2" instead of using 10 parts by weight of the acidic monomer "A-1" in Example 2, and then the bond strength to the bovine enamel and the bond strength to the bovine dentin were measured. The results obtained are summarized in Table 2.

Comparative Example 4

A one-bottle bonding material composition was prepared in the same manner as in Example 2 except for using 10 parts by weight of "A-3" instead of using 10 parts by weight of the acidic monomer "A-1" in Example 2, and then the bond strength to the bovine enamel and the bond strength to the bovine dentin were measured. The results obtained are summarized on Table 2.

TABLE 1

|  | Acidic monomer | Bond strength to enamel (MPa) | Bond strength to dentin (MPa) |
| --- | --- | --- | --- |
| Example 1 | A-1 | 25.0 | 18.4 |
| Comparative Example 1 | A-2 | 1.6 | 5.3 |
| Comparative Example 2 | A-3 | 11.7 | 8.9 |

TABLE 2

|  | Acidic monomer | Bond strength to enamel (MPa) | Bond strength to dentin (MPa) |
| --- | --- | --- | --- |
| Example 2 | A-1 | 16.8 | 20.7 |
| Comparative Example 3 | A-2 | 1.7 | 3.7 |
| Comparative Example 4 | A-3 | 0.4 | 6.3 |

Example 3

A one-bottle bonding material composition was prepared in the same manner as in Example 2 except for changing the composition of the one-bottle bonding material composition as given below in Example 2, and then the bond strength to the bovine enamel and the bond strength to the bovine dentin were measured. The bond strength to the bovine enamel was 16.1 MPa, and the bond strength to the bovine dentin was 21.4 MPa.

One-Bottle Bonding Material Composition:

| A-1 | 10 parts by weight |
| --- | --- |
| BisGMA | 30 parts by weight |
| HEMA | 30 parts by weight |
| Water | 15 parts by weight |
| Ethanol | 15 parts by weight |
| CQ | 3 parts by weight |
| Amine 1 | 1 part by weight |
| Amine 2 | 1.5 parts by weight |
| Inorganic filler 1 | 5 parts by weight |

Table 1 shows that in Example 1 where a compound (I) of the present invention, which was "A-1," was used as an acidic monomer, the bond strength of the composite resin to the enamel was 25.0 MPa and the bond strength of the composite resin to the dentin was 18.4 MPa. That is, the adhesive properties was excellent, and therefore, it is useful as a two-bottle dental adhesive. On the other hand, in both Comparative Example 1 where "A-2" having no phosphoric acid group was used as an acidic monomer and Comparative Example 2 where "A-3" having no carboxylic acid was used as an acidic monomer, the bond strength of the composite resin to the enamel and the bond strength of the composite resin to the dentin were greatly poor.

Table 2 shows that in Example 2 where a compound (I) of the present invention, which was "A-1," was used as an acidic monomer, the bond strength of the composite resin to the enamel was 16.8 MPa and the bond strength of the composite resin to the dentin was 20.7 MPa. That is, the adhesive properties was excellent, and therefore, it is useful as a one-bottle dental composition. On the other hand, in Comparative Example 1 where "A-2" having no phosphoric acid group was used as an acidic monomer and in Comparative Example 2 where "A-3" having no carboxylic acid was used as an acidic monomer, the bond strength of the composite resin to the dentin was greatly poor. It is also shown that in Example 3 which was directed not to the use of a polymerization initiator (III) alone but to the use of a polymerization initiator (III) and a polymerization accelerator (IV) in combination, excellent adhesive properties was exhibited and therefore it is useful as a one-bottle dental composition.

The invention claimed is:

1. A compound (I) represented by formula (1):

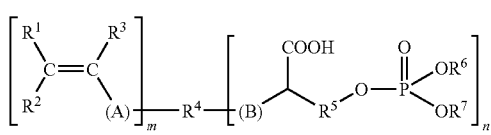

wherein
- $R^1$, $R^2$ and $R^3$ each independently are a hydrogen atom, a cyano group, a hydrocarbon group having 1 to 20 carbon atoms, or a substituted hydrocarbon group having 1 to 20 carbon atoms;
- A is —CONH— or —COO—;
- B is one selected from the group consisting of —CONH—, —NHCO—, —COO— and —OCO—;
- m is an integer of from 1 to 3;
- n is an integer of from 1 to 3;
- $R^4$ is an organic group having 1 to 40 carbon atoms or a substituted organic group having 1 to 40 carbon atoms;
- $R^5$ is a hydrocarbon group having 1 to 20 carbon atoms or a substituted hydrocarbon group having 1 to 20 carbon atoms;
- $R^6$ and $R^7$ each independently are a hydrogen atom, a hydrocarbon group having 1 to 20 carbon atoms, a substituted hydrocarbon group having 1 to 20 carbon atoms, or a metal atom.

2. The compound (I) of claim 1, wherein $R^1$ and $R^2$ are each a hydrogen atom and $R^3$ is a hydrogen atom or a methyl group.

3. The compound (I) of claim 1, wherein A is —CONH—.

4. The compound (I) of claim 1, wherein B is —CONH—.

5. The compound (I) of claim 1, wherein $R^5$ is one selected from the group consisting of —CH$_2$-Ph-, —CH(CH$_3$)— and —CH$_2$—.

6. A composition comprising a compound (I) represented by formula (1):

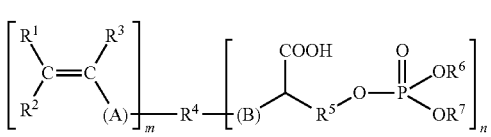

wherein
- $R^1$, $R^2$ and $R^3$ each independently are a hydrogen atom, a cyano group, a hydrocarbon group having 1 to 20 carbon atoms, or a substituted hydrocarbon group having 1 to 20 carbon atoms;
- A is one selected from the group consisting of —CONH—, —COO—, —OCO—, —O—, —S—, —CH$_2$O—, —CH$_2$S—, —C$_6$H$_4$O—, —C$_6$H$_4$CONH—, —C$_6$H$_4$NHCO—, —C$_6$H$_4$COO—, —C$_6$H$_4$OCO— and —CONHCO—;
- B is one selected from the group consisting of —CONH—, —NHCO—, —COO— and —OCO—;
- m is an integer of from 1 to 3;
- n is an integer of from 1 to 3;
- $R^4$ is an organic group having 1 to 40 carbon atoms or a substituted organic group having 1 to 40 carbon atoms;
- $R^5$ is a hydrocarbon group having 1 to 20 carbon atoms or a substituted hydrocarbon group having 1 to 20 carbon atoms;
- $R^6$ and $R^7$ each independently are a hydrogen atom, a hydrocarbon group having 1 to 20 carbon atoms, a substituted hydrocarbon group having 1 to 20 carbon atoms, or a metal atom,
- and a polymerizable monomer (II) which is other than the compound (I) and which can be copolymerized with the compound (I).

7. A composition comprising compound (I) represented by formula (1):

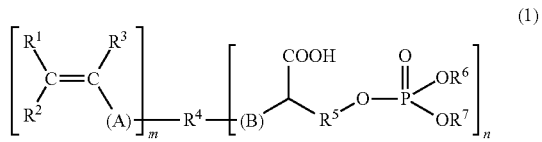

wherein
- $R^1$, $R^2$ and $R^3$ each independently are a hydrogen atom, a cyano group, a hydrocarbon group having 1 to 20 carbon atoms, or a substituted hydrocarbon group having 1 to 20 carbon atoms;
- A is one selected from the group consisting of —CONH—, —COO—, —OCO—, —O—, —S—, —CH$_2$O—, —CH$_2$S—, —C$_6$H$_4$O—, —C$_6$H$_4$CONH—, —C$_6$H$_4$NHCO—, —C$_6$H$_4$COO—, —C$_6$H$_4$OCO— and —CONHCO—;
- B is one selected from the group consisting of —CONH—, —NHCO—, —COO— and —OCO—;
- m is an integer of from 1 to 3;
- n is an integer of from 1 to 3;
- $R^4$ is an organic group having 1 to 40 carbon atoms or a substituted organic group having 1 to 40 carbon atoms;
- $R^5$ is a hydrocarbon group having 1 to 20 carbon atoms or a substituted hydrocarbon group having 1 to 20 carbon atoms;
- $R^6$ and $R^7$ each independently are a hydrogen atom, a hydrocarbon group having 1 to 20 carbon atoms, a substituted hydrocarbon group having 1 to 20 carbon atoms, or a metal atom,
- said composition further comprising at least one of the following:
  - a polymerization initiator (III),
  - a polymerization accelerator (IV),
  - and a filler (V).

8. The composition of claim 6, wherein the polymerizable monomer (II) is a (meth)acrylate compound.

9. The composition of claim 7, which comprises said polymerization initiator (III).

10. The composition of claim 7, which comprises said polymerization accelerator (IV).

11. The composition of claim 7, which comprises said filler (V).

12. The composition of claim 7, which comprises said solvent (VI).

13. The composition of claim 12, wherein the solvent (VI) comprises water (VII).

14. A primer comprising the composition of claim 6, a compound (I) represented by formula (1):

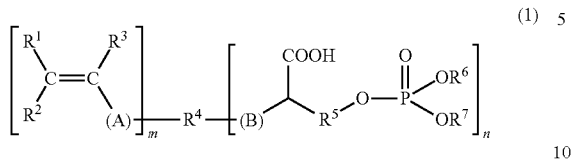

wherein
- $R^1$, $R^2$ and $R^3$ each independently are a hydrogen atom, a cyano group, a hydrocarbon group having 1 to 20 carbon atoms, or a substituted hydrocarbon group having 1 to 20 carbon atoms;
- A is one selected from the group consisting of —CONH—, —COO—, —OCO—, —O—, —S—, —CH$_2$O—, —CH$_2$S—, —C$_6$H$_4$O—, —C$_6$H$_4$CONH—, —C$_6$H$_4$NHCO—, —C$_6$H$_4$COO—, —C$_6$H$_4$OCO— and —CONHCO—;
- B is one selected from the group consisting of —CONH—, —NHCO—, —COO— and —OCO—;
- m is an integer of from 1 to 3;
- n is an integer of from 1 to 3;
- $R^4$ is an organic group having 1 to 40 carbon atoms or a substituted organic group having 1 to 40 carbon atoms;
- $R^5$ is a hydrocarbon group having 1 to 20 carbon atoms or a substituted hydrocarbon group having 1 to 20 carbon atoms;
- $R^6$ and $R^7$ each independently are a hydrogen atom, a hydrocarbon group having 1 to 20 carbon atoms, a substituted hydrocarbon group having 1 to 20 carbon atoms, or a metal atom.

15. A bonding material comprising the composition of claim 6, a compound (I) represented by formula (1):

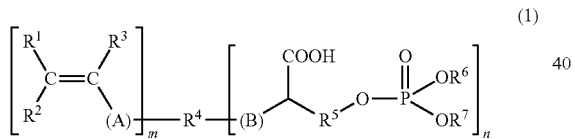

wherein
- $R^1$, $R^2$ and $R^3$ each independently are a hydrogen atom, a cyano group, a hydrocarbon group having 1 to 20 carbon atoms, or a substituted hydrocarbon group having 1 to 20 carbon atoms:
- A is one selected from the group consisting of —CONH—, —COO—, —OCO—, —O—, —S—, —CH$_2$O—, —CH$_2$S—, —C$_6$H$_4$O—, —C$_6$H$_4$CONH—, —C$_6$H$_4$NHCO—, —C$_6$COO—, —C$_6$H$_4$OCO— and —CONHCO—;
- B is one selected from the group consisting of —CONH—, —NHCO—, —COO— and —OCO—;
- m is an integer of from 1 to 3;
- n is an integer of from 1 to 3;
- $R^4$ is an organic group having 1 to 40 carbon atoms or a substituted organic group having 1 to 40 carbon atoms;
- $R^5$ is a hydrocarbon group having 1 to 20 carbon atoms or a substituted hydrocarbon group having 1 to 20 carbon atoms;
- $R^6$ and $R^7$ each independently are a hydrogen atom, a hydrocarbon group having 1 to 20 carbon atoms, a substituted hydrocarbon group having 1 to 20 carbon atoms, or a metal atom.

16. A cement comprising the composition of claim 6, a compound (I) represented by formula (1):

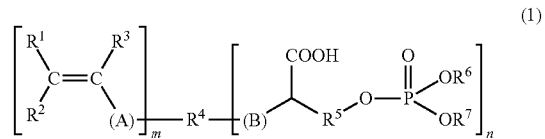

wherein
- $R^1$, $R^2$ and $R^3$ each independently are a hydrogen atom, a cyano group, a hydrocarbon group having 1 to 20 carbon atoms, or a substituted hydrocarbon group having 1 to 20 carbon atoms;
- A is one selected from the group consisting of —CONH—, —COO—, —OCO—, —O—, —S—, —CH$_2$O—, —CH$_2$S—, —C$_6$H$_4$O—, —C$_6$H$_4$CONH—, —C$_6$H$_4$NHCO—, —C$_6$H$_4$COO—, —C$_6$H$_4$OCO— and —CONHCO—;
- B is one selected from the group consisting of —CONH—, —NHCO—, —COO— and —OCO—;
- m is an integer of from 1 to 3;
- n is an integer of from 1 to 3;
- $R^4$ is an organic group having 1 to 40 carbon atoms or a substituted organic group having 1 to 40 carbon atoms;
- $R^5$ is a hydrocarbon group having 1 to 20 carbon atoms or a substituted hydrocarbon group having 1 to 20 carbon atoms;
- $R^6$ and $R^7$ each independently are a hydrogen atom, a hydrocarbon group having 1 to 20 carbon atoms, a substituted hydrocarbon group having 1 to 20 carbon atoms, or a metal atom.

17. A composite resin comprising the composition of claim 6, a compound (I) represented by formula (1):

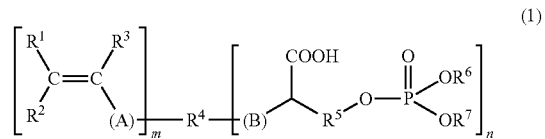

wherein
- $R^1$, $R^2$ and $R^3$ each independently are a hydrogen atom, a cyano group, a hydrocarbon group having 1 to 20 carbon atoms, or a substituted hydrocarbon group having 1 to 20 carbon atoms;
- A is one selected from the group consisting of —CONH—, —COO—, —OCO—, —O—, —S—, —CH$_2$O—, —CH$_2$S—, —C$_6$H$_4$O—, C$_6$H$_4$CONH—, —C$_6$H$_4$NHCO—, —C$_6$H$_4$COO—, —C$_6$H$_4$OCO— and —CONHCO—;
- B is one selected from the group consisting of —CONH—, —NHCO—, —COO— and —OCO—;
- m is an integer of from 1 to 3;
- n is an integer of from 1 to 3;
- $R^4$ is an organic group having 1 to 40 carbon atoms or a substituted organic group having 1 to 40 carbon atoms;
- $R^5$ is a hydrocarbon group having 1 to 20 carbon atoms or a substituted hydrocarbon group having 1 to 20 carbon atoms;
- $R^6$ and $R^7$ each independently are a hydrogen atom, a hydrocarbon group having 1 to 20 carbon atoms, a substituted hydrocarbon group having 1 to 20 carbon atoms, or a metal atom.

18. A method for producing the compound (I) of claim 4, comprising reacting a carboxylic acid represented by formula (2) by condensation reaction with an amine represented by formula (3):

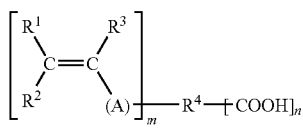
(2)

wherein $R^1$, $R^2$, $R^3$, $R^4$, (A), m and n are the same as those of the formula (1),

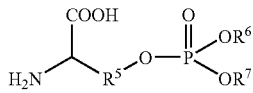
(3)

wherein $R^5$, $R^6$ and $R^7$ are the same as those of the formula (1).

19. The method for producing the compound (I) of claim 18, wherein the carboxylic acid contains a (meth)acryl group.

20. The method for producing the compound (I) of claim 18, wherein a condensing agent present during said reacting is a triazine compound.

21. A method for producing the compound (I) of claim 4, comprising reacting an acid halide represented by formula (4) with an amine represented by formula (3):

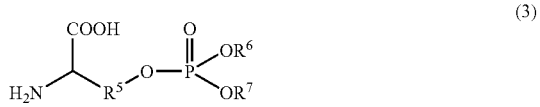
(4)

wherein $R^1$, $R^2$, $R^3$, $R^4$, (A), m and n are the same as those of the formula (1), and X is a halogen atom,

(3)

wherein $R^5$, $R^6$ and $R^7$ are the same as those of the formula (1).

22. The method for producing the compound (I) of claim 21, wherein the acid halide contains a (meth)acryl group.

23. The method for producing the compound (I) claim 18, wherein the amine is a phosphate of an amino acid.

24. The method for producing the compound (I) of claim 23, wherein the amine is one selected from the group consisting of phosphoserine, phosphothreonine and phosphotyrosine.

25. The method for producing the compound (I) claim 21, wherein the amine is a phosphate of an amino acid.

26. The compound (I) of claim 1, wherein A is —COO—.

* * * * *